US012805466B2

(12) United States Patent
Lifshits

(10) Patent No.: US 12,805,466 B2
(45) Date of Patent: Nov. 24, 2026

(54) CUCUMBER VARIETIES NAMED 'HRZ-CS-24-0001H', 'HRZ-CS-24-0003L', AND 'HRZ-CS-24-0004L'

(71) Applicant: Harmoniz LTD, Kfar Menachem (IL)

(72) Inventor: Liora Lea Lifshits, Rehovot (IL)

(73) Assignee: Harmoniz LTD, Kfar Menachem (IL)

( * ) Notice: Subject to any disclaimer, the term of this patent is extended or adjusted under 35 U.S.C. 154(b) by 0 days.

(21) Appl. No.: 19/464,881

(22) Filed: Jan. 30, 2026

(65) Prior Publication Data

US 2026/0231888 A1 Aug. 13, 2026

Related U.S. Application Data

(60) Provisional application No. 63/752,331, filed on Jan. 31, 2025.

(51) Int. Cl.
*A01H 6/34* (2018.01)
*A01H 5/08* (2018.01)

(52) U.S. Cl.
CPC ............... *A01H 6/346* (2018.05); *A01H 5/08* (2013.01)

(58) Field of Classification Search
None
See application file for complete search history.

(56) References Cited

U.S. PATENT DOCUMENTS 4,399,216 A 8/1983 Axel et al.
4,536,475 A 8/1985 Anderson
4,795,855 A 1/1989 Fillatti et al.
4,822,949 A 4/1989 Niego et al.
4,905,411 A 3/1990 Finch-Savage
5,378,824 A 1/1995 Bedbrook et al.
5,451,513 A 9/1995 Maliga et al.
5,492,827 A 2/1996 Dirks
5,501,967 A 3/1996 Offringa et al.
5,527,695 A 6/1996 Hodges et al.
5,591,616 A 1/1997 Hiei et al.
5,693,512 A 12/1997 Finer et al.
5,731,179 A 3/1998 Komari et al.
5,777,196 A 7/1998 Hall
5,948,957 A 9/1999 Chapko et al.
5,969,212 A 10/1999 Getschman
5,994,075 A 11/1999 Goodfellow
6,008,437 A 12/1999 Krebbers et al.
6,051,757 A 4/2000 Barton et al.
6,107,549 A 8/2000 Feng et al.
6,156,953 A 12/2000 Preuss et al.
7,250,554 B2 7/2007 Rommens et al.
8,440,432 B2 5/2013 Voytas et al.
8,450,471 B2 5/2013 Voytas et al.
8,586,363 B2 11/2013 Voytas et al.
8,586,526 B2 11/2013 Gregory et al.
8,592,645 B2 11/2013 DeKelver et al.
8,697,359 B1 4/2014 Zhang
8,697,853 B2 4/2014 Voytas et al.
8,704,041 B2 4/2014 Gordon-Kamm et al.
8,771,945 B1 7/2014 Zhang
8,795,965 B2 8/2014 Zhang
8,865,406 B2 10/2014 Zhang et al.
8,871,445 B2 10/2014 Cong et al.
8,878,012 B2 11/2014 De Haan et al.
8,889,356 B2 11/2014 Zhang
8,889,418 B2 11/2014 Zhang et al.
8,895,308 B1 11/2014 Zhang et al.
8,906,616 B2 12/2014 Zhang et al.
8,912,138 B2 12/2014 Gregory et al.
8,921,112 B2 12/2014 Cai et al.
8,932,814 B2 1/2015 Cong et al.
8,945,839 B2 2/2015 Zhang
8,993,233 B2 3/2015 Zhang et al.
8,999,641 B2 4/2015 Zhang et al.
9,145,565 B2 9/2015 Carroll et al.
9,181,535 B2 11/2015 Liu et al.
11,751,526 B2 9/2023 Dogan
2004/0053236 A1 3/2004 McCallum et al.
2015/0126380 A1 5/2015 Van Dun
2015/0189845 A1 7/2015 Van Der Maas et al.
2015/0245570 A1 9/2015 Vogelaar et al.
2024/0245020 A1* 7/2024 Gonzalez ................ A01H 5/08

FOREIGN PATENT DOCUMENTS

CN 113913548 A 1/2022
EP 0068730 A1 1/1983
EP 0265556 A1 5/1988

(Continued)

OTHER PUBLICATIONS

Author Unknown, "Cornichon Cucumber Fin de Meaux," [website], Borago. [Accessed Apr. 30, 2026, publicly available at URL: https://borago.de/product/Fin%20de%20Meaux-jXkYb77d3OpU], 6 pages.
Author Unknown, "Cucumber Parisian Gherkin F1," [website], All-America Selections, 2015. [Accessed Apr. 30, 2026, publicly available at URL: https://all-americaselections.org/product/cucumber-parisian-gherkin/], 5 pages.
Genbank, Accession No. GS820399.1, "CsB10STC_Bam_05009F_762 ends of BAC library of B10 line of *Cucumis sativus* L. (BamHI) Cucumis sativus genomic, genomic survey sequence," [sequence database entry], National Center for Biotechnology Information (NCBI), unpublished. [Accessed May 1, 2026, publicly available at URL: https://www.ncbi.nlm.nih.gov/nuccore/GS820399], 1 page.
Genbank, Accession No. GS841855.1, "CsB10STC_Bam_35N21F_707 ends of BAC library of B10 line of *Cucumis sativus* L. (BamHI) Cucumis sativus genomic, genomic survey sequence," [sequence database entry], National Center for Biotechnology Information (NCBI), unpublished. [Accessed May 1, 2026, publicly available at URL: https://www.ncbi.nlm.nih.gov/nuccore/GS841855], 1 page.

(Continued)

*Primary Examiner* — Cynthia E Collins
(74) *Attorney, Agent, or Firm* — COOLEY LLP

(57) ABSTRACT

The disclosure relates plants, plant parts, and plant cells of hybrid cucumber plant designated 'HRZ-CS-24-0001H', inbred cucumber plant designated 'HRZ-CS-24-0003L', and inbred cucumber plant designated 'HRZ-CS-24-0004L' and to methods of introducing additional traits into these lines, and to methods for producing cucumber plants having the genetic traits of these lines.

24 Claims, 11 Drawing Sheets

Specification includes a Sequence Listing.

(56) References Cited

FOREIGN PATENT DOCUMENTS

| | | | |
|---|---|---|---|
| EP | 0270822 | A1 | 6/1988 |
| EP | 0334258 | A1 | 9/1989 |
| EP | 0604662 | A1 | 7/1994 |
| EP | 0672752 | A1 | 9/1995 |
| EP | 0686340 | A1 | 12/1995 |
| EP | 2002702 | B1 | 11/2015 |
| EP | 3346825 | B1 | 3/2020 |
| EP | 3313171 | B1 | 8/2024 |
| EP | 2571347 | B1 | 10/2024 |
| JP | 2014239693 | A | 12/2014 |
| NL | 2029503 | B1 | 4/2022 |
| WO | WO-1983003259 | A1 | 9/1983 |
| WO | WO-1985004899 | A1 | 11/1985 |
| WO | WO-1986003516 | A1 | 6/1986 |
| WO | WO-1986003776 | A1 | 7/1986 |
| WO | WO-1992009696 | A1 | 6/1992 |
| WO | WO-1994019930 | A1 | 9/1994 |
| WO | WO-1995016031 | A1 | 6/1995 |
| WO | WO-1997032016 | A1 | 9/1997 |
| WO | WO-1999067357 | A2 | 12/1999 |
| WO | WO-2005048692 | A2 | 6/2005 |
| WO | WO-2005055704 | A2 | 6/2005 |
| WO | WO-2009059777 | A1 | 5/2009 |
| WO | WO-2020169178 | A1 | 8/2020 |

OTHER PUBLICATIONS

Genbank, Accession No. GS860383.1, "CsB10STC_Bam_61D20R_749 ends of BAC library of B10 line of *Cucumis sativus* L. (BamHI) Cucumis sativus genomic, genomic survey sequence," [sequence database entry], National Center for Biotechnology Information (NCBI), unpublished. [Accessed May 1, 2026, publicly available at URL: https://www.ncbi.nlm.nih.gov/nuccore/GS860383.1?report=genbank&log$=seqview], 1 page.

Geneseq, Accession No. BKQ57709, "Cucumber InDel-PHO1 disease-sensitive gene, SEQ ID No. 2," [sequence database record], CAS STN, Geneseq (Clarivate) database, Date of Deposit: Apr. 28, 2022; Entry Date: Apr. 29, 2022. [Accessed May 5, 2026, publicly available at URL: https://www.stn.org/], 2 pages.

Jabbour, "Small Cucumber Varieties: 12 Delicious Options for Your Garden," [website], Savvy Gardening, Mar. 22, 2024; last updated Apr. 29, 2026. [Retrieved from Internet on Apr. 30, 2026, at URL: https://savvygardening.com/small-cucumber/], 21 pages.

Oderings Garden Centres, "Check out our new cucumber variety," [social media post], Facebook, posted Oct. 31, 2023. [Accessed Apr. 30, 2026, publicly available at URL: https://www.facebook.com/OderingsGardenCentres/posts/check-out-our-new-cucumbervariety- the-cucumber-quick-snackthis-quick -producing-/658465873095378/], 1 page.

PCT Application No. PCT/IB2026/050915, International Search Report and Written Opinion mailed Apr. 28, 2026, Applicant: Harmoniz Ltd., 14 pages.

Altschul et al., "Basic Local Alignment Search Tool," Journal of Molecular Biology, (Oct. 5, 1990), 215(3):403-410.

Author Unknown, "Cucumber: AYDA F1," [website], Takii Seed. [Accessed Apr. 13, 2026, publicly available at URL: https://www.takiiseed.com/variety/ayda/], 1 page.

Author Unknown, "Cucumber: Pasadena F1," [website], Agronom. [Accessed Apr. 13, 2026, publicly available at URL: https://agronom.info/en/p/cucumber-pasadena-f1-1065.html], 5 pages.

Author Unknown, "Cucumber SV0091CE," [website], Bayer. [Accessed Apr. 1, 2026, publicly available at URL: https://www.vegetables.bayer.com/au/en-au/products/cucumber/details.html/cucumber_sv0091ce_australia_seminis_all_greenh ouse_all.html], 5 pages.

Author Unknown, "Cucumbers: Postharvest Care and Market Preparation Information Sheet," New Guyana Marketing Corporation. [Accessed Apr. 6, 2026, publicly available at URL: http://www.newgmc.com/gmc_docs/brochures/Cucumber.pdf], 2 pages.

Author Unknown, "Discover the difference between crispy and crunchy," [website], Stable Micro Systems, Aug. 13, 2024. [Retrieved from Internet on Apr. 13, 2026, at URL: https://www.stablemicrosystems.com/blog/2024/discover-the-difference-between-crispy-and-crunchy/], 5 pages.

Author Unknown, "Greenhouse Competitions 2024 Winners," [website], Reach International, Jun. 11, 2024. [Retrieved from Internet on Apr. 6, 2026 at URL: greenhousecompetitions.com/2024/06/11/2024-winners/], 5 pages.

Author Unknown, "Mini Cucumber Picolino," [website], Enza Zaden. [Accessed Apr. 1, 2026, publicly available at URL: https://www.enzazaden.com/za/products-and-services/our-local-varieties/cucumber/Picolino], 2 pages.

Author Unknown, "Picowell RZ F1," [website], Rijk Zwaan. [Accessed Apr. 1, 2026, publicly available at URL: https://www.rijkzwaanusa.com/cucumber/PICOWELL-RZ-F1-prdCS10694-ctgCrops.cucumber], 3 pages.

Author Unknown, "Quete RZ F1 (19-SH741)," [website], Rijk Zwaan. [Accessed Apr. 6, 2026, publicly available at URL: https://www.rijkzwaan.mx/pepino/QUETE-RZ-F1-19-SH741-prdCS10961-ctgCrops.cucumber], 2 pages.

Author Unknown, "Qwerty (F1) Cucumber Seed," [website], Johnny's Selected Seeds. [Accessed Apr. 1, 2026, publicly available at URL: https://www.johnnyseeds.com/vegetables/cucumbers/seedless-and-thin-skinned-cucumbers/qwerty-f1-cucumber-seed-5129.10.html?_gl=1*o9gksn*_up*MQ..*_gs*MQ..&gclid=CjwKCAjwhLPOBhBiEiwA8_wJHIHzdLKsFFNW4L-K4JI-aAp-dP3TzbJheKvRbGJ6_w6MqRx0d2R9cxoCwvcQAvD_BwE&gbraid=0AAAAAD_WiV2mu-NGtbNnH-fKfL3i-VkWt], 6 pages.

Author Unknown, "The Importance of Vegetable Quality Control & Testing for Cucumbers," [website], Clarifresh. [Accessed Apr. 6, 2026, publicly available at URL: https://clarifresh.com/fresh-produce/cucumbers/], 7 pages.

Author Unknown, "When to Pick Cucumbers: How to Know When They're Ready," [website], Humboldts Secret Supplies (HSS), Jul. 26, 2022. [Retrieved from Internet on Apr. 15, 2026 at URL: https://humboldtssecretsupplies.com/blogs/articles/when-to-pick-cucumbers-how-to-know-when-theyre-ready], 6 pages.

Bai et al., "QTLs for Tomato Powdery Mildew Resistance (*Oidium lycopersici*) in *Lycopersicon parviflorum* G1.1601 Co-localize with Two Qualitative Powdery Mildew Resistance Genes," Mol Plant Microbe Interact, (Feb. 2003), 16(2):169-176.

Comai et al., "Efficient discovery of DNA polymorphisms in natural populations by Ecotilling," The Plant Journal, (Mar. 2004), 37(5):778-786.

Dhall et al., "Standardized Protocol for In Situ and In Vitro Maintenance of Ewly Developed Parthenocarpic Gynoecious Cucumber Inbred," Brazilian Archives of Biology and Technology, (Jul. 25, 2022), 65:e22200792; 10 pages.

Fan et al., "A fast, simple, high efficient and one-step generation of composite cucumber plants with transgenic roots by Agrobacterium rhizogenes-mediated transformation," Plant Cell, Tissue and Organ Culture, (Feb. 20, 2020), 141:207-216.

Gao et al., "DNA-guided genome editing using the Natronobacterium gregoryi Argonaute," Nature Biotechnology, (Epub May 2, 2016; published Jul. 2016), 34(7):768-773.

Garvin et al., "DEco-Tilling: an inexpensive method for single nucleotide polymorphism discovery that reduces ascertainment bias," Molecular Ecology Notes, (Epub Apr. 5, 2007; published Sep. 2007), 7(5):735-746.

Gilchrist et al., "Use of Ecotilling as an efficient SNP discovery tool to survey genetic variation in wild populations of Populus trichocarpa," Molecular Ecology, (Epub Mar. 16, 2006; published Apr. 2006), 15(5):1367-1378.

Guan et al., "A near-complete cucumber reference genome assembly and Cucumber-DB, a multi-omics database," Molecular Plant, (Epub Jun. 20, 2024; published Aug. 5, 2024), 17(8):1178-1182, including Supplemental Information, 30 pages.

Gur et al., "Unused natural variation can lift yield barriers in plant breeding," PLoS Biology, (Epub Aug. 24, 2004; published Oct. 2004), 2(10):e245; 1610-1615.

(56) References Cited

OTHER PUBLICATIONS

Harris, "Quantification of Sugars and Organic Acids in 210 Cucumber (*Cucurbis sativus*) Varieties for Genome-wide Association Studies (GWAS)," [M.S. dissertation], Texas Woman's University, (Aug. 2023), 71 pages.
Hazera Seeds, "Hazera—Baby Type Cucumber," [video], YouTube, uploaded Feb. 17, 2025, 31 seconds. [Accessed Apr. 1, 2026, publicly available at URL: https://www.youtube.com/watch?v=_Dmit6Y4014], 5 pages.
Jo et al., "Comparison of Metabolome and Functional Properties of Three Korean Cucumber Cultivars," Front Plant Sci, (eCollection 2022; published Apr. 15, 2022), 13:882120; 14 pages.
Jo et al., "Non-targeted metabolomic analysis for the comparative evaluation of volatile organic compounds in 20 globally representative cucumber lines," Front Plant Sci, (eCollection 2022; published Sep. 29, 2022), 13:1028735; 10 pages.
Kamboj et al., "Quantitative Estimation of Cucurbitacin E in Various Extracts of *Cucumis sativus* L. by Spectrophotometric Method," Int. J. Res. Ayurveda Pharm, (Jul.-Aug. 2016), 7(4):114-122.
Larkin et al., "Clustal W and Clustal X version 2.0.," Bioinformatics, (Epub Sep. 10, 2007; published Nov. 1, 2007), 23(21):2947-2948.
Lusser et al., "New plant breeding techniques. State-of-the-art and prospects for commercial development," JRC Scientific and Technical Reports, Publications Office of the European Union, (Jun. 7, 2011), ISBN: 978-92-79-19715-4, 220 pages. [Accessed Apr. 15, 2026, publicly available at URL: https://publications.jrc.ec.europa.eu/repository/handle/JRC63971].
Makarova et al., "Evolution and classification of the CRISPR-Cas systems," Nature Reviews Microbiology, (Epub May 9, 2011; published Jun. 2011), 9(6):467-477.
Myers et al., "Optimal alignments in linear space," Comput Appl Biosci, (Mar. 1988), 4(1):11-17.
Nakamoto et al., "Effects of sensory combination on crispness and prediction of sensory evaluation value by Gaussian process regression," PLoS One, (Feb. 8, 2024), 19(2):e0297620; 14 pages.
Nanasato et al., "A method of transformation and current progress in transgenic research on cucumbers and *Cucurbita* species," Plant Biotechnology, (Jun. 25, 2020), 37(2):141-146.
Nash, "The Difference Between Crispy and Crunchy, In Excruciating Detail," [website], Chowhound, Nov. 25, 2023. [Retrieved from Internet on Apr. 7, 2026 at URL: https://www.chowhound.com/1452332/what-is-crispy-vs-crunchy-texture-difference/], 4 pages.
Nikolova et al., "Diploidization of cucumber (*Cucumis sativus* L.) haploids by colchicine treatment," Acta Societatis Botanicorum Poloniae, (1996), 65(3-4):311-317.
Ray et al., "Crispy vs. crunchy: The science behind texture that sells," [website], Ingredion, May 22, 2025. [Retrieved from Internet on Apr. 13, 2026 at URL: https://www.ingredion.com/emea/en-uk/be-whats-next/crispy-vs-crunchy-the-science-behind-texture-that-sells], 7 pages.
Reddy et al., "Assessment of total soluble solids, ascorbic acid and acidity in cucumber (*Cucumis sativus* L.) varieties under open and protected conditions," Annals of Phytomedicine, (Epub Dec. 30, 2022), 11(2):684-688.
Suslow et al., "Cucumber," [website], UC Davis Department of Plant Sciences, Postharvest Research and Extension Center, last updated May 1997. [Retrieved from Internet on Apr. 7, 2026 at URL: https://postharvest.ucdavis.edu/produce-facts-sheets/cucumber], 4 pages.
Tan et al., "Recent progress in the regeneration and genetic transformation system of cucumber," Applied Sciences, (Jul. 16, 2022), 12(14):7180; 16 pages.
Tanksley et al., "Advanced backcross QTL analysis: a method for the simultaneous discovery and transfer of valuable QTLs from unadapted germplasm into elite breeding lines," Theoretical and Applied Genetics, (Feb. 1996), 92(2):191-203.
Tunick et al., "Critical Evaluation of Crispy and Crunchy Textures: A Review," International Journal of Food Properties, (Epub Apr. 2, 2013; published 2013), 16(5):949-963.
U.S. Appl. No. 19/465,811, filed Jan. 30, 2026, Inventor: Lifshits.
Valverde-Miranda et al., "Total soluble solids and dry matter of cucumber as indicators of shelf life," Postharvest Biology and Technology, (Oct. 2021), 180:111603; 10 pages.
Wikipedia, "Crispiness," [online encyclopedia], Wikipedia.org, initial publication date unknown; last edited Mar. 22, 2026. [Retrieved from Internet on Apr. 7, 2026 at URL: https://en.wikipedia.org/wiki/Crispiness], 1 page.
Yin et al., "Cucumber transformation methods—the review," Biotechnologia, (2005), 1:95-113.
Zhang et al., "Characterization of Differences in the Composition and Content of Volatile Compounds in Cucumber Fruit," Foods, (Apr. 12, 2022), 11(8):1101; 14 pages.
U.S. Appl. No. 19/465,811, Non-Final Office Action mailed Jun. 26, 2026, Inventor: Lifshifts, Liora Lea., 13 pages.

* cited by examiner

CUCUMBER VARIETIES NAMED 'HRZ-CS-24-0001H', 'HRZ-CS-24-0003L', AND 'HRZ-CS-24-0004L'

CROSS-REFERENCE TO RELATED APPLICATION

This application claims the benefit of U.S. Provisional Application No. 63/752,331 filed on Jan. 31, 2025, which is hereby incorporated by reference in its entirety for all purposes.

REFERENCE TO AN ELECTRONIC SEQUENCE LISTING

The contents of the electronic sequence listing (HALT-001/01US_SeqList_ST26.xml; Size: 100,393 bytes; and Date of Creation: Jan. 21, 2026) are herein incorporated by reference in its entirety.

TECHNICAL FIELD

The present disclosure relates to the field of agriculture, to new and distinctive hybrid cucumber plants, such as a hybrid plant designated 'HRZ-CS-24-0001H' and to methods of making and using such hybrids. The disclosure further relates to inbred cucumber plants designated 'HRZ-CS-24-0003L' and 'HRZ-CS-24-0004L'.

BACKGROUND OF THE DISCLOSURE

Cucumber (*Cucumis sativus*) is a major vegetable crop worldwide and among the most important crop species in the Cucurbitaceae family. They are eaten as a vegetable, either raw, cooked, or made into pickled cucumbers. The more than 100 varieties produce oblong fruits ranging in size from small picklers to large slicers and from can range in color from yellow or brown to a dark green for the cultivated varieties. Modern cultivated cucumbers are typically seedless and while they are generally considered less nutritious than most other fruits, the fresh cucumber is a good source of vitamins A, B1, B5, B6, B9, C, and K, and minerals. Most greenhouse varieties produce fruit without pollination and are gynoecious with respect to flowering, (i.e. produce only female flowers).

A continuing goal of plant breeders is to develop stable, high yielding cucumber hybrids that are agronomically sound or unique. The reasons for this goal are to maximize the amount of fruit produced on the land used (yield) as well as to improve the fruit appearance, the fruit shape and size, eating and processing qualities and/or the plant agronomic and horticultural qualities. To accomplish this goal, the cucumber breeder must select and develop cucumber plants that have the traits that result in superior parental lines that combine to produce superior hybrids.

SUMMARY

The following embodiments and aspects thereof are described in conjunction with systems, tools and methods which are meant to be exemplary, not limiting in scope.

In some aspects, the disclosure relates to a plant, plant part, or plant cell of hybrid cucumber variety 'HRZ-CS-24-0001H', wherein a representative sample of seed of said cucumber variety is deposited under NCIMB Accession No. 44490.

In some aspects, the techniques described herein relate to a method for producing a cucumber plant derived from hybrid cucumber variety 'HRZ-CS-24-0001H', the method including: propagating a vegetative cutting from a stock cucumber plant, thereby producing the cucumber plant derived from variety 'HRZ-CS-24-0001H', wherein the stock cucumber plant is a product of applying a plant breeding technique to 'HRZ-CS-24-0001H', wherein representative seed of the hybrid cucumber variety 'HRZ-CS-24-0001H' has been deposited under NCIMB Accession No. 44490.

In some aspects, the techniques described herein relate to a method for producing a cucumber seed derived from hybrid cucumber variety 'HRZ-CS-24-0001H', the method including: crossing a stock cucumber plant with itself or another cucumber plant, thereby producing the cucumber seed derived from hybrid cucumber variety 'HRZ-CS-24-0001H', wherein the stock cucumber plant is a product of applying a plant breeding technique to 'HRZ-CS-24-0001H', wherein a representative sample of seed of hybrid cucumber variety 'HRZ-CS-24-0001H' has been deposited under NCIMB Accession No. 44490.

In some aspects, the disclosure relates to a seed of cucumber variety 'HRZ-CS-24-0001H', wherein a representative sample of seed of said cucumber variety 'HRZ-CS-24-0001H' is deposited under NCIMB Accession No. 44490.

In some aspects, the techniques described herein relate to a method of introducing a desired trait into hybrid cucumber variety 'HRZ-CS-24-0001H', the method including: introducing a single locus conversion conferring the desired trait into a parental line of hybrid cucumber variety 'HRZ-CS-24-0001H'; and crossing the parental lines having the single locus conversion conferring the desired trait to produce a hybrid cucumber plant having a desired trait and otherwise all the morphological and physiological traits of hybrid cucumber variety 'HRZ-CS-24-0001H'.

In some aspects, the disclosure relates to a prime cucumber fruit of hybrid cucumber variety 'HRZ-CS-24-0001H', wherein said fruit has: a length of between about 4 cm and about 6 cm; a diameter of between about 1 cm and about 2 cm; and a weight of between about 9 grams and about 13 grams, wherein representative seed of hybrid cucumber variety 'HRZ-CS-24-0001H' has been deposited under NCIMB Accession No. 44490.

In some aspects, the disclosure relates to a plant of hybrid cucumber variety 'HRZ-CS-24-0001H' including a transgene conferring a desired trait, a sample of seed of said variety having been deposited under NCIMB Accession No. 44490.

In some aspects, the techniques described herein relate to a method of producing a composite plant, the method including grafting a rootstock or a scion of hybrid cucumber variety 'HRZ-CS-24-0001H' to another plant, thereby producing a composite plant, wherein a representative sample of seed of said cucumber variety is deposited under NCIMB Accession No. 44490.

In some aspects, the techniques described herein relate to a method for producing seed derived from hybrid cucumber plant 'HRZ-CS-24-0001H', the method including: applying a chemical to a plant of variety 'HRZ-CS-24-0001H' to induce male flower formation; growing the plant until it sets at least one fruit; harvesting the fruit; and harvesting at least one seed from the fruit.

In some aspects, the disclosure relates to a plant cell from hybrid cucumber variety 'HRZ-CS-24-0001H', wherein representative seed of the variety has been deposited under NCIMB Accession No. 44490.

In some aspects, the disclosure relates to a plant cell of cucumber variety, which is a descendant of 'HRZ-CS-24-0001H', the descendant expressing the physiological and morphological characteristics of hybrid cucumber variety 'HRZ-CS-24-0001H' as determined at the 5% significance level when grown under substantially similar environmental conditions, wherein representative seed of hybrid cucumber variety 'HRZ-CS-24-0001H' has been deposited under NCIMB Accession No. 44490.

In some aspects, the disclosure relates to a locus converted plant cell from a locus converted plant obtained by introducing a locus conversion into hybrid cucumber variety 'HRZ-CS-24-0001H', wherein the locus converted plant cell is the same as a plant cell from 'HRZ-CS-24-0001H' except for the locus conversion, and a plant grown from the plant cell expresses the physiological and morphological characteristics of hybrid cucumber variety 'HRZ-CS-24-0001H' listed in Table 1 as determined at the 5% significance level except for a trait conferred by the locus conversion, when grown under substantially similar environmental conditions, and wherein representative seed of the variety has been deposited under NCIMB Accession No. 44490.

In some aspects, the techniques described herein relate to use of a hybrid cucumber plant variety designated 'HRZ-CS-24-0001H', wherein representative seed of the variety has been deposited under NCIMB Accession No. 44490, for isolating nucleic acids from the variety.

In some aspects, the techniques described herein relate to use of a hybrid cucumber plant variety designated 'HRZ-CS-24-0001H', wherein representative seed of the variety has been deposited under NCIMB Accession No. 44490, to produce a commodity plant product.

In some aspects, the techniques described herein relate to use of a hybrid cucumber plant variety designated 'HRZ-CS-24-0001H', wherein representative seed of the variety has been deposited under NCIMB Accession No. 44490, to produce a cucumber fruit.

In some aspects, the techniques described herein relate to use of a hybrid cucumber plant variety designated 'HRZ-CS-24-0001H', wherein representative seed of the variety has been deposited under NCIMB Accession No. 44490, to grow subsequent generations.

In some aspects, the techniques described herein relate to use of a hybrid cucumber plant variety designated 'HRZ-CS-24-0001H', wherein representative seed of the variety has been deposited under NCIMB Accession No. 44490, for vegetative propagation.

In some aspects, the techniques described herein relate to use of a hybrid cucumber plant variety designated 'HRZ-CS-24-0001H', wherein representative seed of the variety has been deposited under NCIMB Accession No. 44490, as a recipient of a conversion locus.

In some aspects, the techniques described herein relate to use of a hybrid cucumber plant variety designated 'HRZ-CS-24-0001H', wherein representative seed of the variety has been deposited under NCIMB Accession No. 44490, to produce a genetic marker profile.

In some aspects, the techniques described herein relate to use of a hybrid cucumber plant variety designated 'HRZ-CS-24-0001H', wherein representative seed of the variety has been deposited under NCIMB Accession No. 44490, as a source of seed, wherein said use includes applying a chemical to induce male flower formation.

In some aspects, the techniques described herein relate to use of a hybrid cucumber plant variety designated 'HRZ-CS-24-0001H', wherein representative seed of the variety has been deposited under NCIMB Accession No. 44490, as a crop.

In some aspects, the techniques described herein relate to use of a hybrid cucumber plant variety designated 'HRZ-CS-24-0001H', wherein representative seed of the variety has been deposited under NCIMB Accession No. 44490, as a recipient of a transgene.

In some aspects, the techniques described herein relate to use of a hybrid cucumber plant variety designated 'HRZ-CS-24-0001H', wherein representative seed of the variety has been deposited under NCIMB Accession No. 44490, as a source of breeding material.

In some aspects, the techniques described herein relate to use of a hybrid cucumber plant variety designated 'HRZ-CS-24-0001H', wherein representative seed of the variety has been deposited under NCIMB Accession No. 44490, for producing a plant derived from the variety.

In some aspects, the techniques described herein relate to use of a hybrid cucumber plant variety designated 'HRZ-CS-24-0001H', wherein representative seed of the variety has been deposited under NCIMB Accession No. 44490, for producing a plant derived from the variety having a quantitative trait for a small cucumber fruit phenotype.

In some aspects, the disclosure relates to a plant, plant part, or plant cell of inbred cucumber variety 'HRZ-CS-24-0003L', wherein a representative sample of seed of said cucumber variety is deposited under NCIMB Accession No. 44525.

In some aspects, the techniques described herein relate to a method for producing a cucumber plant derived from inbred cucumber variety 'HRZ-CS-24-0003L', the method including: propagating a vegetative cutting from a stock cucumber plant, thereby producing the cucumber plant derived from variety 'HRZ-CS-24-0003L', wherein the stock cucumber plant is a product of applying a plant breeding technique to 'HRZ-CS-24-0003L', wherein representative seed of the inbred cucumber variety 'HRZ-CS-24-0003L' has been deposited under NCIMB Accession No. 44525.

In some aspects, the techniques described herein relate to a method for producing a cucumber seed derived from inbred cucumber variety 'HRZ-CS-24-0003L', the method including: crossing a stock cucumber plant with itself or another cucumber plant, thereby producing the cucumber seed derived from inbred cucumber variety 'HRZ-CS-24-0003L', wherein the stock cucumber plant is a product of applying a plant breeding technique to 'HRZ-CS-24-0003L', wherein a representative sample of seed of inbred cucumber variety 'HRZ-CS-24-0003L' has been deposited under NCIMB Accession No. 44525.

In some aspects, the disclosure relates to a seed of cucumber variety 'HRZ-CS-24-0003L', wherein a representative sample of seed of said cucumber variety 'HRZ-CS-24-0003L' is deposited under NCIMB Accession No. 44525.

In some aspects, the techniques described herein relate to a method of introducing a desired trait into inbred cucumber variety 'HRZ-CS-24-0003L', the method including: a) crossing cucumber variety 'HRZ-CS-24-0003L' with a second cucumber plant including a desired trait to produce F1 progeny plants, wherein a representative sample of seed of said cucumber variety 'HRZ-CS-24-0003L' is deposited under NCIMB Accession No. 44525; b) selecting F1 progeny plants that have the desired trait to produce selected F1 progeny plants; c) backcrossing selected F1 progeny plants with cucumber variety 'HRZ-CS-24-0003L' to produce backcross progeny plants; d) selecting backcross progeny plants that have the desired trait; and e) repeating steps c) and d) one or more times in succession to produce selected second or higher backcross progeny plants that include the desired trait and otherwise all the physiological and morphological characteristics of cucumber variety 'HRZ-CS-24-0003L'.

In some aspects, the disclosure relates to a prime seedless cucumber fruit of inbred cucumber variety 'HRZ-CS-24-0003L', wherein said fruit has: a length of between about 4 cm and about 5 cm; a diameter of between about 1.0 cm and about 1.5 cm; and a weight of between about 7 grams and about 10 grams, wherein representative seed of inbred cucumber variety 'HRZ-CS-24-0003L' has been deposited under NCIMB Accession No. 44525.

In some aspects, the disclosure relates to a plant of inbred cucumber variety 'HRZ-CS-24-0003L' including a transgene conferring a desired trait, a sample of seed of said variety having been deposited under NCIMB Accession No. 44525.

In some aspects, the techniques described herein relate to a method of producing a composite plant, the method including grafting a rootstock or a scion of inbred cucumber variety 'HRZ-CS-24-0003L' to another plant, thereby producing a composite plant, wherein a representative sample of seed of said cucumber variety is deposited under NCIMB Accession No. 44525.

In some aspects, the techniques described herein relate to a method for producing seed derived from cucumber variety 'HRZ-CS-24-0003L', the method including: applying a chemical to a plant of variety 'HRZ-CS-24-0003L' to induce male flower formation; growing the plant until it sets at least one fruit; harvesting the fruit; and harvesting at least one seed from the fruit.

In some aspects, the disclosure relates to a plant cell from inbred cucumber variety 'HRZ-CS-24-0003L', wherein representative seed of the variety has been deposited under NCIMB Accession No. 44525.

In some aspects, the disclosure relates to a plant cell of cucumber variety, which is a descendant of 'HRZ-CS-24-0003L', the descendant expressing the physiological and morphological characteristics of inbred cucumber variety 'HRZ-CS-24-0003L' as determined at the 5% significance level when grown under substantially similar environmental conditions, wherein representative seed of inbred cucumber variety 'HRZ-CS-24-0003L' has been deposited under NCIMB Accession No. 44525.

In some aspects, the disclosure relates to a locus converted plant cell from a locus converted plant obtained by introducing a locus conversion into inbred cucumber variety 'HRZ-CS-24-0003L', wherein the locus converted plant cell is the same as a plant cell from 'HRZ-CS-24-0003L' except for the locus conversion, and a plant grown from the plant cell expresses the physiological and morphological characteristics of inbred cucumber variety 'HRZ-CS-24-0003L' listed in Table 1 as determined at the 5% significance level except for a trait conferred by the locus conversion, when grown under substantially similar environmental conditions, and wherein representative seed of the variety has been deposited under NCIMB Accession No. 44525.

In some aspects, the techniques described herein relate to use of a cucumber plant variety designated 'HRZ-CS-24-0003L', wherein representative seed of the variety has been deposited under NCIMB Accession No. 44525, for isolating nucleic acids from the variety.

In some aspects, the techniques described herein relate to use of a cucumber plant variety designated 'HRZ-CS-24-0003L', wherein representative seed of the variety has been deposited under NCIMB Accession No. 44525, to produce a commodity plant product.

In some aspects, the techniques described herein relate to use of a cucumber plant variety designated 'HRZ-CS-24-0003L', wherein representative seed of the variety has been deposited under NCIMB Accession No. 44525, to produce a cucumber fruit.

In some aspects, the techniques described herein relate to use of a cucumber plant variety designated 'HRZ-CS-24-0003L', wherein representative seed of the variety has been deposited under NCIMB Accession No. 44525, to grow subsequent generations.

In some aspects, the techniques described herein relate to use of a cucumber plant variety designated 'HRZ-CS-24-0003L', wherein representative seed of the variety has been deposited under NCIMB Accession No. 44525, for vegetative propagation.

In some aspects, the techniques described herein relate to use of a cucumber plant variety designated 'HRZ-CS-24-0003L', wherein representative seed of the variety has been deposited under NCIMB Accession No. 44525, as a recipient of a conversion locus.

In some aspects, the techniques described herein relate to use of a cucumber plant variety designated 'HRZ-CS-24-0003L', wherein representative seed of the variety has been deposited under NCIMB Accession No. 44525, to produce a genetic marker profile.

In some aspects, the techniques described herein relate to use of a cucumber plant variety designated 'HRZ-CS-24-0003L', wherein representative seed of the variety has been deposited under NCIMB Accession No. 44525, as a source of seed, wherein said use includes applying a chemical to induce male flower formation.

In some aspects, the techniques described herein relate to use of a cucumber plant variety designated 'HRZ-CS-24-0003L', wherein representative seed of the variety has been deposited under NCIMB Accession No. 44525, as a crop.

In some aspects, the techniques described herein relate to use of a cucumber plant variety designated 'HRZ-CS-24-0003L', wherein representative seed of the variety has been deposited under NCIMB Accession No. 44525, as a recipient of a transgene.

In some aspects, the techniques described herein relate to use of a cucumber plant variety designated 'HRZ-CS-24-0003L', wherein representative seed of the variety has been deposited under NCIMB Accession No. 44525, as a source of breeding material.

In some aspects, the techniques described herein relate to use of a cucumber plant variety designated 'HRZ-CS-24-0003L', wherein representative seed of the variety has been deposited under NCIMB Accession No. 44525, for producing a plant derived from the variety.

In some aspects, the techniques described herein relate to use of a cucumber plant variety designated 'HRZ-CS-24-0003L', wherein representative seed of the variety has been deposited under NCIMB Accession No. 44525, for producing a plant derived from the variety having a quantitative trait for a small cucumber fruit phenotype.

In some aspects, the disclosure relates to a plant, plant part, or plant cell of inbred cucumber variety 'HRZ-CS-24-0004L', wherein a representative sample of seed of said cucumber variety is deposited under NCIMB Accession No. 44526.

In some aspects, the techniques described herein relate to a method for producing a cucumber plant derived from inbred cucumber variety 'HRZ-CS-24-0004L', the method including: propagating a vegetative cutting from a stock cucumber plant, thereby producing the cucumber plant derived from variety 'HRZ-CS-24-0004L', wherein the stock cucumber plant is a product of applying a plant breeding technique to 'HRZ-CS-24-0004L', wherein representative seed of the inbred cucumber variety 'HRZ-CS-24-0004L' has been deposited under NCIMB Accession No. 44526.

In some aspects, the techniques described herein relate to a method for producing a cucumber seed derived from inbred cucumber variety 'HRZ-CS-24-0004L', the method including: crossing a stock cucumber plant with itself or another cucumber plant, thereby producing the cucumber seed derived from inbred cucumber variety 'HRZ-CS-24-0004L', wherein the stock cucumber plant is a product of applying a plant breeding technique to 'HRZ-CS-24-0004L', wherein a representative sample of seed of inbred cucumber variety 'HRZ-CS-24-0004L' has been deposited under NCIMB Accession No. 44526.

In some aspects, the disclosure relates to a seed of cucumber variety 'HRZ-CS-24-0004L', wherein a representative sample of seed of said cucumber variety 'HRZ-CS-24-0004L' is deposited under NCIMB Accession No. 44526.

In some aspects, the techniques described herein relate to a method of introducing a desired trait into inbred cucumber variety 'HRZ-CS-24-0004L', the method including: a) crossing cucumber variety 'HRZ-CS-24-0004L' with a second cucumber plant including a desired trait to produce F1 progeny plants, wherein a representative sample of seed of said cucumber variety 'HRZ-CS-24-0004L' is deposited under NCIMB Accession No. 44526; b) selecting F1 progeny plants that have the desired trait to produce selected F1 progeny plants; c) backcrossing selected F1 progeny plants with cucumber variety 'HRZ-CS-24-0004L' to produce backcross progeny plants; d) selecting backcross progeny plants that have the desired trait; and e) repeating steps c) and d) one or more times in succession to produce selected second or higher backcross progeny plants that include the desired trait and otherwise all the physiological and morphological characteristics of cucumber variety 'HRZ-CS-24-0004L'.

In some aspects, the disclosure relates to a prime seedless cucumber fruit of inbred cucumber variety 'HRZ-CS-24-0004L', wherein said fruit has: a length of between about 5 cm and about 6.5 cm; a diameter of between about 1.1 cm and about 1.5 cm; and a weight of between about 10 grams and about 13 grams, wherein representative seed of inbred cucumber variety 'HRZ-CS-24-0004L' has been deposited under NCIMB Accession No. 44526.

In some aspects, the disclosure relates to a plant of inbred cucumber variety 'HRZ-CS-24-0004L' including a transgene conferring a desired trait, a sample of seed of said variety having been deposited under NCIMB Accession No. 44526.

In some aspects, the techniques described herein relate to a method of producing a composite plant, the method including grafting a rootstock or a scion of inbred cucumber variety 'HRZ-CS-24-0004L' to another plant, thereby producing a composite plant, wherein a representative sample of seed of said cucumber variety is deposited under NCIMB Accession No. 44526.

In some aspects, the techniques described herein relate to a method for producing seed derived from cucumber variety 'HRZ-CS-24-0004L', the method including: applying a chemical to a plant of variety 'HRZ-CS-24-0004L' to induce male flower formation; growing the plant until it sets at least one fruit; harvesting the fruit; and harvesting at least one seed from the fruit.

In some aspects, the disclosure relates to a plant cell from inbred cucumber variety 'HRZ-CS-24-0004L', wherein representative seed of the variety has been deposited under NCIMB Accession No. 44526.

In some aspects, the disclosure relates to a plant cell of cucumber variety, which is a descendant of 'HRZ-CS-24-0004L', the descendant expressing the physiological and morphological characteristics of inbred cucumber variety 'HRZ-CS-24-0004L' as determined at the 5% significance level when grown under substantially similar environmental conditions, wherein representative seed of inbred cucumber variety 'HRZ-CS-24-0004L' has been deposited under NCIMB Accession No. 44526.

In some aspects, the disclosure relates to a locus converted plant cell from a locus converted plant obtained by introducing a locus conversion into inbred cucumber variety 'HRZ-CS-24-0004L', wherein the locus converted plant cell is the same as a plant cell from 'HRZ-CS-24-0004L' except for the locus conversion, and a plant grown from the plant cell expresses the physiological and morphological characteristics of inbred cucumber variety 'HRZ-CS-24-0004L' listed in Table 1 as determined at the 5% significance level except for a trait conferred by the locus conversion, when grown under substantially similar environmental conditions, and wherein representative seed of the variety has been deposited under NCIMB Accession No. 44526.

In some aspects, the techniques described herein relate to use of a cucumber plant variety designated 'HRZ-CS-24-0004L', wherein representative seed of the variety has been deposited under NCIMB Accession No. 44526, for isolating nucleic acids from the variety.

In some aspects, the techniques described herein relate to use of a cucumber plant variety designated 'HRZ-CS-24-0004L', wherein representative seed of the variety has been deposited under NCIMB Accession No. 44526, to produce a commodity plant product.

In some aspects, the techniques described herein relate to use of a cucumber plant variety designated 'HRZ-CS-24-0004L', wherein representative seed of the variety has been deposited under NCIMB Accession No. 44526, to produce a cucumber fruit.

In some aspects, the techniques described herein relate to use of a cucumber plant variety designated 'HRZ-CS-24-0004L', wherein representative seed of the variety has been deposited under NCIMB Accession No. 44526, to grow subsequent generations.

In some aspects, the techniques described herein relate to use of a cucumber plant variety designated 'HRZ-CS-24-0004L', wherein representative seed of the variety has been deposited under NCIMB Accession No. 44526, for vegetative propagation.

In some aspects, the techniques described herein relate to use of a cucumber plant variety designated 'HRZ-CS-24-0004L', wherein representative seed of the variety has been deposited under NCIMB Accession No. 44526, as a recipient of a conversion locus.

In some aspects, the techniques described herein relate to use of a cucumber plant variety designated 'HRZ-CS-24-0004L', wherein representative seed of the variety has been deposited under NCIMB Accession No. 44526, to produce a genetic marker profile.

In some aspects, the techniques described herein relate to use of a cucumber plant variety designated 'HRZ-CS-24-0004L', wherein representative seed of the variety has been deposited under NCIMB Accession No. 44526, as a source of seed, wherein said use includes applying a chemical to induce male flower formation.

In some aspects, the techniques described herein relate to use of a cucumber plant variety designated 'HRZ-CS-24-0004L', wherein representative seed of the variety has been deposited under NCIMB Accession No. 44526, as a crop.

In some aspects, the techniques described herein relate to use of a cucumber plant variety designated 'HRZ-CS-24-0004L', wherein representative seed of the variety has been deposited under NCIMB Accession No. 44526, as a recipient of a transgene.

In some aspects, the techniques described herein relate to use of a cucumber plant variety designated 'HRZ-CS-24-0004L', wherein representative seed of the variety has been deposited under NCIMB Accession No. 44526, as a source of breeding material.

In some aspects, the techniques described herein relate to use of a cucumber plant variety designated 'HRZ-CS-24-0004L', wherein representative seed of the variety has been deposited under NCIMB Accession No. 44526, for producing a plant derived from the variety.

In some aspects, the techniques described herein relate to use of a cucumber plant variety designated 'HRZ-CS-24-0004L', wherein representative seed of the variety has been deposited under NCIMB Accession No. 44526, for producing a plant derived from the variety having a quantitative trait for a small cucumber fruit phenotype.

In addition to the exemplary aspects and embodiments described above, further aspects and embodiments will become apparent by study of the following descriptions.

BRIEF DESCRIPTION OF THE DRAWINGS

FIG. 2A shows the leaf width, and FIG. 2B shows the leaf length.

DETAILED DESCRIPTION OF THE DISCLOSURE

Definitions

Figure 1:
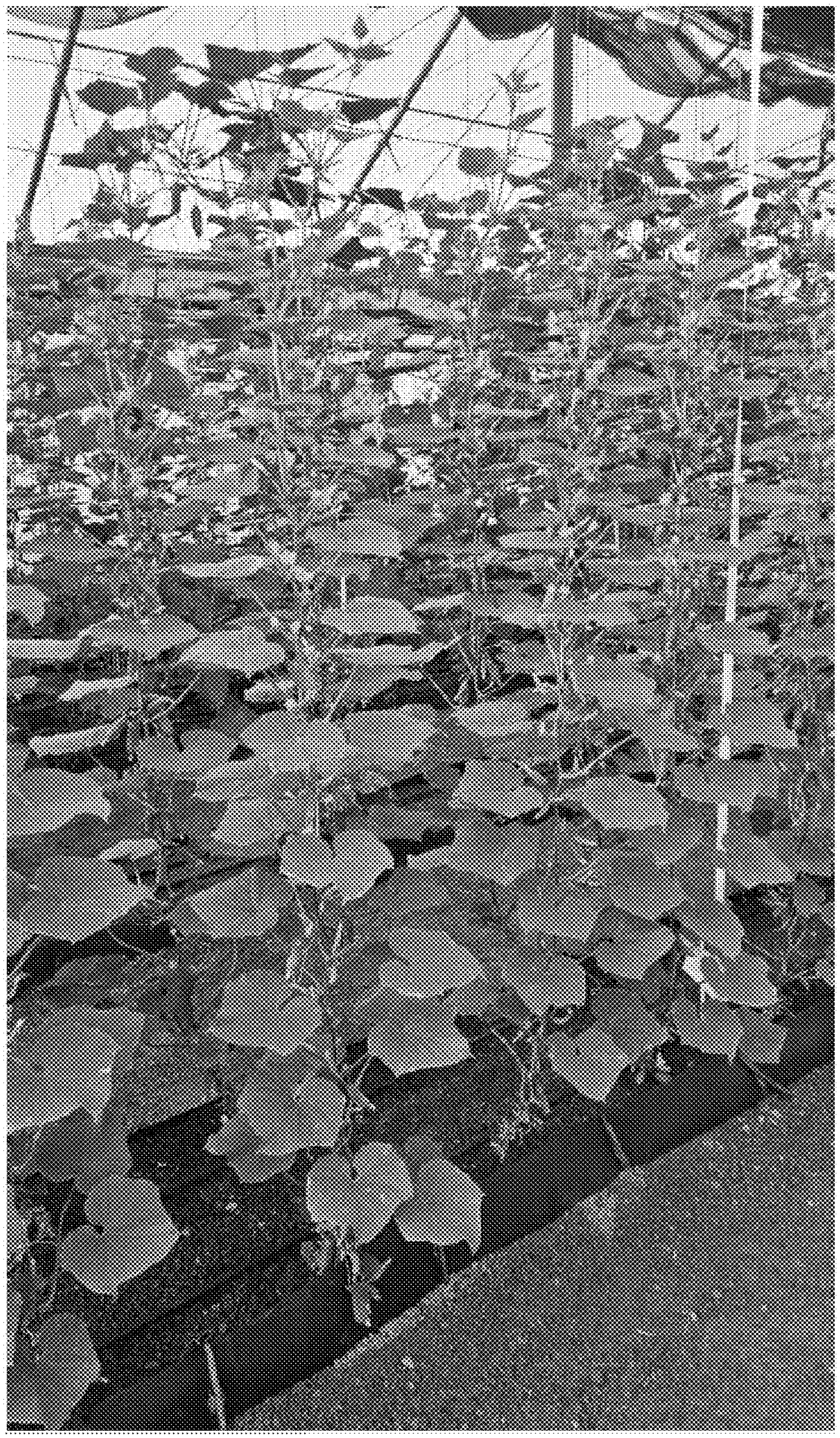
FIG. 1 is a photograph of 'HRZ-CS-24-0001H' plants approximately 10 weeks old, grown in a greenhouse in Israel in the fall of 2024.

In the description and tables that follow, a number of terms are used. In order to provide a clear and consistent understanding of the specification and claims, including the scope to be given such terms, the following definitions are provided:

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about" when immediately preceding a numerical value means a range (e.g., plus or minus 10% of that value). For example, "about 4.0" can mean between 3.6 and 4.4, "about 25,000" can mean 22,500 to 27,500, etc., unless such an interpretation would result in a value above or below range of possible values, such as below 0% or above 100% of a possible value. Furthermore, the phrases "less than about" a value or "greater than about" a value should be understood in view of the definition of the term "about" provided herein, as applied to any recited endpoint. Similarly, the term "about" when preceding a series of numerical values or a range of values (e.g., "about 10, 20, 30" or "about 10-30") refers, respectively to all values in the series, or the endpoints of the range. Unless otherwise indicated, it is to be understood that all numbers expressing quantities, ratios, and numerical properties of ingredients, reaction conditions, and so forth, used in the specification and claims are contemplated to be able to be modified in all instances by the term "about".

The term "approximately" when immediately preceding a numerical value means a range (e.g., plus or minus 5% of that value). For example, "approximately 4.0" can mean 3.8 to 4.2, "approximately 25,000" can mean 23,750 to 26,250, etc., unless such an interpretation would result in a value above or below range of possible values, such as below 0% or above 100% of a possible value. Furthermore, the phrases "less than approximately" a value or "greater than approximately" a value should be understood in view of the definition of the term "approximately" provided herein, as applied to any recited endpoint. Similarly, the term "approximately" when preceding a series of numerical values or a range of values (e.g., "approximately 10, 20, 30" or "approximately 10-30") refers, respectively to all values in the series, or the endpoints of the range. Unless otherwise indicated, it is to be understood that all numbers expressing quantities, ratios, and numerical properties of ingredients, reaction conditions, and so forth, used in the specification and claims are contemplated to be able to be modified in all instances by the term "approximately."

The term "including all ranges and subranges therebetween" or equivalents, are used herein to denote the intention that disclosure of any range or series of possible values, inherently also discloses all ranges and subranges encompassed by the highest and lowest values disclosed. This term includes the entire range from highest to lowest disclosed values, as well as subranges from any two or more disclosed points. This term is also intended to disclose any subranges encompassed anywhere within the highest and lowest disclosed values, including between two points that are explicitly recited in the document, up to one decimal point. Thus, disclosure of values 0, 5, 10, 15, 20, including all ranges and subranges therebetween, should be interpreted as also encompassing a range from 0-20, a range from 0-5 or 5-15, as well as a range from 2-16, or 3.1 to 19.8, etc. Unless otherwise indicated, it is to be understood that all numbers expressing quantities, ratios, and numerical properties of ingredients, reaction conditions, and so forth, used in the specification are contemplated to be able to be modified in all instances by the term "including all ranges and subranges therebetween".

As used herein, the term "and/or" when used in the context of a list of entities, refers to the entities being present singly or in combination. Thus, for example, the phrase "A, B, C, and/or D" includes A, B, C, and D individually, but also includes any and all combinations and sub combinations of A, B, C, and D (e.g., AB, AC, AD, BC, BD, CD, ABC, ABD, and BCD). In some embodiments, one or more of the elements to which the "and/or" refers can also individually be present in single or multiple occurrences in the combinations(s) and/or sub combination(s).

Abscission zone: This is the zone of abscission or separation of the fruit from the peduncle at maturity (controlled by ethylene). The resulting zone (or scar) ranges in size; small (<10 mm), medium (10-15 mm), large (15-20 mm), very large (>20 mm).

Adaptability: A plant that has adaptability is a plant able to grow well in different growing conditions (climate, soils, etc.).

Blossom scar: This is the remnant scar from the stigmatic surface of the blossom. There is a very broad range in sizes; small (<10 mm), medium (10-20 mm), large (20-40 mm) and very large (>40 mm).

Blunt ends. Ends of the cucumber fruits that are not tapered or rounded.

Brix, or degrees Brix (symbol ° Bx) is a measure of the total soluble solids in a liquid, primarily used to determine the sugar content of a solution. One degree Brix equals 1 gram of sucrose in 100 grams of solution, representing the concentration as a percentage by mass. While Brix primarily indicates sucrose content, it can also include other dissolved solids like fructose, glucose, and organic acids. Unless otherwise noted, the Brix referred to herein was measured by squeezing the juice from 3-5 fresh harvested fruits and measuring on a calibrated refractometer Milwaukee MA871.

Cavity: As used herein, cavity refers to the center of the cucumber fruit containing seeds and maternal tissues. Cavity measurements are made on a single fruit or recorded as an average of many fruit at harvest maturity and recorded in a convenient unit of measure.

Cavity ratings: 1=very poor (non-marketable), 3=poor (non-marketable), 5=average (marketable) 7=very good (much better than industry standards), 9=superior (further improvement not attainable). A small cavity has less undesirable placental material and is correlated with better "crunch" a desirable consumer trait.

Cavity to Diameter ratio: Cavity to Diameter ratio is a measure of the cavity size compared to the overall fruit size of a single fruit or the average of many fruit at harvest maturity and recorded in a convenient unit of measure.

Cell expansion: As the cucumber matures, there is a uniform expansion of cells throughout the fruit, leading to the smoothing out of surface irregularities.

Cuticle development: The waxy cuticle on the cucumber's surface becomes more pronounced, contributing to the slightly dull appearance characteristic of prime cucumbers.

As used herein, "crunchy" is used to describe a food that has a dense texture that undergoes a series of fractures when chewed with the molars. It produces relatively loud, low-pitched sounds. Crunchy foods are thicker and denser than crispy foods; they require more force to chew and take longer to break down; and they are associated with multiple fracture events rather than a single snap. Carrots are an example of a crunchy food.

As used herein, a "composite" or "composite plant" refers to a plant comprising two distinct varieties that have been grafted together (rootstock+scion) to form one plant.

Commodity plant product: A "commodity plant product" refers to any composition or product that is comprised of material derived from a plant, seed, plant cell, or plant part of the present disclosure. Commodity plant products may be packaged and sold to consumers and can be viable or nonviable.

Collection of seeds: In the context of the present disclosure a collection of seeds is a grouping of seeds mainly containing similar kind of seeds, for example hybrid seeds of the disclosure, but that may also contain, mixed together with this first kind of seeds, a second, different kind of seeds, of one of the inbred parent lines, for example the inbred line of the present disclosure. A commercial bag of hybrid seeds having the inbred line of the disclosure as a parental line and containing also the inbred line seeds of the disclosure would be, for example such a collection of seeds.

Decreased vigor: A plant having a decreased vigor in the present disclosure is a plant that, compared to other plants has a less vigorous appearance for vegetative and/or reproductive characteristics including shorter plant height, small fruit size, fewer fruit or other characteristics.

Earliness: The earliness relates the number of fruits produced from 12 to 15 days following the beginning of the harvest: the more fruits produced, the more earliness of the plant.

Easy to pick fruit: A fruit that is easy to pick is a fruit that easily detaches from the plant. Once grabbed and twisted, the fruit will break between the peduncle and the stem. For fruits not easy to pick, the peduncle breaks off the fruits. A fruit that is easy to pick is also a fruit that is easily accessible for harvest. When plants have an open plant habit, the fruits are harvested more easily than when the plants have closed habit.

Enhanced nutritional quality: The nutritional quality of the cucumber of the present disclosure can be enhanced by the introduction of several traits comprising a higher endosperm sugar content, flesh texture, brix, aroma content and increased sweetness, increased lycopene content of the peel, etc.

Essentially all of the physiological and morphological characteristics: A plant having essentially all of the physiological and morphological characteristics means a plant having all the physiological and morphological characteristics of a plant of the present disclosure, except for additional traits and/or mutations which do not materially affect the plant of the present disclosure, or a genome editing with endonucleases such as chemical nucleases, meganucleases, ZFNs, and desired characteristic(s), which can be indirectly obtained from another plant possessing at least one single locus conversion via a conventional breeding program (such as backcross breeding) or directly obtained by introduction of at least one single locus conversion via New Breeding Techniques. In some embodiments, one of the non-limiting examples for a plant having (and/or comprising) essentially all the physiological and morphological characteristics shall be a plant having all the physiological and morphological characteristics of a plant of the present disclosure other than desired, additional trait(s)/characteristic(s) conferred by a single locus conversion including, but not limited to, a converted or modified gene.

The term "engineered" or "genetically engineered" refers to any man-made manipulation of a genome of a cell of interest.

Flesh color: In the context of the present disclosure, the flesh color is the color of the cucumber flesh.

Field holding ability: Field holding ability is the ability for fruit quality to maintain even after fruit is ripe.

Fruit color. Fruit color is defined as degree of intensity of green on the exterior skin of the cucumber fruit. Fruit color ratings: 1=very light, 3-light, 5-medium, 7-dark, 9=very dark.

Flesh firmness or tissue firmness can be measured for resistance of flesh against a given pressure. Firmness ratings 1=very poor (non-marketable), 3=poor (non-marketable), 5=average (marketable) 7=very good (much better than industry standards), 9=superior (further improvement not attainable). Fruit flesh firmness may also be measured as lbs/square inch resistance.

Fruit Diameter. The cross-sectional diameter of a single fruit or the average of many fruits measured at harvest maturity or prime and recorded in a convenient unit of measure.

Fruit Length. The longitudinal linear length of a single fruit or the average of many fruits measured from stem end to calyx end at harvest maturity or prime and recorded in a convenient unit of measure.

Fruit Weight. The weight of a single fruit or the average of many fruits measured at harvest maturity and recorded in a convenient unit of measure.

Grafting: Grafting is the operation by which a rootstock is grafted with a scion.

Immature fruit: As used herein, fruits were designated immature as long as they remained green and suitable for consumption. Upon full maturation, cucumber fruit becomes a yellowish color, hardens, and is no longer edible.

Immunity to disease(s) and or insect(s): A cucumber plant which is not subject to attack or infection by specific disease(s) and or insect(s) is considered immune.

Industrial usage: The industrial usage of the cucumber of the present disclosure comprises the use of the cucumber fruit for consumption, whether as fresh products or in canning, freezing or any other industries.

Intermediate resistance to disease(s) and or insect(s): A cucumber plant that restricts the growth and development of specific disease(s) and or insect(s) but may exhibit a greater range of symptoms or damage compared to a resistant plant. Intermediate resistant plants will usually show less severe symptoms or damage than susceptible plant varieties when grown under similar environmental conditions and/or specific disease(s) and or insect(s) pressure but may have heavy damage under heavy pressure. Intermediate resistant cucumber plants are not immune to the disease(s) and or insect(s).

Indeterminate vine or Indeterminate Growth. Refers to apical meristem producing an unrestricted number of lateral organs, characteristic of vegetative apical meristems. (Anatomy of Seed Plants, $2^{nd}$ Edition, 1977, John Wiley and Sons, page 513). The main stem of the plant continues to grow as long as the plant stays healthy, as opposed to a determinate plant, which at some point in its life cycle will stop growing longer.

Prime fruit. As used herein, "prime fruit" or "prime cucumber fruit" means the cucumber fruit has reached the expected length and diameter for the variety, and is at peak quality for consumer consumption. For 'HRZ-CS-24-0001H', the fruit is prime when it reaches a length of between about 4.0 cm and about 6.5 cm.

New Breeding Techniques: New breeding techniques (NBTs) are various new technologies developed and/or used to create new characteristics in plants through genetic variation, the aim being targeted mutagenesis, targeted introduction of new genes or gene silencing (RdDM). The following breeding techniques are within the scope of NBTs: targeted sequence changes facilitated through the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), genome editing with endonucleases such as chemical nucleases, meganucleases, ZFNs, and Transcription Activator-Like Effector Nucleases (TALENs, see U.S. Pat. Nos. 8,586,363 and 9,181,535, incorporated by reference in their entireties), the CRISPR/Cas system ((using such as Cas9, Cas12a/Cpf1, Cas13/C2c2, CasX and CasY; also see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques-State-of-the-art and prospects for commercial development", which is incorporated by reference in its entirety.

"Non-propagatable" as used herein means that one could not produce or reproduce a plant from the "non-propagatable" plant part, for example, a non-propagatable seedless cucumber, exclusively by means of an essentially biological process.

Nonviable as used herein means that one could not produce or reproduce a plant from the "nonviable" fruit, "nonviable" seed, etc.

Number of Boxes per Acre: The Number of Boxes per Acre—6's, 9's, 12's, 15's, 18's or 23's refers to the number of fruit that fit into a standard cucumber box.

Open Plant Habit: An open plant habit is a plant where the fruits are visible without moving the leaves. A plant with closed habit will have its fruit hidden by leaves that have a high density. An average open plant habit will be between the open and closed habit, and the plant will have medium leaf density. Whether a plant has open habit or closed habit is based on the whole of the plant. The more erect the plant, the more compact and therefore the closer the habit. In contrast, when the plant is lodging, sprawling on the ground, it leads to a less compact plant, therefore more "open".

Overall Rating: A final or Overall Rating is assigned to variety performance or a varieties characteristic in test or trial situations of a variety. Overall Rating can range from 1=very poor to 10 excellent.

"Parthenocarpy," or "parthenocarpic" is well understood in the art and is a term used to describe the development of fruits without fertilization of the female ovule, thus as a consequence the fruits are seedless. Likewise a "parthenocarpic plant" means that the plant produces seedless fruits without pollination of the female flowers.

"Facultative parthenocarpy" as used herein means that the parthenocarpy trait is not seen when the flower of the facultative parthenocarpic plant is pollinated, in which case normal fertilization and normal fruit development takes place. As normal fertilization takes place, the fruits are seeded.

Plant adaptability: A plant having good plant adaptability means a plant that will perform well in different growing conditions and seasons.

Plant Part: As used herein, the term "plant part", "part thereof" or "parts thereof" includes plant cells, plant protoplasts, plant cell tissue cultures from which cucumber plants can be regenerated, plant calli, plant clumps and plant cells that are intact in plants or parts of plants, such as embryos, embryo sacs, pollen grains, ovules, flowers, seeds, fruits, rootstocks, scions, stems, roots, anthers, pistils, petioles, stalks, root tips, leaves, meristematic cells, axillary buds, hypocotyls, cotyledons, ovaries, seed coats, endosperms and the like.

Plant Habit: A plant can be an upright plant (also called erect) providing good coverage for the fruit or it can be open with a weaker habit exposing the fruit The term "plant variety" is used herein as a group of plants that share a set of characteristics. The 1991 UPOV Convention's Article 1 (vi) states that a plant variety is a grouping within a botanical taxon of the lowest known rank. The grouping can be defined by the characteristics that result from a specific genotype or combination of genotypes. This includes synthetic varieties and hybrids.

Quantitative Trait Loci (QTL): Quantitative trait loci refer to genetic loci that control to some degree numerically representable traits that are usually continuously distributed.

Reduced blossom end striping: Cucumber fruit normally have a striped pattern at the blossom end. The stripes are lighter color green or yellowish.

Regeneration: Regeneration refers to the development of a plant from tissue culture.

Resistance to disease(s) and or insect(s): A cucumber plant that restricts the growth and development of specific disease(s) and or insect(s) under normal disease(s) and or insect(s) attack pressure when compared to susceptible plants. These cucumber plants can exhibit some symptoms or damage under heavy disease(s) and or insect(s) pressure. Resistant cucumber plants are not immune to the disease(s) and or insect(s).

Ribs: The ribs on the fruit may be prominent, inconspicuous or nonexistent. They refer to the ridges along the fruit mostly near the peduncle.

Rootstock: A rootstock is the lower part of a plant capable of receiving a scion in a grafting process.

Scion: A scion is the higher part of a plant capable of being grafted onto a rootstock in a grafting process.

Skin firmness. Skin firmness subjectively tested under field conditions for resistance of fruit exterior against a given pressure. Range is soft, medium, firm and very firm. Fruit exterior firmness may also be measured as lbs/square inch resistance.

Seedless: Seedless as used herein means fruits without seeds, or having nonviable seeds and/or seed parts.

Semi-erect habit: A semi-erect plant has a combination of lateral and upright branching and has an intermediate type habit between a prostate plant habit, having laterally growing branching with fruits most of the time on the ground and an erect plant habit with branching going straight up with fruit being off the ground.

"Sequence identity" or "identity" in the context of two nucleic acid or polypeptide sequences includes reference to the number of residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art, e.g., according to the algorithm of Meyers and Miller, Computer Applic. Biol. Sci., 4:11-17 (1988). The comparison of sequences and determination of percent identity between two sequences can be accomplished using a mathematical algorithm, for example, NCBI Basic Local Alignment Search Tool (BLAST®) (Altschul et al. 1990 J. Mol. Biol. 215:403-10), which is available from several sources, including the National Center for Biotechnology Information (NCBI, Bethesda, Md.) and on the Internet, for use in connection with the sequence analysis programs blastp, blastn, blastx, tblastn and tblastx, and the Clustal W and Clustal X (Larkin et al. 2007 Bioinformatics, 23, 2947-294, Clustal W and Clustal X version 2.0) as well as Clustal Omega. Unless otherwise stated, references to sequence identity used herein refer to the Clustal Omega.

Seed cavity formation: In prime cucumbers, a jelly-like material begins to form in the seed cavity, indicating proper maturity for harvest. See for example, Cucumber-Recommendations for Maintaining Postharvest Quality, available on the worldwide web at postharvest.ucdavis.edu/produce-facts-sheets/cucumber.

Single locus converted (conversion): Single locus converted (conversion) plants refer to plants which are developed by plant breeding techniques or obtained though artificially induced mutagenesis or through the use of New Breeding Techniques described in the present disclosure, wherein essentially all of the desired morphological and physiological characteristics of a plant are recovered in addition to a single locus transferred into the plant.

Soluble Solids: Soluble solids refer to the percent of solid material found in the fruit tissue, the majority of which is sugars. Soluble solids are estimated with a refractometer and measured as degrees Brix.

The term "smaller leaf area" as used herein is the leaf area that displays a reduction in individual leaf area of at least 10% as a result of the presence of the genetic trait for small cucumber fruit disclosed herein, compared to plants that do not have this genetic trait, and grown under the same conditions.

The term "shorter internodes" or "shorter internode length" as used herein is internode length that has a reduction in individual length of at least 10% as a result of the genetic trait disclosed herein, compared to plants that do not have this genetic trait, and are grown under the same conditions.

Susceptible to disease(s) and or insect(s): A cucumber plant that is susceptible to disease(s) and or insect(s) is defined as a cucumber plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses: A cucumber plant that is tolerant to abiotic stresses has the ability to endure abiotic stress without serious consequences for growth, appearance and yield.

Uniformity: Uniformity, as used herein, describes the similarity between plants or plant characteristics which can be a described by qualitative or quantitative measurements.

Vine Overall: An overall rating assigned to the performance of a plant's vine. Vine Overall can range from 1=very poor to 10 excellent.

Overview

The disclosure relates to a hybrid cucumber plant designated 'HRZ-CS-24-0001H', to the seeds of hybrid cucumber 'HRZ-CS-24-0001H', to the plant parts of hybrid cucumber 'HRZ-CS-24-0001H', to methods of introducing additional traits into 'HRZ-CS-24-0001H', and to methods for producing cucumber plants having the genetic traits of 'HRZ-CS-24-0001H' by applying a breeding technique to hybrid cucumber 'HRZ-CS-24-0001H'.

The disclosure also relates to inbred cucumber plant designated 'HRZ-CS-24-0003L', to the seeds of cucumber 'HRZ-CS-24-0003L', to the plant parts of cucumber 'HRZ-CS-24-0003L', to methods of introducing additional traits into 'HRZ-CS-24-0003L', and to methods for producing cucumber plants having the genetic traits of 'HRZ-CS-24-0003L' by applying a breeding technique to cucumber 'HRZ-CS-24-0003L'.

The disclosure also relates to inbred cucumber plant designated 'HRZ-CS-24-0004L', to the seeds of cucumber 'HRZ-CS-24-0004L', to the plant parts of cucumber 'HRZ-CS-24-0004L', to methods of introducing additional traits into 'HRZ-CS-24-0004L', and to methods for producing cucumber plants having the genetic traits of 'HRZ-CS-24-0004L' by applying a breeding technique to cucumber 'HRZ-CS-24-0004L'.

The cucumber varieties of the disclosure have quantitative traits resulting in small fruit and an increased number of fruits per plant. Cucumber fruits of the present disclosure are ready for harvest (at prime) when they are about 5 cm in length, or between 4 cm-and 6 cm in length. The small prime fruit and increased number of fruits is hypothesized to be the result of smaller flowers and shorter internode lengths, and is associated with the homozygous recessive polymorphisms disclosed herein.

Cucumber

*Cucumis sativus* is a member of the family Cucurbitaceae. The Cucurbitaceae is a family of about 90 genera and 700 to 760 species, mostly of the tropics. The family includes cucumbers, squashes, gourds, watermelon, loofah and several weeds. The genus *Cucumis*, to which the cucumber, cucumbers, and several melons belong, includes about 70 species. The cucumber is believed to be native to India or Southern Asia and has been apparently there for 3000 years.

Practically speaking, all cultivated forms of cucumber belong to the highly polymorphic species *Cucumis sativus* L. that is grown for its edible fruit. Example subspecies of *C. sativus* L. include *C. sativus* var. *hokutosei, C. sativus* var. *hardwickii, C. sativus* var. long green, *C. sativus* var. *sikkimensis, C. sativus* var. *sativus, C. sativus* cv. winter long, and *C. sativus* var. *xishuangbannesis*. Cucumber varieties may be monoecious (producing both male and female flowers) or gynoecious (producing only female flowers and seedless fruit).

Cucumber is distinct from other *Cucumis* species in that it has seven pairs of chromosomes (2n=2x=14) whereas most others have twelve pairs or multiple of twelve. Pollination techniques for controlled crosses in cucumbers are easy to conduct. If bees and natural pollen vectors can be excluded, the breeder need not to be concerned about preventing selfing or other pollen contamination because of the diclinous nature of cucumbers and the stickiness or adherence of pollen to its source flower. There is no wind dissemination of pollen. Pistillate flowers are receptive in the morning or up to midday on the day they open. Cucumbers have a broad range of floral morphologies, from staminate, pistillate to hermaphrodite flowers, yielding several types of sex expression.

As a crop, cucumbers are grown commercially wherever environmental conditions permit the production of an economically viable yield. The term cucumber, as used herein, refers to the American usage of the term which is used to describe the fruit, which depending on the type and use, could commonly be called a slicing cucumber or a pickle. Cucumbers that are grown for fresh market, also called slicers and are generally hand harvested. Those that are to be processed are called pickles and may be hand or mechanically harvested. The fruit are produced on trailing or climbing vines and can be cultivated prostrate on the soil or trained to a trellis. On healthy plants there is a canopy of large, regular, three lobed leaves, in an alternate arrangement. Fruits are typically white flesh at the consumption stage, but may be white, green or slightly orange at seed maturity.

Fresh cucumbers are available in the United States year-round although the greatest supply is from June through October. Fresh cucumbers are consumed in many forms. They are eaten sliced or pickled and used as an ingredient in prepared sauces, such as cucumber dip or as toppings on sandwiches and burgers.

Pickling cucumbers grown in the United States typically have blunt and angular fruits. They are white-spined and most possess dark green or medium dark green exterior color. Most slicers have slightly rounded ends and taper slightly from the stem to blossom end, although cylindrical-shaped fruits with blocky or even rounded ends are also available. Many changes that occurred with the domestication of the cucumber relate to fruit morphology, with a specialization in fruit shape and size. Slicing cucumbers are frequently sold in lengths from 6 to 10 inch and diameter varies from 1.5 to nearly 3 inches. In the United States, the principal slicer cucumber growing regions are Georgia, Florida, Michigan, California and North Carolina with nearly 42,000 acres out of a US total acreage of 57,500 acres. The main states that produce processing cucumbers are Michigan, North Carolina and Texas. Fresh cucumbers are available in the United States mainly from spring to fall. Cucumbers are consumed in many forms, generally processed for pickling types and as fresh market product for slicers. Although slicing cultivars may be processed, they generally are not acceptable substitutes for the pickling cucumbers.

The cucumber lines described herein produce prime fruits which are considered snacking cucumbers. Snacking cucumbers are often crispier than immature larger cucumber varieties due to the levels of pectins and cellulose in the cell walls. Snacking cucumbers also typically have a lower water content and a denser flesh structure, which contributes to a firmer texture, as well as thinner and less waxy skin texture.

Large field spaces are required for cucumber breeding and the need for labor intensive hand pollination for self as well as cross pollination has resulted in a lag in the knowledge of cucumber genetics relative to such crops as tomato. Cucumber flowers open after sunrise; the exact time depends on environmental conditions such as sunlight, temperature and humidity. The flower closes permanently in the afternoon of the same day. Almost all pollen is collected and transferred before noon. Typically, flowers are staminate although some are also hermaphroditic. Although hermaphroditic flowers are self-fertile, they are incapable of performing self-pollination. Insects are required for pollination. The primary pollinators are bees, particularly honeybees.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In cucumber, these important traits may include higher yield, field performance, compact growth, fruit and agronomic quality such as sugar levels, small cavity size, flesh color or texture, resistance to diseases and insects, ease of fruit setting, adaptability for soil and climate conditions, field holding, harvest flexibility and tolerance to drought and heat.

Particularly desirable traits that may be incorporated by this disclosure are improved resistance to different viral, fungal, and bacterial pathogens and improved resistance to insect pests. Important diseases include but are not limited to Powdery mildew (Sphaerotheca *fuliginea*), *Fusarium* wilt race 0, 1, 2 (*Fusarium oxysporum melonis*), Downy mildew (*Pseudoperonospora cubensis*), Cucumber mosaic virus, watermelon mosaic virus, zucchini mosaic virus, *papaya* ringspot virus, melon aphid (*Aphis gossypii*).

Other desirable traits include traits related to improved cucumber fruits. A non-limiting list of fruit phenotypes used during breeding selection include skin firmness, fruit color, fruit diameter, fruit length, fruit weight, overall taste, field holding ability, and shelf or storage life.

Development of Hybrid Cucumber Variety 'HRZ-CS-24-0001H'

Hybrid cucumber variety 'HRZ-CS-24-0001H' is the F1 hybrid offspring of a cross between proprietary parental cucumber lines 'LB24-F12-1363' (also known as 'HRZ-CS-24-0003L') and 'LB23-F5-1049' ('HRZ-CS-24-0004L'). Either line can be used as the female parent to produce 'HRZ-CS-24-0001H'.

The seeds of 'HRZ-CS-24-0001H' can be grown to produce hybrid plants and parts thereof. Hybrid 'HRZ-CS-24-0001H' can be seed propagated by crossing cucumber line 'HRZ-CS-24-0003L' with cucumber line 'HRZ-CS-24-0004L' and can be vegetatively propagated.

Parental cucumber line 'HRZ-CS-24-0003L' has been selfed 12 generations and reproduces true to type.

Parental cucumber line 'HRZ-CS-24-0004L' has been selfed five generations and reproduces true to type.

Description of Hybrid Cucumber Variety 'HRZ-CS-24-0001H'

Hybrid cucumber variety 'HRZ-CS-24-0001H' produces parthenocopic snacking cucumbers. Additionally, hybrid cucumber variety 'HRZ-CS-24-0001H' comprises quantitative traits wherein the plants produce smaller fruits in greater quantities compared to other cucumber varieties. It is hypothesized that these quantitative traits are the result of smaller flowers and shorter internode lengths.

Hybrid cucumber plant 'HRZ-CS-24-0001H' is similar to hybrid cucumber variety 'Qwerty'. 'Qwerty' is a commercial variety. As shown in Tables 1 and 2A-C, while 'HRZ-CS-24-0001H' is similar to hybrid cucumber plant 'Qwerty', there are significant differences including the length of internodes, leaf size, flower size, and size of prime fruit.

Description of Inbred Cucumber Variety 'HRZ-CS-24-0003L'

Inbred cucumber variety 'HRZ-CS-24-0003L' produces parthenocopic snacking cucumbers. Additionally, cucumber variety 'HRZ-CS-24-0003L' is a parental line of 'HRZ-CS-24-0001H' and also produces small cucumber fruits in greater quantities compared to other cucumber varieties.

Cucumber plant 'HRZ-CS-24-0003L' is similar to hybrid cucumber variety 'Qwerty' and hybrid cucumber variety 'HRZ-CS-24-0001H'. 'Qwerty' is a commercial variety. As shown in Tables 1 and 2A-C, while 'HRZ-CS-24-0003L' is similar to hybrid cucumber plant 'Qwerty', there are significant differences including the length of internodes, leaf size, and size of prime fruit.

Description of Inbred Cucumber Variety 'HRZ-CS-24-0004L'

Inbred cucumber variety 'HRZ-CS-24-0004L' produces parthenocopic snacking cucumbers. Additionally, cucumber variety 'HRZ-CS-24-0004L' is a parental line of 'HRZ-CS-24-0001H' and also produces small cucumber fruits in greater quantities compared to other cucumber varieties.

Cucumber plant 'HRZ-CS-24-0004L' is similar to hybrid cucumber variety 'Qwerty' and hybrid cucumber variety 'HRZ-CS-24-0001H'. 'Qwerty' is a commercial variety. As shown in Tables 1 and 2, while 'HRZ-CS-24-0003L' is similar to hybrid cucumber plant 'Qwerty', there are significant differences including the length of internodes, leaf size, and size of prime fruit.

Cucumber plants 'HRZ-CS-24-0001H', 'HRZ-CS-24-0003L', and 'HRZ-CS-24-0004L' have shown uniformity and stability for the traits, within the limits of environmental influence for the traits as described in the following Variety Descriptive Information (Tables 1 and 2A-C). No variant traits have been observed or are expected for important agronomical traits in cucumber hybrid 'HRZ-CS-24-0001H' and inbred lines 'HRZ-CS-24-0003L' and 'HRZ-CS-24-0004L'.

Hybrid cucumber plant 'HRZ-CS-24-0001H' and inbred parental lines 'HRZ-CS-24-0003L' and 'HRZ-CS-24-0004L' have the following morphologic and other characteristics, as compared to 'Qwerty', based primarily on data collected in Canada and Israel. All experiments done under the direct supervision of the Applicant). Descriptions and measurements follow the guidelines set forth in the CPVO protocol for tests on distinctness, uniformity and stability for *Cucumis sativus* L., CPVO-TP/061/2 Rev.2 dated Mar. 19, 2019. Whole plants of hybrid cucumber plant 'HRZ-CS-24-0001H' are shown in FIG. 1.

TABLE 1

| | Variety Descriptive Information | | | | |
|---|---|---|---|---|---|
| | Trait | 'HRZ-CS-24-0001H' | 'HRZ-CS-24-0003L' | 'HRZ-CS-24-0004L' | 'Qwerty' |
| 1 | VG Cotyledon: bitterness | 1-absent | | | 9-present |
| 2 | VG Plant: growth type | 2-indeterminate | 2-indeterminate | 2-indeterminate | 2-indeterminate |
| 3 | MG/MS Plant: total length of first 15 internodes | 1-very short | 1-very short | 1-very short | 3-short |
| 4 | VG Leaf blade: attitude | 2-horizontal | 2-horizontal | 2-horizontal | 3-drooping |
| 5 | MS/VG Leaf blade: length | 3-short | | | 5-medium |
| 6 | MS/VG Leaf blade: ratio length of terminal | 5-medium | | | 5-medium |
| 7 | VG Leaf blade: shape of apex of terminal lobe | 2-right-angled | | | 2-right-angled |
| 8 | VG Leaf blade: intensity of green color | 7-dark | | | 5-medium |
| 9 | VG Leaf blade: blistering | 1-absent or very weak | 1-absent or very weak | 1-absent or very weak | 1-absent or very weak |
| 10 | VG Leaf blade: undulation of margin | 2-moderate | | | 2-moderate |
| 11 | VG Leaf blade: dentation of margin | 5-medium | | | 5-medium |
| 12 | MG Time of development of female flowers (80% of plants with at least one female flower) | 3-early | | | 3-early |
| 13 | VG Plant: sex expression | 3-gynoecious | 3-gynoecious | 3-gynoecious | 3-gynoecious |
| 14 | VG Plant: number of female flowers per node | 7-predominantly more than five | 7-predominantly more than five | 7-predominantly more than five | 2-predominantly one or two |
| 15 | VG Ovary: color of vestiture | 1-white | 1-white | 1-white | 1-white |
| 16 | VG Parthenocarpy | 9-present | 9-present | 9-present | 9-present |
| 17 | MS/VG Fruit: length | 1-very short | 1-very short | 1-very short | 3-short |
| 18 | MS/VG Fruit: diameter | 3-small | 3-small | 3-small | 3-small |
| 19 | MS/VG Fruit: ratio length/diameter | 1-very small | 1-very small | 1-very small | 5-medium |
| 20 | VG Fruit: core diameter in relation to diameter of fruit | 7-large | | | 5-medium |
| 21 | VG Fruit: shape in transverse section | 2-round to angular | 2-round to angular | 2-round to angular | 2-round to angular |
| 22 | VG Fruit: shape of stem end | 3-obtuse | | | 2-acute |
| 23 | VG Only necked varieties: Fruit: length of neck | | | | |
| 24 | VG Fruit: shape of calyx end | 2-obtuse | | | 4-truncate |
| 25 | VG Fruit: ground color of skin at market stage | 3-green | 3-green | 3-green | 3-green |
| 26 | VG Excluding white varieties: Fruit: intensity of ground color of skin | 5-medium | | | 5-medium |
| 27 | VG Fruit: ribs | 1-absent or weak | | | 1-absent or weak |
| 28 | VG Fruit: sutures | 9-present | | | 1-absent |
| 29 | VG Fruit: creasing | 1-absent | 1-absent | 1-absent | 1-absent |
| 30 | VG Fruit: degree of creasing | N/A | N/A | N/A | N/A |
| 31 | VG Fruit: type of vestiture | 1-hairs only | 1-hairs only | 1-hairs only | 1-hairs only |
| 32 | VG Fruit: density of vestiture | 5-medium | | | 3-sparse |
| 33 | VG Only varieties with white ovary | 1-white | | | 1-white |
| 34 | VG Fruit: warts | 1-absent | 1-absent | 1-absent | 1-absent |
| 35 | VG Fruit: size of warts | N/A | N/A | N/A | N/A |
| 36 | VG Fruit: length of stripes | 3-short | | | 1-absent or very short |
| 37 | VG Fruit: dots | 1-absent | 1-absent | 1-absent | 1-absent |
| 38 | VG Fruit: distribution of dots | N/A | N/A | N/A | N/A |
| 39 | VG Fruit: length of fruit containing dots | N/A | N/A | N/A | N/A |
| 40 | VG Fruit: density of dots | N/A | N/A | N/A | N/A |
| 41 | VG Fruit: glaucosity | 5-medium | | | 5-medium |
| 42 | MS/VG Fruit: length of peduncle | 3-short | | | 5-medium |
| 43 | VG Fruit: ground color of skin at physiological ripeness | 2-yellow | 2-yellow | 2-yellow | 3-green |
| 44 | VG/VS Resistance to *Cladosporium cucumerinum* (Ccu) | 1-absent | 1-absent | 1-absent | 9-present |
| 45 | VG/VS Resistance to Cucumber mosiac virus (CMV) | 1-absent | 1-absent | 1-absent | 9-present |
| 46 | VG/VS Resistance to Powdery mildew (*Podosphaera xanthii*) (Px) | 9-present | 1-absent | 9-present | 9-present |
| 47 | VG/VS Resistance to Downy mildew (*Pseudoperonospora cubensis*)(Pcu) | 1-absent | 1-absent | 1-absent | 1-absent |

TABLE 1-continued

| Variety Descriptive Information | | | | | |
|---|---|---|---|---|---|
| | Trait | 'HRZ-CS-24-0001H' | 'HRZ-CS-24-0003L' | 'HRZ-CS-24-0004L' | 'Qwerty' |
| 48 | VG/VS Resistance to Corynespora blight and target leaf spot (*Corynespora cassiicola*)(Cca) | 1-absent | 1-absent | 1-absent | 1-absent |
| 49 | VG/VS Resistance to Cucumber vein yellowing virus (CVYV) | 9-present | 1-absent | 9-present | 9-present |
| 50 | VG/VS Resistance to Zucchini yellow mosiac virus (ZYMV) | 1-absent | 1-absent | 1-absent | 1-absent |
| 51 | VG/VS Resistance to Cucurbit yellow stunting disorder virus (CYSDV) | 1-absent | 1-absent | 1-absent | 1-absent |

As shown in Table 1 above, 'HRZ-CS-24-0001H' as well as parental lines 'HRZ-CS-24-0003L' and 'HRZ-CS-24-0004L' have shorter internode lengths than 'Qwerty' (very short vs short). The average internode length of 'HRZ-CS-24-0001H', 'HRZ-CS-24-0003L' and 'HRZ-CS-24-0004L' is 2.64 cm, 2.12, 2.5 cm, respectively, whereas the average internode length of 'Qwerty' is 3.94 cm. 'HRZ-CS-24-0001H' and parental lines 'HRZ-CS-24-0003L' and 'HRZ-CS-24-0004L' also produce more flowers per node, with predominantly more than five flowers per node compared to 'Qwerty', which produces one or two flowers per node.

Figure 2A:
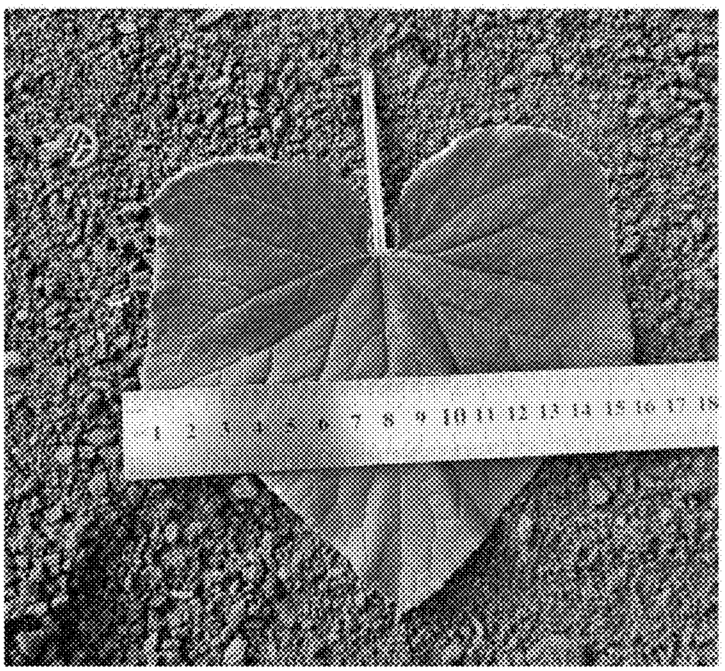
FIGS. 2A-FIG. 2B are photographs of the leaves of 'HRZ-CS-24-0001H'.
Figure 2B:
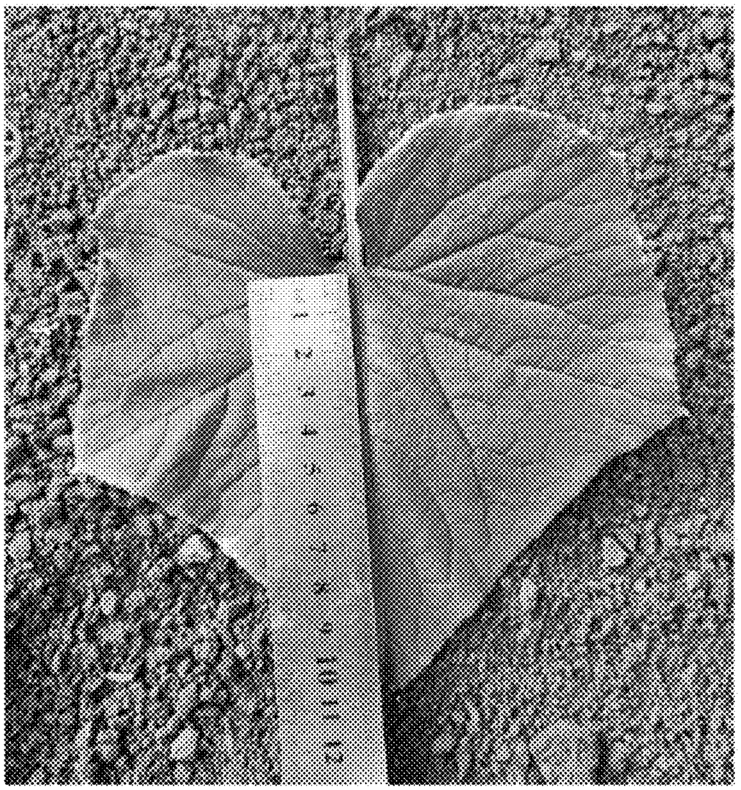
Figure 3:
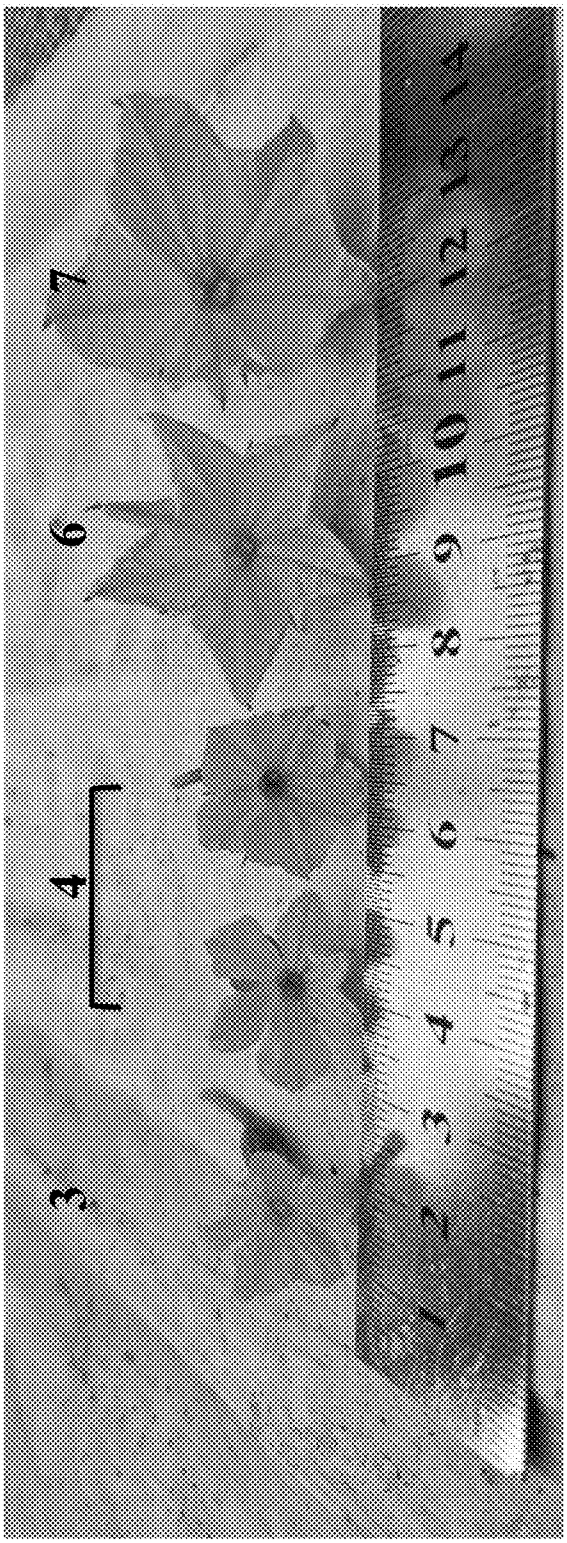
FIG. 3 is a photograph of female flowers of various cucumber varieties and their scores (1-9). Variety 'HRZ-CS-24-0001H' has very small flowers that consistently score a 3.
Figure 4A:
FIG. 4A and FIG. 4B are photographs of prime cucumber fruit of hybrid variety 'HRZ-CS-24-0001H' showing the length of the fruit (FIG. 4A) and the diameter of the fruit (FIG. 4B).
Figure 4B:
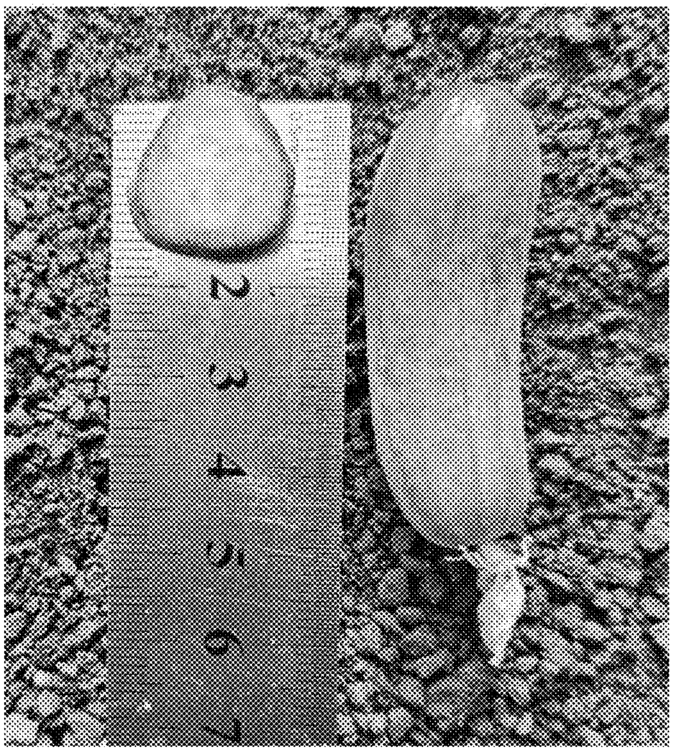
Figure 4C:
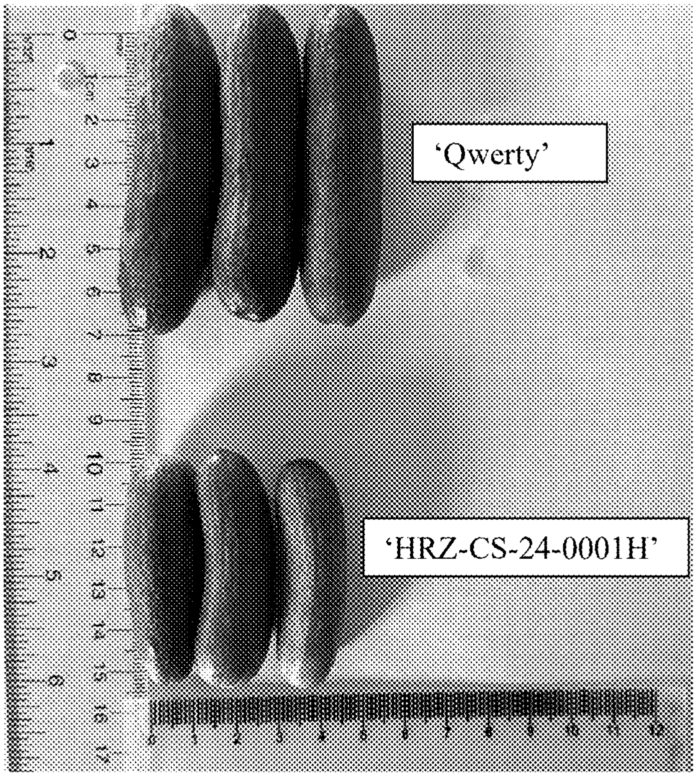
FIG. 4C is a photograph of cucumber fruits of commercial variety 'Qwerty' (top) and fruits of variety 'HRZ-CS-24-0001H' (bottom), when grown under the same conditions and harvested at prime for each variety.

As noted in Table 1 above, hybrid cucumber variety 'HRZ-CS-24-0001H' has smaller leaves than 'competitor variety 'Qwerty' (see also FIGS. 2A-2B). Hybrid cucumber variety 'HRZ-CS-24-0001H' also has smaller female flowers than other cucumber varieties (FIG. 3, compare first flower on the left from 'HRZ-CS-24-0001H' which scores a "3" to other varieties). FIGS. 4A-4C show the length (FIG. 4A) and diameter (FIG. 4B) of fruits of 'HRZ-CS-24-0001H' and compared to fruits of commercial variety 'Qwerty' (FIG. 4C), when grown under the same conditions and harvested at prime for each variety. 'Together, the smaller flowers and shorter internodes mean that 'HRZ-CS-24-0001H', and parental lines 'HRZ-CS-24-0003L' and 'HRZ-CS-24-0004L', produce more fruit per plant, and smaller fruits, compared to 'Qwerty'.

Table 2A below compares some additional qualities of hybrid cucumber variety 'HRZ-CS-24-0001H' and inbred lines 'HRZ-CS-24-0003L' and 'HRZ-CS-24-0004L' to commercial hybrid cucumber variety 'Quete'. While 'HRZ-CS-24-0001H' is similar to hybrid cucumber plant 'Quete', there are significant differences including the harvest period, weight of fruit, and overall plant yield. The fruits of the plants of the present disclosure were harvested and measured on average of 10 days post-anthesis (ranging from 8 to 12 days). Anthesis as used herein is the stage of complete flower opening.

Yield was measured as total kilograms of fruit picked from May 19, 2024-Jul. 9, 2024 from 325 plants of 'HRZ-CS-24-0001H' and 325 plants of 'Quete' planted at a density of approximately 4.2 $m^2$ on 77 $m^2$.

The cucumbers were harvested at prime for each variety, meaning the fruits of 'HRZ-CS-24-0001H' were between 5-6 cm in length, and the fruits of 'Quete' were between 6-8 cm in length.

TABLE 2A

| Fruit Descriptive Information | | | | |
|---|---|---|---|---|
| Characterisitic | 'HRZ-CS-24-0001H' | 'HRZ-CS-24-0003L' | 'HRZ-CS-24-0004L' | 'Quete' |
| Prime fruit length | 4.0-6.5 cm | 4.0-5.0 cm | 5.0-6.5 cm | 6.0-8.0 cm |
| Prime fruit diameter | 1.1-1.5 cm | 1.1-1.5 cm | 1.1-1.5 cm | 1.5-2.0 cm |
| Prime fruit weight | 9.0-13.0 grams | 7.0-10.0 grams | 10.0-13.0 grams | 11.0-15.0 grams |
| Prime fruit self life 10 days post harvest | 0% loss | 0% loss | 0% loss | 0% loss |
| Yield* | 902.39 kg/11.71 kg per $m^2$ | | | 809.31 kg/10.5 kg per $m^2$ |
| Picking speed | 278 grams/minute | | | 237 grams/minute |
| Prime fruit color | RHS 140 C, slightly lighter green than 'Quete' | | | Slightly darker green than 'HRZ-CS-24-0001H' |
| Harvest period | About 12 weeks | About 12 weeks | About 12 weeks | 4 weeks shorter than 'HRZ-CS-24-0001H' |

Figure 5A:
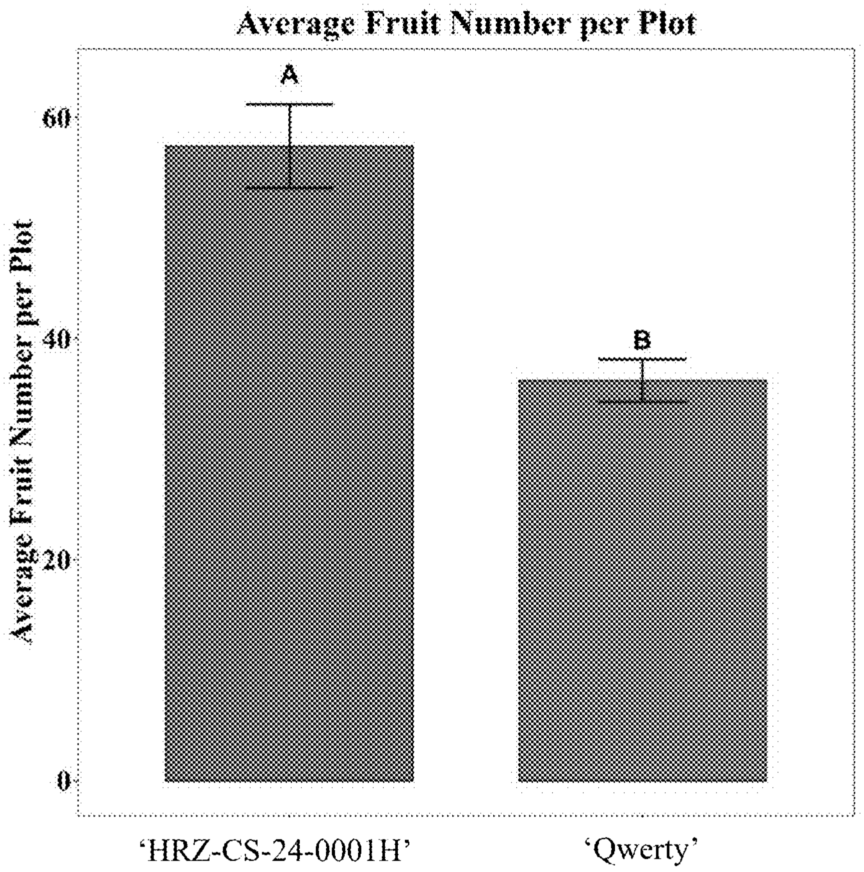
FIG. 5A is a bar graph of the average number of fruits per plot (three plots of 7 plants each) for 'HRZ-CS-24-0001H' and 'Qwerty'.
Figure 5B:
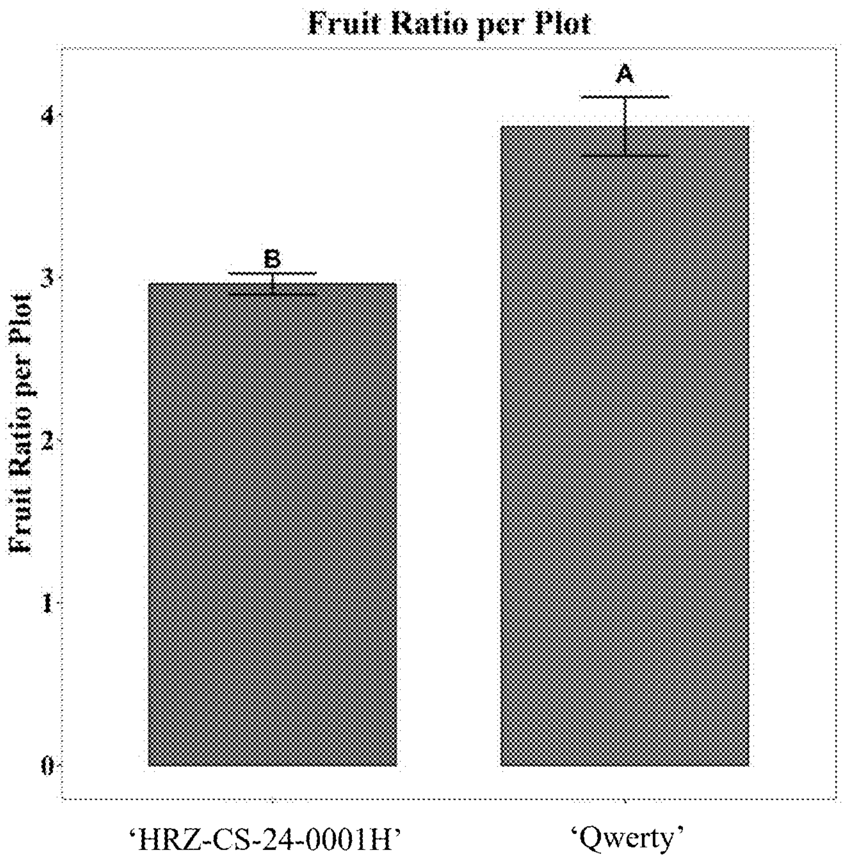
FIG. 5B is a bar graph of the fruit ratio per plot (three plots of 7 plants each) for 'HRZ-CS-24-0001H' and 'Qwerty'.

Table 2B summarizes comparative fruit characteristics and yield for 'HRZ-CS-24-0001H' and 'Qwerty'. Each variety was evaluated across three plots, with seven plants per plot. Plots of 'HRZ-CS-24-0001H' and 'Qwerty' were harvested every second day when fruits were 5 cm. At each harvest, all fruits were counted and weighed to determine the total fruit number and total fruit weight per plot. In addition, five representative fruits per plot were measured for length and diameter, and the fruit ratio (fruit length/fruit diameter) was subsequently calculated (Table 2B, see also FIGS. 5A-5B).

TABLE 2B

| Fruit characteristics and yield data | | |
|---|---|---|
| | 'HRZ-CS-24-0001H' | 'Qwerty' |
| No. of plots | 3 | 3 |
| No. of plants per plot | 7 | 7 |

TABLE 2B-continued

| Fruit characteristics and yield data | | |
|---|---|---|
| | 'HRZ-CS-24-0001H' | 'Qwerty' |
| Average fruits per plot | 57.4 ± 3.8 | 36.2 ± 1.9 |
| No. of tested fruits per plot | 20 | 20 |
| Average fruit length per plot (cm) | 5 ± 0.01 | 5 ± 0.01 |
| Average fruit diameter per plot | 1.69 ± 0.04 | 1.28 ± 0.05 |
| Average fruit ratio per plot (L/D) | 2.9 ± 0.06 | 3.9 ± 0.1 |
| Average fruit weight per plot (g) | 9.5 ± 0.3 | 6 ± 0.7 |

The average number of fruits per plot was significantly higher for 'HRZ-CS-24-0001H' (57.4±3.8) compared to 'Qwerty' (36.2±1.9). 'HRZ-CS-24-0001H' exhibited a greater average fruit diameter (1.69±0.04 cm) than 'Qwerty' (1.28±0.05 cm). Consequently, the length-to-diameter ratio differed markedly, with 'HRZ-CS-24-0001H' showing a ratio of 2.9±0.06 and 'Qwerty' showing a higher ratio of 3.9±0.1, indicating that 'Qwerty' fruits are more elongated. Average fruit weight per plot was also higher for 'HRZ-CS-24-0001H' (9.5±0.3 g) compared to 'Qwerty' (6±0.7 g). These data demonstrate that when fruit was harvested at 5 cm in length, 'HRZ-CS-24-0001H' produces a greater number of fruits with larger diameter and higher weight, while 'Qwerty' fruits are more slender.

Soluble solids were also measured and compared for 'HRZ-CS-24-0001H' and 'Qwerty' (Table 2C). Fruits were harvested and Brix measured when 'HRZ-CS-24-0001H' and 'Qwerty' fruits reached 5 cm in length. 'Qwerty' fruit Brix was also measured on fruits between 8-9 cm in length (the commercial size). 40 fruits, collected from independent plants across multiple field plots to ensure biological replication and minimize plot-specific effects, were measured. Brix was measured using a calibrated digital refractometer (Atago co., ltd.) following manufacturer's instructions. Calibration was performed immediately prior to measurement. Mean Brix values among treatments were statistically compared using a Student's t-test to evaluate differences in soluble solids content between 'HRZ-CS-24-0001H' and 'Qwerty'.

TABLE 2C

| Brix levels and dry matter | | | | | | |
|---|---|---|---|---|---|---|
| Variety | Fruit length (cm) | No. of fruit | Av. Brix | Replicates | Weight per replicate (g) | Av. dry matter (%) |
| 'HRZ-CS-24-0001H' | 5 | 40 | 2 ± 0.05 | 3 | 200 | 4.34 ± 0.01 |
| 'Qwerty' | 5 | 40 | 1.27 ± 0.05 | 3 | 200 | 3.79 ± 0.01 |
| 'Qwerty' | 8 | 40 | 1.95 ± 0.05 | 3 | 200 | 3.76 ± 0.09 |

Figure 6A:
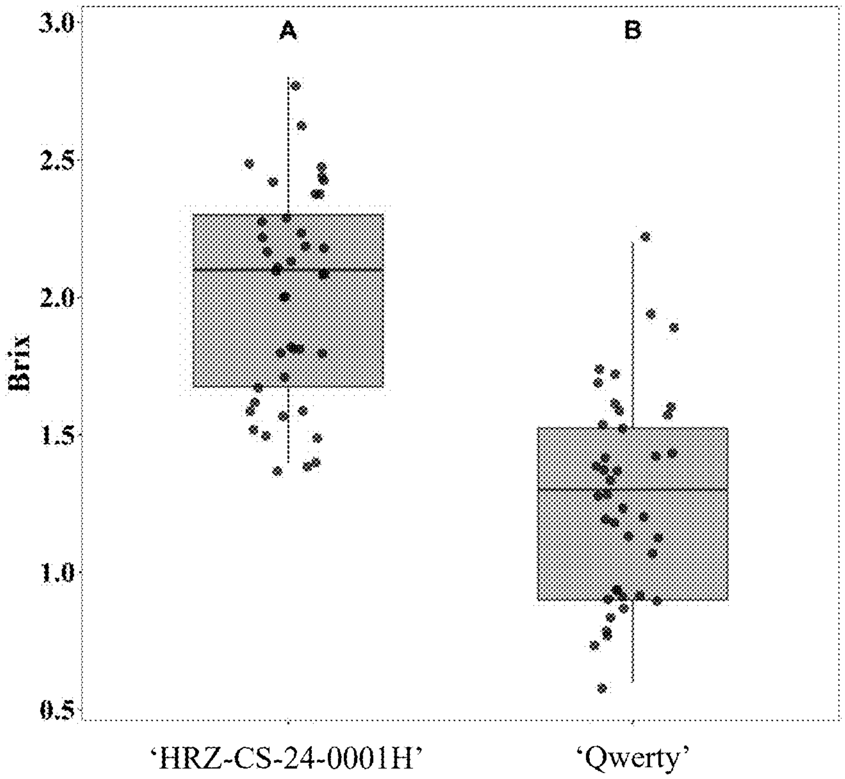
FIG. 6A is a comparative analysis of soluble solids content (measured as Brix) between 'HRZ-CS-24-0001H' and 'Qwerty', each evaluated when the fruit measured 5 cm in length and shown as box-plots with individual data points overlaid.
Figure 6B:
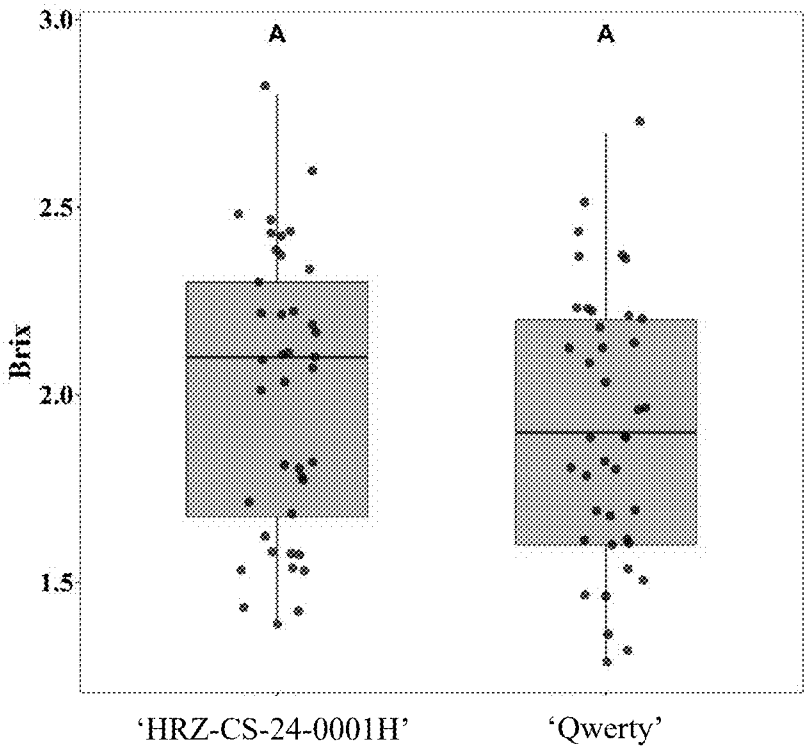
FIG. 6B is a comparative analysis of soluble solids content (measured as Brix) between 'HRZ-CS-24-0001H' and 'Qwerty', evaluated when fruit was considered prime-5 cm in length in for 'HRZ-CS-24-0001H' and 8 cm in length for 'Qwerty'. The data is shown as box-plots with individual data points overlaid.

As shown above in Table 2C and shown in FIG. 6A, the median Brix value for 'HRZ-CS-24-0001H' when harvested at 5 cm was approximately 2.0, with an interquartile range spanning roughly 1.8 to 2.3. Individual data points show a distribution primarily between 1.4 and 2.8 (FIG. 6A). In contrast, the median Brix value for 'Qwerty' when harvest at 5 cm was approximately 1.3, with an interquartile range from about 1.0 to 1.6. Data points are distributed between 0.6 and 2.2 (FIG. 6A). However, when 'Qwerty' is harvested at prime (8 cm), the median Brix value is about 2.0, with a range of between 1.3 and 2.7 (FIG. 6B). The comparison demonstrates that the 'HRZ-CS-24-0001H' variety is at prime and ready for harvest when fruits are only 5 cm in length. "Qwerty' fruits only reach similar Brix values when they are about 8 cm in length.

Figure 7A:
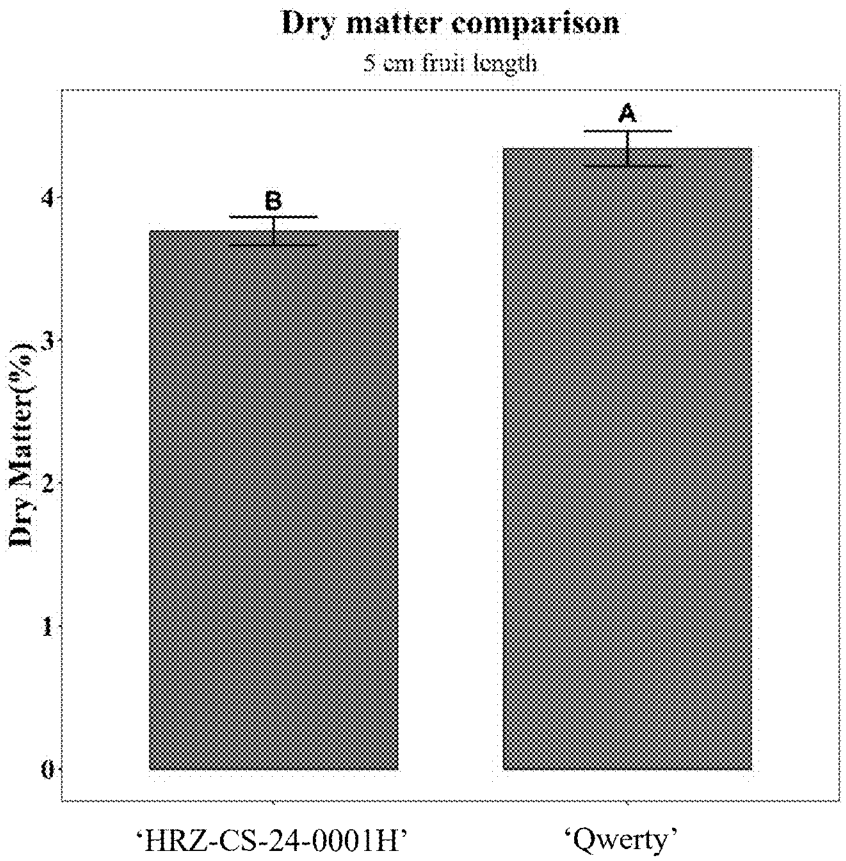
FIG. 7A is a bar graph showing the average dry matter percentage in cucumber fruits of 'HRZ-CS-24-0001H' and 'Qwerty' when harvested at approximately 5 cm in length.
Figure 7B:
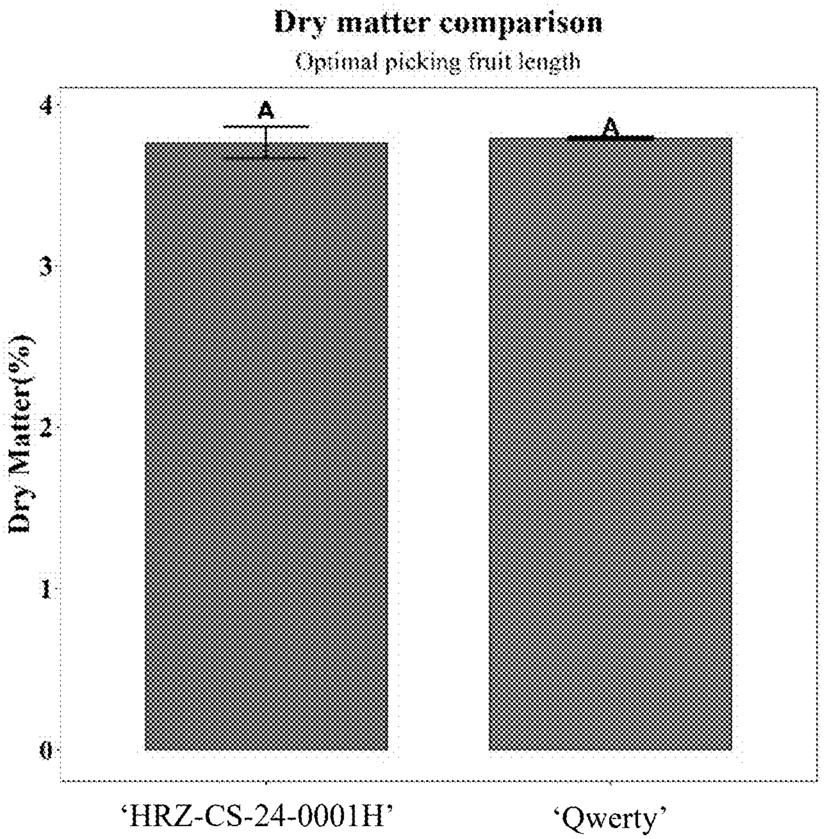
FIG. 7B is a bar graph showing the average dry matter percentage in cucumber fruits of 'HRZ-CS-24-0001H' and 'Qwerty' when at prime (approximately 5 cm in length for 'HRZ-CS-24-0001H' and approximately 8 cm in length for 'Qwerty').

FIG. 7A-7B illustrate a comparison of dry matter content between 'HRZ-CS-24-0001H' and 'Qwerty'. When cucumber fruits from both varieties are harvested at approximately 5 cm in length, 'Qwerty' exhibits a significantly higher dry matter percentage (approximately 4.3%) compared to 'HRZ-CS-24-0001H' (approximately 3.8%). In contrast, when 'Qwerty' fruit is harvest at prime (8 cm), there is no statistically significant difference in dry matter (FIG. 7B). These results further demonstrate that the optimal harvest time, or prime picking stage for 'HRZ-CS-24-0001H' is when fruits are approximately 5 cm in length. Dry matter analysis was performed by external certified laboratory (E. H. Smoler Consulting, Research for Agricultural Science Ltd., P.O.B. 283, Gadera, Israel 70752) and calculated as: Dry Matter (%)=(Fresh weight/(Fresh weight−Dry weight))×100.

In some embodiments, the prime cucumber fruit of the cucumber varieties described herein is between about 4.0 cm and about 6.5 cm in length. In some embodiments, the prime cucumber fruit of the cucumber varieties described herein is between about 5.0 cm and about 6.0 cm in length. In some embodiments, the prime cucumber fruit of the cucumber varieties described herein is between about 4.1 cm and about 6.4 cm, between about 4.2 cm and about 6.3 cm, between about 4.3 cm and about 6.2 cm, between about 4.4 cm and about 6.1 cm, between about 4.5 cm and about 6.0 cm, between about 4.6 cm and about 5.9 cm, between about 4.7 cm and about 5.8 cm, between about 4.8 cm and about 5.7 cm, between about 4.9 cm and about 5.6 cm, or between about 5.0 cm and about 5.5 cm.

In some embodiments, the prime cucumber fruit of the cucumber varieties described herein is between approximately 4.0 cm and approximately 6.5 cm in length. In some embodiments, the prime cucumber fruit of the cucumber varieties described herein is between approximately 5.0 cm and approximately 6.0 cm in length. In some embodiments, the prime cucumber fruit of the cucumber varieties described herein is between approximately 4.1 cm and approximately 6.4 cm, between approximately 4.2 cm and approximately 6.3 cm, between approximately 4.3 cm and approximately 6.2 cm, between approximately 4.4 cm and approximately 6.1 cm, between approximately 4.5 cm and approximately 6.0 cm, between approximately 4.6 cm and approximately 5.9 cm, between approximately 4.7 cm and approximately 5.8 cm, between approximately 4.8 cm and approximately 5.7 cm, between approximately 4.9 cm and approximately 5.6 cm, or between approximately 5.0 cm and approximately 5.5 cm.

In some embodiments, the prime cucumber fruit of the cucumber varieties described herein has a diameter of between about 1.0 cm and about 2.5 cm. In some embodiments, the prime cucumber fruit of the cucumber varieties described herein has a diameter of between about 1.1 cm and about 2.4 cm, between about 1.2 cm and about 2.3 cm, between about 1.3 cm and about 2.2 cm, between about 1.4 cm and about 2.1 cm, or between about 1.5 cm and about 2.0 cm. In some embodiments, the prime cucumber fruit of the cucumber varieties described herein has a diameter of between about 1.0 cm and about 2.0 cm. In some embodiments, the prime cucumber fruit of the cucumber varieties described herein has a diameter of between about 1.1 cm and about 1.5 cm.

In some embodiments, the prime cucumber fruit of the cucumber varieties described herein has a diameter of between approximately 1.0 cm and approximately 2.5 cm. In some embodiments, the prime cucumber fruit of the cucumber varieties described herein has a diameter of between approximately 1.1 cm and approximately 2.4 cm, between approximately 1.2 cm and approximately 2.3 cm, between approximately 1.3 cm and approximately 2.2 cm, between approximately 1.4 cm and approximately 2.1 cm, or between approximately 1.5 cm and approximately 2.0 cm. In some embodiments, the prime cucumber fruit of hybrid cucumber variety ‘HRZ-CS-24-0001H’ has a diameter of between approximately 1.0 cm and approximately 2.0 cm.

In some embodiments, the prime cucumber fruit of the cucumber varieties described herein has a length to diameter ratio of about 2.9. In some embodiments, the prime cucumber fruit of the cucumber varieties described herein has a length to diameter ratio of between about 2.5 to about 3.3. In some embodiments, the prime cucumber fruit of the cucumber varieties described herein has a length to diameter ratio of about 2.5, about 2.6, about 2.7, about 2.8, about 2.9, about 3.0, about 3.1, about, 3.2, or about 3.3. In some embodiments, the prime cucumber fruit of the cucumber varieties described herein has a length to diameter ratio of less than 4.

In some embodiments, the prime cucumber fruit of the cucumber varieties described herein has a weight of between about 7.0 grams and about 13.0 grams. In some embodiments, the prime cucumber fruit of the cucumber varieties described herein has a weight of between about 10.0 grams and about 13.0 grams, between about 11.0 grams and about 13.0 grams, or between about 7.0 grams and about 10.0 grams.

In some embodiments, the prime cucumber fruit of the cucumber varieties described herein has a weight of between approximately 9.0 grams and approximately 13.0 grams. In some embodiments, the prime cucumber fruit of the cucumber varieties described herein has a weight of between approximately 10.0 grams and approximately 12.0 grams, between approximately 11.0 grams and approximately 13.0 grams, or between approximately 9.0 grams and approximately 11.0 grams.

In some embodiments, the cucumber varieties described herein have an average internode length of about 2.6 cm. In some embodiments, the cucumber varieties described herein have an average internode length of between about 2.0 cm to about 3.3 cm. In some embodiments, the average internode length of the cucumber varieties described herein is about 2.1 cm, about 2.2 cm, about 2.3 cm, about 2.4 cm, about 2.5 cm, about 2.6 cm, about 2.7 cm, about 2.8 cm, about 2.9 cm, about 3.0 cm, about 3.1 cm, about, 3.2 cm, or about 3.3 cm. In some embodiments, the average internode length of the cucumber varieties described herein is less than 4.7 cm.

In some embodiments, the cucumber varieties described herein produce more fruits compared to similar commercial varieties grown under the same conditions. In some embodiments, the cucumber varieties described herein have an increase in the number of cucumber fruits of at least 10%, at least 20%, at least 30%, at least 40%, at least 50%, at least 60%, at least 70%, at least 80%, or at least 90% when compared to a similar commercial variety grown under the same conditions.

In some embodiments, the cucumber varieties described herein have an increase in the number of cucumber fruits of between about 10% and about 90% when compared to a similar commercial variety grown under the same conditions. In some embodiments, the cucumber varieties described herein have an increase in the number of cucumber fruits of between about 10% and about 90%, between about 10% and about 80%, between about 10% and about 70%, between about 10% and about 60%, between about 10% and 50%, or between about 50% and about 90%, when compared to a similar commercial variety grown under the same conditions.

In some embodiments, the cucumber varieties described herein have an extended harvest period compared to similar commercial varieties grown under the same conditions. In some embodiments, the harvest period is extended at least 2 weeks, at least 3 weeks, at least 4 weeks, at least 5 weeks, or at least 6 weeks beyond that of a similar variety grown under the same conditions. In some embodiments, the harvest period of the cucumber varieties described herein is extended between about 2 to about 6 weeks beyond that of a similar variety grown under the same conditions.

Cucumber fruits can be distinguished based on a number of additional parameters, for example volatile organic compounds content, total soluble solids, dry matter content, ascorbic acid, acidity, and flavor quality.

i. Volatile Organic Compounds

The cucumber fruit has at least 163 different volatile organic compounds (VOCs) that contribute to flavor, including amines, alcohols, aromatic compounds, phenolics, sulfur compounds, halogenated hydrocarbons, aldehydes, acid, terpenoid substances, hydrocarbons, ketones, heterocyclic compounds, and esters. VOCs can be grouped into three categories: 1) terpenoids, 2) phenylpropanoids or benzenes, and 3) alcohols or aldehydes. Example VOCs found in commercial cucumber varieties are shown below in Table 3, adapted from Zhang J. et al., Characterization of differences in composition and content of volatile compounds in cucumber fruit, *Foods* 2022, 11.

TABLE 3

Cucumber VOCs

| Compound | Formula | Class |
|---|---|---|
| Caryophyllene oxide | $C_{15}H_{24}O$ | Terpenoids |
| 1-Nonanol | $C_9H_{20}O$ | Alcohol |
| trans,cis-2,6-Nonadien-1-ol | $C_9H_{16}O$ | Alcohol |
| 1-Decanol | $C_{10}H_{22}O$ | Alcohol |
| 3,6-Nonadien-1-ol, (E,Z)- | $C_9H_{16}O$ | Alcohol |
| trans-2-Dodecen-1-ol | $C_{12}H_{24}O$ | Alcohol |
| Phenol | $C_6H_6O$ | Aromatics |

TABLE 3-continued

| Cucumber VOCs | | |
|---|---|---|
| Compound | Formula | Class |
| trans-alpha-Bergamotene | C15H24 | Hydrocarbons |
| Furan, 2-pentyl- | C9H14O | Heterocyclic compound |
| Pyrazine, 3,5-diethyl-2-methyl- | C9H14N2 | Heterocyclic compound |
| Quinoxaline, 2-methyl- | C9H8N2 | Heterocyclic compound |
| alpha-Cadinol | C15H26O | Terpenoids |
| Hexanal | C6H12O | Aldehyde |
| 2-Hexenal, (E)- | C6H10O | Aldehyde |
| 2-Heptenal, (E)- | C7H12O | Aldehyde |
| 2,4-Heptadienal, (E,E)- | C7H10O | Aldehyde |
| Nonanal | C9H18O | Aldehyde |
| 2-Nonenal, (E)- | C9H16O | Aldehyde |
| 2,6-Nonadienal, (E,Z)- | C9H14O | Aldehyde |
| Decanal | C10H20O | Aldehyde |
| 2,4-Nonadienal, (E,E)- | C9H14O | Aldehyde |
| 2,4-Decadienal, (E,E)- | C10H16O | Aldehyde |
| Undecanal | C11H22O | Aldehyde |
| 2-Undecenal | C11H20O | Aldehyde |
| Dodecanal | C12H24O | Aldehyde |
| Tetradecanal | C14H28O | Aldehyde |
| Pentadecanal | C15H30O | Aldehyde |
| Hexadecanal | C16H32O | Aldehyde |
| 1-Hepten-3-one | C7H12O | Ketone |
| 3-Octen-2-one | C8H14O | Ketone |
| 3,5-Octadien-2-one | C8H12O | Ketone |
| Tetradecane | C14H30 | Hydrocarbons |
| Pentadecane | C15H32 | Hydrocarbons |
| Hexadecane | C16H34 | Hydrocarbons |
| Heptadecane | C17H36 | Hydrocarbons |
| Eicosane | C20H42 | Hydrocarbons |
| Heneicosane | C21H44 | Hydrocarbons |
| 1-Dodecanol | C12H26O | Alcohol |
| Benzenepropanoic acid, ethyl ester | C11H14O2 | Ester |
| 5-Oxotetrahydrofuran-2-carboxylic acid, ethyl ester | C7H10O4 | Ester |
| Hexadecanoic acid, methyl ester | C17H34O2 | Ester |
| 5-Ethylcyclopent-1-enecarboxaldehyde | C8H12O | Aldehyde |
| 2(4H)-Benzofuranone, 5,6,7,7a-tetrahydro-4,4,7a-trimethyl-, (R)- | C11H16O2 | Ester |
| 6-Nonenal, (Z)- | C9H16O | Aldehyde |
| Benzaldehyde, 2-ethyl- | C9H10O | Aldehyde |
| 6-Nonen-1-ol, (E)- | C9H18O | Alcohol |
| cis-2-(2-Pentenyl)furan | C9H12O | Heterocyclic compound |
| 5,9-Undecadien-2-one, 6,10-dimethyl- | C13H22O | Ketone |
| 1,7-Nonadiene, 4,8-dimethyl- | C11H20 | Hydrocarbons |
| Pentadecane, 2,6,10-trimethyl- | C18H38 | Hydrocarbons |
| 1-Pentanone, 1-(4-methylphenyl)- | C12H16O | Ketone |
| Benzaldehyde, 3-ethyl- | C9H10O | Aldehyde |
| 3-Cyclohexene-1-acetaldehyde, alpha,4-dimethyl- | C10H16O | Aldehyde |
| 2,2'-Ethylidenebis(5-methylfuran) | C12H14O2 | Heterocyclic compound |
| 3a,7-Methano-3aH-cyclopentacyclooctene, 1,4,5,6,7,8,9,9a-octahydro-1,1,7-trimethyl-, [3aR-(3a alpha, 7 alpha,9a beta)]- | C15H24 | Terpenoids |
| alpha-Dehydro-ar-himachalene | C15H20 | Terpenoids |
| (1R,4S,9aS)-1-Methyl-4-((Z)-pent-2-en-4-yn-1-yl)octahydro-1H-quinolizine | C15H23N | Heterocyclic compound |
| Isopropyl myristate | C17H34O2 | Ester |
| Bicyclo[5.2.0]nonane, 2-methylene-4,8,8-trimethyl-4-vinyl- | C15H24 | Terpenoids |
| 1,4,7,-Cycloundecatriene, 1,5,9,9-tetramethyl-, Z,Z,Z- | C15H24 | Hydrocarbons |
| Phenol, 4-(1-phenylethyl)- | C14H14O | Phenol |
| Cyclohexanol, 2,6-dimethyl- | C8H16O | Alcohol |
| Cyclohexene, 4-methyl-1-(1-methylethenyl)- | C10H16 | Hydrocarbons |
| Tetradecane, 2-methyl- | C15H32 | Hydrocarbons |
| Phytol, acetate | C22H42O2 | Alcohol |
| 1-Pyridineethanamine, beta-(2-furanyl)hexahydro- | C11H18N2O | Heterocyclic compound |
| Undecane, 3,8-dimethyl- | C13H28 | Hydrocarbons |
| D-Alanine, N-propargyloxycarbonyl-, propargyl ester | C10H11NO4 | Ester |
| 1,3-Benzenediol, 5-pentyl- | C11H16O2 | Phenol |
| 3,7,11, 15-Tetramethyl-2-hexadecen-1-ol | C20H40O | Terpenoids |
| (5R,8aR)-5-Propyloctahydroindolizine | C11H21N | Heterocyclic compound |
| Undecane, 5,7-dimethyl- | C13H28 | Hydrocarbons |
| Dimethyl phthalate | C10H10O4 | Ester |
| Naphthalene, 2-methyl- | C11H10 | Aromatics |
| Z-11-Tetradecenoic acid | C14H26O2 | Acid |
| Ethylamine, 2-diethylboryloxy- | C6H16BNO | Amine |
| 1-Hexen, 2-(p-anisyl)-5-methyl- | C14H20O | Hydrocarbons |
| Phenol, 4-propyl- | C9H12O | Phenol |
| Benzenamine, 2,6-diethyl- | C10H15N | Amine |
| Hordenine | C10H15NO | Amine |

TABLE 3-continued

| Cucumber VOCs | | |
|---|---|---|
| Compound | Formula | Class |
| 1,8,11,14-Heptadecatetraene, (Z,Z,Z)- | C17H28 | Hydrocarbons |
| 9H-Fluoren-9-one | C13H8O | Aromatics |
| 2-Tetradecene, (E)- | C14H28 | Hydrocarbons |
| Piperazine | C4H10N2 | Heterocyclic compound |
| 1-Undecene, 9-methyl- | C12H24 | Hydrocarbons |
| 1-Penten-3-one, 4-methyl-1-(1-piperidinyl)- | C11H19NO | Ketone |
| Cyclobutanecarboxamide, N-(3-methylphenyl)- | C12H15NO | Amine |
| 3,5-Dihydroxy-4'-methoxydiphenyl | C13H12O3 | Alcohol |
| 1-Penten-3-one, 1-(4-methoxyphenyl)-4-methyl- | C13H16O2 | Ketone |
| 1-Alanine, N-(2,3,4-trifluorobenzoyl)-, methyl ester | C11H10F3NO3 | Ester |
| Dimethylphosphinic fluoride | C2H6FOP | Other |
| Isobutyl pent-4-enyl carbonate | C10H18O3 | Ester |
| (E)-Hex-3-enyl (E)-2-methylbut-2-enoate | C11H18O2 | Ester |
| Pyrimido[1,6-a]indole, 1,2,3,4-tetrahydro-2,5-dimethyl- | C13H16N2 | Heterocyclic compound |
| 1-Phenylcyclohexylamine | C12H17N | Amine |
| Benzene, 1,4-dimethoxy-2-methyl-5-isopropyl- | C12H18O2 | Aromatics |
| Bicyclo(3.3.1)non-2-ene | C9H14 | Hydrocarbons |
| Naphthalene, 1,2-dihydro-4,5,7-trimethyl- | C13H16 | Aromatics |
| Cobalt, bis(beta-5-piperidinylcyclopentadienyl)- | C20H28CoN2 | Heterocyclic compound |
| Benzoic acid, 3,4-dimethyl-, methyl ester | C10H12O2 | Ester |
| 2-Acetyl-3-methylbenzo[b]thiophene | C11H10OS | Heterocyclic compound |
| 3H-1,2,4-triazole-3-thione, 5-amino-2-ethyl-2,4-dihydro-4-methyl- | C5H10N4S | Heterocyclic compound |
| 1H-1,2,3-Triazole | C2H3N3 | Heterocyclic compound |
| Phosphorocyanidothioic difluoride | CF2NPS | Other |
| 1H-Pyrazole, 1,3,5-trimethyl- | C6H10N2 | Heterocyclic compound |
| 5-Azulenemethanol, 1,2,3,4,5,6,7,8-octahydro-alpha, alpha, 3,8-tetramethyl-, acetate, [3S-(3 alpha ,5.alpha, 8 alpha)]- | C17H28O2 | Ester |
| 1,3-Cyclohexadiene-1-carboxylic acid, 2,6,6-trimethyl-, ethyl ester | C12H18O2 | Ester |
| 1-chloro-3-diethylboryloxy-2,2-dimethyl-Propane | C9H20BClO | other |
| 5,6-diethyl-Cyclohexa-1,3-diene | C10H16 | Hydrocarbons |
| (E)-2-Butenoic acid, 2-(methylenecyclopropyl)prop-2-yl ester | C11H16O2 | ester |
| 2-Diethylamino-N-methyl-2-phenyl-acetamide | C13H20N2O | Nitrogen compounds |
| 2-Pentene-1,4-dione, 1-(1,2,2-trimethylcyclopentyl) | C13H20O2 | ketone |
| trans-2,4-Dimethylthiane, S,S-dioxide | C7H14O2S | Heterocyclic compound |
| Cyclohexyl propylphosphonofluoridate | C9H18FO2P | ester |
| 2,4,8-Trimethyl-1,2,3,4-tetrahydroquinoline | C12H17N | Heterocyclic compound |
| 4-(Benzyl-ethyl-amino)-butyric acid, methyl ester | C14H21NO2 | ester |
| Carbonic acid, propyl 4-cyanophenyl ester | C11H11NO3 | ester |
| 6-methyl-7-Oxa-8-azabicyclo[4.2.1]non-8-ene | C8H13NO | Heterocyclic compound |
| 4-fluoro-3-nitro-benzoic acid, 2,4-bis(1,1-dimethylpropyl)phenyl ester | C29H23NO | ester |
| 7-ethyl-2-methyl-4-benzoxazolol | C10H11NO2 | Heterocyclic compound |
| 4-Methylmercaptoaniline | C7H9NS | amine |
| Hexadecanoic acid, butyl ester | C20H40O2 | ester |
| 2,2,6,6-tetramethyl-3,5-Heptanedione | C11H20O2 | ketone |
| Cyclohexanepropanol | C9H18O | alcohol |
| 2,4-dimethyl-Quinoline | C11H11N | Heterocyclic compound |
| 2-(2-butoxyethoxy)-Ethanol,acetate | C10H20O4 | ester |
| 6-methyl-3(2H)-Pyridazinone | C5H6N2O | Heterocyclic compound |
| 1-amino-4,4-dimethyl-1-(3-pyridyl)-Pent-1-en-3-one | C12H16N20 | Heterocyclic compound |
| 1-bromo-3-methyl-Cyclohexane | C7H13Br | other |
| 1-(2-methyl-1-butenyl)-Pyrrolidine | C9H17N | Heterocyclic compound |
| o-Menth-8-ene | C10H18 | Terpenoids |
| Phosphoric acid, 2-chloroethenyl dimethyl ester | C4H8ClO4P | ester |
| 1,4-Dihydro-4-oxopyridazine | C4H4N2O | Heterocyclic compound |
| octyl-Cyclohexane | C14H28 | Hydrocarbons |
| decyl-Cyclohexane | C16H32 | Hydrocarbons |
| 9,9-dimethyl-Xanthene | C15H14O | Aromatics |
| 4-Hexyn-3-ol | C6H10O | alcohol |
| 2-(1,1-Dimethylethyl)-6-(1-methylethyl)phenol | C13H20O | phenol |
| (1R,2S)-(−)-2-Amino-1,2-diphenylethanol | C14H15NO | amine |
| 1,1'-(6-methoxy-2,5-benzofurandiyl)bis-Ethanone | C13H12O4 | Heterocyclic compound |
| 3,5,5-trimethyl-2-Hexene | C9H18 | Hydrocarbons |
| 6-methyl-2(1H)-Pyridone | C6H7NO | Heterocyclic compound |
| 3,4-diethyl-1H-Pyrrole-2,5-dione | C8H11NO2 | Heterocyclic compound |
| 2-bromo-1,1,3-trimethyl-Cyclopropane | C6H11Br | Halogenated hydrocarbons |
| 2-n-Butyl furan | C8H12O | Heterocyclic compound |
| 2,4-dihydroxy-6-methyl-Benzaldehyde | C8H8O3 | aldehyde |
| 4-acetyl-2,3,4,5,5-pentamethyl-2-Cyclopenten-1-one | C12H18O2 | ketone |
| Cyanogen bromide | CBrN | other |
| 2,4-Diamino-6-methyl-1,3,5-triazine | C4H7N5 | Heterocyclic compound |
| 1-iodo-Hexadecane | C16H33I | Halogenated hydrocarbons |
| 1-[6-hydroxy-2-(1-methylethenyl)-7-benzofuranyl]-Ethanone | C13H12O3 | Heterocyclic compound |
| (E)-5-(pentyloxy)-2-Pentene | C10H20O | Hydrocarbons |

TABLE 3-continued

| Cucumber VOCs | | |
|---|---|---|
| Compound | Formula | Class |
| (Z)-9,17-Octadecadienal | C18H32O | aldehyde |
| (R,S)-5-Ethyl-6-methyl-3E-hepten-2-one | C10H18O | ketone |
| 1-ethyl-6-ethylidene-Cyclohexene | C10H16 | Hydrocarbons |
| 4-methyl-1-Pentanol | C6H14O | alcohol |
| 1,4,6-Trimethyl-1,2,3,3a,4,7,8,8a-octahydro-4,7-ethanoazulene | C15H24 | Terpenoids |
| dl-2-benzylamino-1-Propanol | C10H15NO | alcohol |
| 1,4-dimethyl-2,3-Diazabicyclo[2.2.1]hept-2-ene | C7H12N2 | Heterocyclic compound |
| Sulfamide | H4N2O2S | Sulfur compounds |
| 2-ethyl-1,3-Cyclopentanedione | C7H10O2 | ketone |
| 4-(1,1-dimethyl-2-propynyloxy)-Toluene | C12H14O | Aromatics |
| 2,2',5,5'-tetrahydro-2,2'-Bifuran | C8H10O2 | Heterocyclic compound |

ii. Total Soluble Solids and Dry Matter Content

Typically measured in degrees Brix, but may also be presented as a percentage, total soluble solids (TSS) refers to the overall amount of dissolved substances present in the cucumber fruit juice, which mainly consists of sugars. Dry matter content (DMC) is usually measured as a percentage. Methods for determining DMC and TSS are known in the art. See for example, AOAC official method 920.151. Solids (total) in fruits and fruit products, *Official Methods of Analysis of AOAC International* (sixteenth ed. $5^{th}$) (1999). Briefly, for DMC, a whole cucumber is ground until homogenous, and a subsample of the mixture (g) is dried at 70° C. until the oscillations between two consecutive weight measurements (performed at 2-hour intervals) were <0.1%. Recent studies examining the TSS and DMC of cucumber suggest that higher contents of TSS and DMC may be useful indicators of cucumber shelf-life; the higher their contents, the longer the shelf-life (Valverde-Miranda D. et al., Total soluble solids and dry matter of cucumber as indicators of shelf-life, *Postharvest Biology and Technology* 2021, Vol. 180).

In some embodiments, the cucumber varieties described herein produce small cucumber fruits that when harvested at prime (i.e. about 5 cm in length) have at least 1° Brix. In some embodiments, the cucumber varieties described herein produce small cucumber fruits harvested at prime having between about 1.4 and about 2.8° Brix. In some embodiments, the cucumber varieties described herein produce small cucumber fruits harvested at prime having between 1.8 and 2.3° Brix, between 1.9 and 2.2° Brix, or between 2.0 and 2.1° Brix.

iii. Ascorbic Acid and Acidity

Ascorbic acid content and acidity can be measured by methods known in the art. For example, ascorbic acid (vitamin C) content can be determined using a redox titration with a color-changing dye (e.g. dichlorophenolindophenol) or by UV spectrophotometry. Ascorbic acid content may also be evaluated using high performance liquid chromatography. Estimation of acidity may be measured by titrating cucumber fruit juice with 0.1 N sodium hydroxide using phenolphthalein as an indicator and expressed as percent acidity.

Acidity (%)=Equivalent weight of acid×Normality of×Titre value NaOH/Weight of sample×100

(see for example, Kumar Reddy P. S. et al., Assessment of total soluble solids, ascorbic acid and acidity in cucumber (*Cucumis sativus* L.) varieties under open and protected conditions (2022) *Annals of Phytomedicine* 11(2): 684-688).

iv. Flavor Quality Evaluation

The flavor, sweetness, and astringency of cucumbers can also be measured by taste evaluation of consumers using a scale of 0-9, with 0 being odorless and 9 being the strongest. See for example, Zhang J. et al., Characterization of differences in composition and content of volatile compounds in cucumber fruit, *Foods* 2022, 11. In a consumer taste testing, cucumber fruits of 'HRZ-CS-24-0001H' received positive feedback for sweetness, crunch, overall taste, small size, and even appearance (Leamington Greenhouse Competition, Jun. 5-7, 2024, first place for cocktail cucumber category, available on the worldwide web at greenhousecompetitions.com/2024/06/11/2024-winners/.

Cucurbitacins are a group of triterpenoids found primarily in the Cucurbitaceae plant family and give the fruit a bitter taste. Thus, in some embodiments, the cucumber varieties described herein have a reduced cucurbitacin content compared to similar varieties grown and harvested under the same conditions, giving them an overall better taste that is more preferred by consumers.

Cucumber Breeding

The goal of cucumber breeding is to develop new, unique and superior cucumber inbred lines and hybrids. The breeder initially selects and crosses two or more parental lines, followed by repeated selfing and selection, producing many new genetic combinations. Another method used to develop new, unique and superior cucumber inbred lines and hybrids occurs when the breeder selects and crosses two or more parental lines followed by haploid induction and chromosome doubling that result in the development of dihaploid inbred lines. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions, and further selections are then made, during and at the end of the growing season. The inbred lines developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines the breeder develops, except possibly in a very gross and general fashion. This unpredictability results in the expenditure of large research monies to develop superior new cucumber inbred lines and hybrids.

The development of commercial cucumber hybrids requires the development of homozygous inbred lines, the crossing of these lines, and the evaluation of the hybrid crosses.

Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, inbred cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

For parthenocarpic (seedless) varieties, male flowers can be induced by application of chemicals, such as silver nitrate ($AgNO_3$), gibberellic acid ($GA_3$), silver thiosulphate ($Ag(S_2O_3)_2^{-3}$), 1-methylcyclopropene, and combinations thereof. In some embodiments, the chemical to induce male flowering is an agent inhibiting ethylene action, such as 1-methylcyclopropene, silver ions, 2-aminoethoxyvinyl glycine, pyrazinamide, and 2,5-norbornadiene. In some embodiments, the agent inhibiting ethylene action is selected from silver nitrate, silver thiosulfate, gibberellic acid, 1-methylcyclopropene, and combinations thereof. Additional methods and chemicals to induce male flower formation are well known in the art. See for example, Dhall R. et al., Standardized protocol for in situ and in vitro maintenance of newly developed parthenocarpic gynoecious cucumber inbred, *Brazilian Archives of Biology and Technology,* 2022 Vol. 65.

i. Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_{1s}$ or by intercrossing two Fis (sib mating). The dihaploid breeding method could also be used. Selection of the best individuals is usually begun in the $F_2$ population; then, beginning in the F3, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential use as parents of new hybrid cultivars. Similarly, the development of new inbred lines through the dihaploid system requires the selection of the best inbreds followed by two to five years of testing in hybrid combinations in replicated plots.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more fruit containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each fruit by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

ii. Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype recurrent parent and the trait of interest from the donor parent are selected and repeatedly crossed (backcrossed) to the recurrent parent. The resulting plant is expected to have the attributes of the recurrent parent (e.g., cultivar) and the desirable trait transferred from the donor parent.

When the term hybrid cucumber plant is used in the context of the present disclosure, this also includes any hybrid cucumber plant where one or more desired trait has been introduced through backcrossing methods, whether such trait is derived from a naturally occurring one, simultaneously or artificially-induced mutation, a transgenic one or a gene or a nucleotide sequence modified by the use of New Breeding Techniques. Backcrossing methods can be used with the present disclosure to improve or introduce one or more characteristic into the inbred parental line, thus potentially introducing these traits into the hybrid cucumber plant of the present disclosure. The term "backcrossing" as used herein refers to the repeated crossing of a hybrid progeny back to the recurrent parent, i.e., backcrossing one, two, three, four, five, six, seven, eight, nine, or more times to the recurrent parent. The parental cucumber plant which contributes the gene or the genes for the desired characteristic is termed the nonrecurrent or donor parent. This terminology refers to the fact that the nonrecurrent parent is used one time in the backcross protocol and therefore does not recur. The parental cucumber plant to which the gene or genes from the nonrecurrent parent are transferred is known as the recurrent parent as it is used for several rounds in the backcrossing protocol.

In a typical backcross protocol, the original inbred of interest (recurrent parent) is crossed to or by a second inbred (nonrecurrent parent) that carries the gene or genes of interest to be transferred. The resulting progeny from this cross are then crossed again to or by the recurrent parent and the process is repeated until a cucumber plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact, the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as cucumber leaf curl virus resistance in cucumber, requires selfing the progeny or using molecular markers to determine which plant carry the recessive allele(s).

Many desirable traits have been identified that are not regularly selected for in the development of a new parental inbred of a hybrid cucumber plant according to the disclosure but that can be improved by backcrossing techniques. Desirable traits may or may not be transgenic. Examples of these traits include but are not limited to, male sterility (such as a PR glucanase gene or the ms1, ms2, ms3, ms4 or ms5 genes), herbicide resistance or herbicide tolerance, (such as bar or PAT genes), gynoecia (such as the g gene), resistance for bacterial, fungal (genes Fom-1 and Fom-2 for resistance to *fusarium* wilt), powdery mildew resistance, or viral disease (gene nsv for resistance to melon necrotic spot virus, gene ZYM for the resistance to the zucchini yellow mosaic virus), pest resistance, insect resistance (gene Vat for resistance to *Aphis gossypii*), male fertility, environmental stress tolerance, delayed senescence, controlled ripening, modified carbohydrate metabolism, modified protein metabolism, enhanced nutritional quality, enhanced sugar content, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc., *Principles of Plant Breeding*). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly or essentially the same adaptation, yielding ability and quality characteristics of the recurrent parent but superior to that parent in the particular characteristic(s) for which the improvement program was undertaken. Therefore, this method provides the plant breeder with a high degree of genetic control of this work.

The method is scientifically exact because the morphological and agricultural features of the improved variety could be described in advance and because a similar variety could, if it were desired, be bred a second time by retracing the same steps (Briggs, "Breeding wheats resistant to bunt by the backcross method", 1930 *Jour. Amer. Soc. Agron.,* 22:289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be theoretically modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred or when using molecular markers that can identify the trait of interest.

The backcross technique is not only desirable when breeding for disease resistance but also for the adjustment of morphological characters, color characteristics and simply inherited quantitative characters such as earliness, plant height and seed size and shape.

iii. Open-Pollinated Populations

The improvement of open-pollinated populations of crops depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagated by random-mating within itself in isolation.

Second, the synthetic variety attains the same end result as population improvement, but is not itself propagated as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by intercrossing a number of genotypes selected for good combining ability in all possible hybrid combinations, with subsequent maintenance of the variety by open pollination. Whether parents are (more or less inbred) seed-propagated lines, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Hybrid commercial cucumber seed can be produced by controlled hand pollination. The male flowers from the male plants are harvested and used to pollinate the stigmatic surface of the female flowers on the female plants. Prior to, and after hand pollination, flowers are covered so that insects do not bring foreign pollen and create a mix or impurity. Flowers are tagged to identify pollinated fruit from which seed will be harvested.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor and uniformity exhibited by $F_1$ hybrids is lost in the next generation (F2). Consequently, seed from $F_2$ hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA,* 99:9828-9832) and Quarrie et al. (Quarrie et al., 1999, *Journal of Experimental Botany,* 50 (337): 1299-1306).

For BSA of a trait of interest, parental lines with certain different phenotypes are chosen and crossed to generate $F_2$, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. In some embodiments, the donor or recipient female parent line and the donor or recipient male parent line are planted in the same greenhouse. The inbred male parent can be planted earlier than the female parent to ensure adequate pollen supply at the pollination time. In some embodiments, the male parent and female parent can be planted at a ratio of 1 male parent to 4-10 female parents. The male parent may be planted at the top of the field for efficient male flower collection during pollination. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. In some embodiments, this process is best done in the afternoon. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked fruits are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Breeding of dioecious species can also be done by growing equal amount of each parent plant. Insects are placed in the field or greenhouses for transfer of pollen from the male parent to the female flowers of the female parent. In some embodiments, fruits set after the introduction of the beehives can be marked for later collection.

viii. Targeting Induced Local Lesions in Genomes (TILLING)

Breeding schemes of the present application can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and cucumber.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEco-TILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke a shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on

*Arabidopsis*; Southern Illinois University (USA), focusing on Soybean; John Innes Centre (UK), focusing on Lotus and *Medicago*; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus, in some embodiments, the breeding methods of the present disclosure include breeding with one or more TILLING plant lines with one or more identified mutations.

ix. Mutation Breeding

Mutation breeding is another method of introducing new variation and subsequent traits into cucumber plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques, also known as gene-editing techniques, such as the ones involving the uses of engineered nuclease to enhance the efficacy and precision of gene editing in combination with oligonucleotides including, but not limited to Zinc Finger Nucleases (ZFN), TAL effector nucleases (TALENs), chemical nucleases, meganucleases, engineered homing nucleases (such as endonucleases and meganucleases) and clustered regularly interspaced short palindromic repeats (CRISPR)-associated endonuclease Cas (CRISPR-Cas) system (using such as Cas9, Cas12a/Cpf1, Cas13/C2c2, CasX and CasY) shall also be used to generate genetic variability and introduce new traits into cucumber varieties.

x. Double Haploids and Chromosome Doubling

One way to obtain homozygous plants without the need to cross two parental lines followed by a long selection of the segregating progeny, and/or multiple backcrossing is to produce haploids and then double the chromosomes to form doubled haploids. Haploid plants can occur spontaneously, or may be artificially induced via chemical treatments or by crossing plants with inducer lines (Seymour et al. 2012, PNAS vol. 109, pg. 4227-4232; Zhang et al., 2008 Plant Cell Rep. December 27 (12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 µg. 63-72; Doubled Haploid Production in Crop Plants 2003 edited by Maluszynski ISBN 1-4020-1544-5). The production of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

In one aspect, the disclosure provides for a haploid plant and/or a doubled haploid plant of the varieties described herein, or of a plant having all but one, two, or three physiological or morphological characteristics of the varieties described herein, or progeny of said variety. Haploid and doubled haploid (DH) plants can, for example, be produced by cell or tissue culture and chromosome doubling agents and regeneration into a whole plant. In a method for DH production, chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for making doubled haploid cells of the varieties described herein, comprising making doubled haploid cells from haploid cells from the plant or plant part of the varieties described herein, with a chromosome doubling agent such as colchicine treatment (see, e.g., Nikolova and Niemirowicz-Szczytt (1996) Acta Soc Bot Pol 65:311-317).

In yet another aspect, the disclosure provides for haploid plants and/or doubled haploid plants derived from hybrid cucumber variety 'HRZ-CS-24-0001H' that, when combined, make a set of parents of hybrid cucumber variety 'HRZ-CS-24-0001H'. The haploid plant and/or the doubled haploid plant of variety 'HRZ-CS-24-0001H' can be used in a method for generating parental lines of hybrid cucumber variety 'HRZ-CS-24-0001H'.

In one aspect, the disclosure relates to a method of producing a combination of parental lines of the plant of variety 'HRZ-CS-24-0001H', comprising making doubled haploid cells from haploid cells from said plant or seed of that plant; and optionally crossing these parental lines to produce and collecting seeds. In another aspect, the disclosure relates to a combination of parental lines produced by this method. In still another aspect, the combination of parental lines can be used to produce a seed or plant of variety 'HRZ-CS-24-0001H' when these parental lines are crossed. In still another aspect, the disclosure relates to a combination of parental lines from which a seed or plant having all physiological and/or morphological characteristics of hybrid cucumber variety 'HRZ-CS-24-0001H' (when the numerical characteristics are determined at the 5% significance level and identical for non-numerical characteristics for plants grown under the same environmental conditions).

The disclosure also provides a method for producing parental lines for hybrid 'HRZ-CS-24-0001H' comprising: genetically characterizing a doubled haploid line from hybrid cucumber variety 'HRZ-CS-24-0001H' to determine whether one or more genetic markers are present in a first homozygous form or in a second homozygous form in said line, wherein one or more genetic markers are present in a heterozygous form in hybrid cucumber variety 'HRZ-CS-24-0001H'; and selecting at least one pair of doubled haploid lines that have complementary alleles for one or more genetic markers, wherein each member of the pair is suitable as a parental line for a hybrid organism, optionally this method further comprises defining a set of genetic markers present in a heterozygous form in hybrid cucumber variety 'HRZ-CS-24-0001H'; and producing doubled haploid lines from hybrid cucumber variety 'HRZ-CS-24-0001H'. Doubled haploid lines generated as described herein can be used in such method.

xi. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xii. Embryo Rescue

Alternatively, embryo rescue may be employed in the transfer of resistance-conferring genomic material from a donor plant to a recipient plant. Embryo rescue can be used as a procedure to isolate embryos from crosses to rapidly move to the next generation of backcrossing or selfing or wherein plants fail to produce viable seed. In this process, the fertilized ovary or immature seed of a plant is tissue cultured to create new plants (see Pierik, 1999*, In Vitro Culture of Higher Plants*, Springer, ISBN 079235267X, 978-0792352679, which is incorporated herein by reference in its entirety).

xii. Reverse Synthesis of Breeding Lines

A combination of a male and a female parental line of hybrid cucumber variety 'HRZ-CS-24-0001H' can also be generated, for example, through reverse synthesis of breeding lines.

Using methods known in the art such as "reverse synthesis of breeding lines" or "reverse breeding," it is possible to produce parental lines for a hybrid plant such as hybrid cucumber variety 'HRZ-CS-24-0001H'. A skilled person can take any individual heterozygous plant, such as hybrid cucumber variety 'HRZ-CS-24-0001H' and generate a combination of parental lines (reverse breeding parental lines) that, when crossed, produce the variety 'HRZ-CS-24-0001H'. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US 2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., hybrid cucumber variety 'HRZ-CS-24-0001H'), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

Gene Editing/Genome Editing

Gene editing (or Genome editing) technologies. Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENS, CRISPR, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring cucumber plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENS are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450,471; 8,586,526; 8,586,363; 8,592,645;

8,697,853; 8,704,041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et.al., Nat Rev Microbiol. 2011 May 9; 9 (6): 467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 μg 7, each of which is hereby incorporated in its entirety for all purposes.

Plant Transformation

Cucumber plants of the present disclosure can be further modified by introducing one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 U.S. application No. 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631 (1990), U.S. Pat. Nos. 4,795,855, 5,378,824 and 6,107,549). In addition, the dhfr gene, which confers resistance to the anticancer agent methotrexate, has been used for selection (Bourouis et al., *EMBO J.* 2 (7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General genetic transformation methods, and specific methods for transforming cucumber are well known in the art. For example, Nanasato Y, and Tabei Y. A method of transformation and current progress in transgenic research on cucumbers and *Cucurbita* species. *Plant Biotechnol* (Tokyo). 2020 Jun. 25; 37(2): 141-146; Yin Z., et al., Cucumber transformation methods—the review, *Bio Technologia* (2005) 1(68); Tan J. et al., Recent Progress in the Regeneration and Genetic Transformation System of Cucumber, *Appl. Sci.* (2022) 12(14); Fan Y. et al., A fast, simple, high efficient and one-step generation of composite cucumber plants with transgenic roots by *Agrobacterium rhizogenes*-mediated transformation, *Plant Cell, Tissue and Organ Culture* (2020) Vol. 141, pages 207-216.

Grafting

Grafting is a process that has been used for many years in some crops such as Cucurbitaceae but only more recently for some other commercial crops. Grafting may be used to provide a certain level of resistance to certain pests and pathogens. The variety of interest used as the graft or scion is grafted onto the resistant plant used as the rootstock. The resistant rootstock remains healthy and provides, from the soils, the normal supply for the graft that it isolates from the diseases. In some recent developments, it has also been shown that some rootstocks are also able to improve the agronomic value for the grafted plant and in particular the equilibrium between the vegetative and generative development that are always difficult to balance in cucumber cultivation.

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In some embodiments, the plants are selected on the basis of one or more phenotypic traits. Skilled persons will readily appreciate that such traits include any observable characteristic of the plant, including for example fruit size, weight, color, shape uniformity, appearance, taste, aroma and yield; plant growth rate, vigor, plant health, maturity, branching, height, leaf coverage, weight, total yield, color, taste, sugar levels, aroma, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (number of fruit) or biomass production; effects on plant growth that results in an increased seed yield for a crop; effects on plant growth which result in an increased yield; effects on plant growth that lead to an increased resistance or tolerance to disease including fungal, viral or bacterial diseases, to *mycoplasma*, or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of cucumber exocarp (skin) of said fruit.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Transcriptome Sequencing), qRTPCR (quantitative real time PCR). In some embodiments, plants of the varieties described herein can be identified based on the presence of molecular markers associated with the quantitative trait of small fruit and increased fruit number.

In some embodiments, descendants of the varieties described herein, e.g., those lines in which the quantitative trait has been bred into, can be identified based on the presence of molecular markers associated with various quantitative trait loci. In some embodiments, the molecular markers are selected from SEQ ID NOs: 1-108. In some embodiments, the marker identifies one or more of the polymorphisms shown in Table 13. In some embodiments, the marker identifies one or more of the polymorphisms shown in Table 5.

In some embodiments, descendants of the varieties described herein comprise at least one polymorphism selected from the group consisting of: a C nucleotide at a position corresponding to 12353523 on chromosome two; a G nucleotide at a position corresponding to 12243164 on chromosome two; a C nucleotide at a position corresponding to 12286929 on chromosome two; a CA nucleotide sequence at a position corresponding to 12288079 on chromosome two; a C nucleotide at a position corresponding to 12288088 on chromosome two; a G nucleotide at a position corresponding to 12080941 on chromosome two; a T nucleotide at a position corresponding to 12288102 on chromosome two; a T nucleotide at a position corresponding to 12248206 on chromosome two; an A nucleotide at a position corresponding to 12973019 on chromosome two; and a G nucleotide at a position corresponding to 12194314 on chromosome two, wherein the nucleotide positions correspond to cucumber reference genome CLv4.0.

In some embodiments, descendants of the varieties described herein comprise at least one polymorphism selected from the group consisting of: at least one polymorphism on chromosome two selected from Table 7; at least one polymorphism on chromosome three selected from Table 8; and at least one polymorphism on chromosome five selected from Table 9.

In some embodiments, descendants of the varieties described herein comprise at least one polymorphism on chromosome two selected from the group consisting of: a haplotype block spanning positions 8993182 and 8994169; a haplotype block spanning positions 9275096 and 9275683; a haplotype block spanning positions 9480014 and 9480040; a haplotype block spanning positions 9660643 and 9663935; a haplotype block spanning positions 9823235 and 9834415; a haplotype block spanning positions 11235085 and 11235101; a haplotype block spanning positions 12148657 and 12148670; a haplotype block spanning positions 12240594 and 12248206; a haplotype block spanning positions 12286929 and 12288102; and a haplotype block spanning positions 12551579 and 12551930, wherein the nucleotide positions correspond to cucumber reference genome CLv4.0.

In some embodiments, descendants of the varieties described herein comprise at least one polymorphism on chromosome three selected from the group consisting of: a haplotype block spanning positions 14974952 and 14997747; a haplotype block spanning positions 15279331 and 15294373; and a haplotype block spanning positions 15363590 and 15367135, wherein the nucleotide positions correspond to cucumber reference genome CLv4.0.

In some embodiments, descendants of the varieties described herein comprise at least one polymorphism on chromosome five selected from the group consisting of: a haplotype block spanning positions 24890873 and 24890873; a haplotype block spanning positions 25207022 and 25207022; a haplotype block spanning positions 25218084 and 25223821; and a haplotype block spanning positions 25275153 and 25275153.

In some embodiments, descendants of the varieties described herein comprise at least one polymorphism selected from the group consisting of: at least one polymorphism associated with internode length selected from Table 10; at least one polymorphism associated with fruit length:

diameter ratio selected from Table 11; and at least one polymorphism associated with flower size selected from Table 12.

In some embodiments, descendants of the varieties described herein comprise at least one polymorphism selected from the group consisting of: a G nucleotide at a position corresponding to 14977238 on chromosome three; an A nucleotide at a position corresponding to 25218084 on chromosome five; a GC nucleotide sequence at a position corresponding to 25275153 on chromosome five; a C nucleotide at a position corresponding to 24890873 on chromosome five; and a G nucleotide at a position corresponding to 25207022 on chromosome five, wherein the nucleotide positions correspond to cucumber reference genome CLv4.0.

The disclosure also provides methods for determining the identity of parental lines of plants described herein. US 2015/0126380 relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a variety described herein, or is a progeny of said variety, because the seed coat of the seed is a maternal tissue genetically identical to the variety described herein. In one aspect, the disclosure relates to a seed coat comprising maternal tissue of a variety described herein. In another aspect, the disclosure relates to a cucumber seed comprising a maternal tissue of a hybrid or inbred cucumber variety described herein. In another aspect, the disclosure provides for a method of identifying the female parental line of a hybrid or inbred cucumber variety described herein by analyzing the seed coat of a seed of that variety. In another aspect, the skilled person can determine whether a seed is grown on a hybrid or inbred cucumber variety described herein by analyzing the seed coat or another maternal tissue of said seed.

To map QTLs associated with the evaluated traits, three F2 populations were generated. Each population resulted from crossing one of the disclosed cucumber lines, each expressing at least one trait of interest, with a Beit-Alpha type cucumber line. Populations composed of 80-100 plants each and were grown in a protected structure in Nativ HaAsara.

Flower size was scored on a 1-9 scale (see FIG. 3 for example). The cucumber varieties disclosed herein have small female flowers, approximately 10-15 mm in diameter (corresponding to a score of "3"). Comparison variety 'Qwerty' has flowers that are typically 25-30 mm in diameter.

Fruit ratio (length/diameter): For immature and mature fruits, five representative fruits per plant were measured in cm. For mature fruit assessments, two fruits per plant were tagged at the start of the experiment to ensure consistent developmental stage at harvest.

Average internode length: Stem height was measured in cm from the ground to the first node, and from the first to the ninth node. Average internode length was calculated as: ((height from 1st to 9th node)/8) representing the mean of the eight internodes between these nodes.

Whole-genome sequencing and variant calling total of 180 plants including F2 individuals as well as internal and commercial controls were performed by IGATech (IGATech S.r.l., Udine, Italy; https://igatechnology.com/igatech/science-network). Reads were aligned to the cucumber reference genome CLv4.0 (Guan et al., 2024), and variant calling produced a multi-sample VCF.

Both qualitative and quantitative traits were converted into binary phenotypic classes ("desired" vs. "undesired") using trait-specific thresholds as shown in Table 4 below.

TABLE 4

Trait-specific thresholds

| Trait | Desired (lower than) | Undesired (higher than) |
|---|---|---|
| Flower size | <4 | >6 |
| AV. Internode Length | <3.25 cm | >4.75 cm |
| AV. Immature fruit ratio | <3.25 | >4 |

Fisher's exact test was applied to detect SNPs showing significant allele-frequency differences between the two phenotypic classes. These genome-wide results were used to identify initial QTL candidates.

Following the Fisher-based screening, two complementary Manhattan plots were generated to visualize SNP-trait associations and help define putative QTL intervals. The first Manhattan plot summarizes the Fisher association results for all SNPs across the genome, providing a broad overview of candidate QTL regions. To highlight 'HRZ-CS-24-0001H'-specific alleles, a second Manhattan plot was constructed using SNPs where Qwerty and 'HRZ-CS-24-0001H' differ. Loci where 'Qwerty' was heterozygous (Ref/Alt) or homozygous for the reference allele (Ref/Ref), while the 'HRZ-CS-24-0001H' parental lines were homozygous for the alternate allele (Alt/Alt) were retained. From this subset, SNPs were extracted for which 'Qwerty' was homozygous for the reference allele (Ref/Ref). These SNPs represent 'HRZ-CS-24-0001H'-unique alleles absent from the commercial background.

Within each putative QTL region, the most significant SNPs identified by Fisher's exact test were retained for quantitative analysis. To evaluate the contribution of shared and 'HRZ-CS-24-0001H'-specific loci, a two-step linear modelling analysis was implemented: Base model-included only Qwerty-'HRZ-CS-24-0001H' shared QTLs; Extended model-included both the shared QTLs and the 'HRZ-CS-24-0001H'-unique SNPs.

Model comparison was performed using ANOVA to quantify the additional variance explained by 'HRZ-CS-24-0001H'-unique loci and to determine their additive contribution to the trait beyond the shared QTL background. Linear models and ANOVA were also used to assess the individual and combined effects of these loci across all quantitative traits.

For each selected SNP, a pair of primers (forward and reverse) flanking the polymorphic site can be designed and synthesized. In addition, allele-specific probes complementary to either the reference or the alternate allele can be designed for use in a PCR assay. This system enables accurate genotyping by detecting fluorescence signals corresponding to each SNP allele, thereby allowing reliable differentiation between genotypes at the marker locus.

The following Tables 5-13 list polymorphisms which may be used to identify the traits associated with the small cucumber fruit phenotype, and to follow the traits during breeding selection. The polymorphism positions are aligned to the cucumber reference genome CLv4.0 (Guan J. et al., A near-complete cucumber reference genome assembly and Cucumber-DB, a multi-omics database, *Molecular Plant*, Vol. 17, Issue 8, 2024, Pg 1178-1182).

TABLE 5

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| Unique polymorphisms associated with the phenotype described herein | | | | | | | |
| AV.Immature_Ratio | chr3 | 15279331 | 2.59915E-06 | TC/TC | T/T | T/T | 1 |
| AV.Immature_Ratio | chr3 | 15288885 | 2.59915E-06 | G/G | A/A | A/A | 2 |
| AV.Immature_Ratio | chr3 | 15313183 | 2.59915E-06 | A/A | C/C | C/C | 3 |
| AV.Immature_Ratio | chr3 | 15313185 | 2.59915E-06 | A/A | T/T | T/T | 4 |
| AV.Immature_Ratio | chr3 | 15313686 | 2.59915E-06 | G/G | T/T | T/T | 5 |
| AV.Immature_Ratio | chr3 | 15329188 | 2.59915E-06 | A/A | T/T | T/T | 6 |
| AV.Immature_Ratio | chr3 | 15364079 | 2.59915E-06 | C/C | CT/CT | CT/CT | 7 |
| AV.Immature_Ratio | chr3 | 15364081 | 2.59915E-06 | G/G | A/A | A/A | 8 |
| AV.Immature_Ratio | chr3 | 15364082 | 2.59915E-06 | G/G | A/A | A/A | 9 |
| AV.Immature_Ratio | chr3 | 15364103 | 2.59915E-06 | T/T | C/C | C/C | 10 |
| AV.Immature_Ratio | chr3 | 15367135 | 2.59915E-06 | T/T | C/C | C/C | 11 |
| AV.Immature_Ratio | chr3 | 15396001 | 2.59915E-06 | G/G | C/C | C/C | 12 |
| AV.Immature_Ratio | chr3 | 15363590 | 3.8236E-06 | T/T | A/A | A/A | 13 |
| AV.Immature_Ratio | chr3 | 15363592 | 3.8236E-06 | G/G | C/C | C/C | 14 |
| AV.Immature_Ratio | chr3 | 15291884 | 6.35348E-06 | T/T | A/A | A/A | 15 |
| AV.Immature_Ratio | chr3 | 15292223 | 6.35348E-06 | A/A | C/C | C/C | 16 |
| AV.Immature_Ratio | chr3 | 15292244 | 6.35348E-06 | C/C | T/T | T/T | 17 |
| AV.Immature_Ratio | chr3 | 15292548 | 6.35348E-06 | G/G | C/C | C/C | 18 |
| AV.Immature_Ratio | chr3 | 15294358 | 6.35348E-06 | T/T | C/C | C/C | 19 |
| AV.Immature_Ratio | chr3 | 15294373 | 6.35348E-06 | A/A | T/T | T/T | 20 |
| AV.Internode_Length | chr2 | 11235085 | 7.5675E-10 | T/T | C/C | C/C | 21 |
| AV.Internode_Length | chr2 | 11235089 | 7.5675E-10 | T/T | C/C | C/C | 22 |
| AV.Internode_Length | chr2 | 11235090 | 7.5675E-10 | A/A | G/G | G/G | 23 |
| AV.Internode_Length | chr2 | 11235096 | 7.5675E-10 | A/A | G/G | G/G | 24 |
| AV.Internode_Length | chr2 | 11235101 | 7.5675E-10 | C/C | T/T | T/T | 25 |
| AV.Internode_Length | chr2 | 8994169 | 7.5675E-10 | C/C | T/T | T/T | 26 |
| AV.Internode_Length | chr2 | 9275683 | 7.5675E-10 | C/C | T/T | T/T | 27 |
| AV.Internode_Length | chr2 | 9480014 | 7.5675E-10 | C/C | G/G | G/G | 28 |
| AV.Internode_Length | chr2 | 9480015 | 7.5675E-10 | G/G | A/A | A/A | 29 |
| AV.Internode_Length | chr2 | 9480040 | 7.5675E-10 | C/C | T/T | T/T | 30 |
| AV.Internode_Length | chr2 | 9823235 | 7.5675E-10 | T/T | C/C | C/C | 31 |
| AV.Internode_Length | chr2 | 9834415 | 7.5675E-10 | G/G | A/A | A/A | 32 |
| AV.Internode_Length | chr2 | 12551579 | 9.09571E-10 | A/A | T/T | T/T | 33 |
| AV.Internode_Length | chr2 | 12173956 | 1.14363E-09 | G/G | A/A | A/A | 34 |

TABLE 5-continued

| Unique polymorphisms associated with the phenotype described herein | | | | | | | |
|---|---|---|---|---|---|---|---|
| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
| AV.Internode_Length | chr2 | 9275096 | 1.14363E-09 | A/A | G/G | G/G | 35 |
| AV.Internode_Length | chr2 | 11220421 | 1.43956E-09 | T/T | G/G | G/G | 36 |
| AV.Internode_Length | chr2 | 9660643 | 1.43956E-09 | A/A | G/G | G/G | 37 |
| AV.Internode_Length | chr2 | 9824945 | 1.43956E-09 | A/A | G/G | G/G | 38 |
| AV.Internode_Length | chr2 | 9824964 | 1.43956E-09 | G/G | A/A | A/A | 39 |
| AV.Internode_Length | chr2 | 8993182 | 1.51504E-09 | G/G | GT/GT | GT/GT | 40 |
| AV.Internode_Length | chr5 | 25218084 | 1.25333E-06 | AAATGAAAAT GAGAGTTTAT TTTTAATGTT/ AAATGAAAAT GAGAGTTTAT TTTTAATGTT | A/A | A/A | 41 |
| AV.Internode_Length | chr5 | 25275153 | 1.25333E-06 | G/G | GC/GC | GC/GC | 42 |
| AV.Internode_Length | chr5 | 24890873 | 4.76804E-06 | T/T | C/C | C/C | 44 |
| AV.Internode_Length | chr5 | 25207022 | 4.76804E-06 | C/C | G/G | G/G | 45 |
| AV.Internode_Length | chr3 | 14948864 | 6.85499E-06 | A/A | AT/AT | AT/AT | 46 |
| AV.Internode_Length | chr3 | 14977238 | 9.92409E-06 | A/A | G/G | G/G | 47 |
| Flower.size | chr2 | 12353523 | 3.25819E-12 | G/C | C/C | C/C | 48 |
| Flower.size | chr2 | 12243164 | 3.80103E-12 | T/T | G/G | G/G | 49 |
| Flower.size | chr2 | 12286929 | 4.3135E-12 | T/T | C/C | C/C | 50 |
| Flower.size | chr2 | 12288079 | 4.75827E-12 | C/C | CA/CA | CA/CA | 51 |
| Flower.size | chr2 | 12288088 | 4.85524E-12 | A/A | C/C | C/C | 52 |
| Flower.size | chr2 | 12080941 | 5.61479E-12 | A/A | G/G | G/G | 85 |
| Flower.size | chr2 | 12288102 | 8.32709E-12 | A/A | T/T | T/T | 86 |
| Flower.size | chr2 | 12248206 | 9.46901E-12 | C/C | T/T | T/T | 87 |
| Flower.size | chr2 | 12973019 | 9.90329E-12 | AG/AG | A/A | A/A | 88 |
| Flower.size | chr2 | 12194314 | 1.01382E-11 | T/T | G/G | G/G | 89 |
| Flower.size | chr2 | 9663935 | 1.1703E-11 | C/C | T/T | T/T | 90 |
| Flower.size | chr2 | 12288068 | 1.23998E-11 | C/C | T/T | T/T | 91 |
| Flower.size | chr2 | 12288069 | 1.23998E-11 | T/T | C/C | C/C | 92 |
| Flower.size | chr2 | 12240594 | 1.33292E-11 | G/G | A/A | A/A | 93 |
| Flower.size | chr2 | 12551930 | 1.33292E-11 | G/G | A/A | A/A | 94 |
| Flower.size | chr2 | 12148657 | 1.39777E-11 | G/G | A/ | A/A | 95 |
| Flower.size | chr2 | 11739457 | 1.90271E-11 | G/G | A/A | A/A | 96 |
| Flower.size | chr2 | 12148667 | 1.98327E-11 | G/G | C/C | C/C | 97 |
| Flower.size | chr2 | 12148668 | 1.98327E-11 | G/G | A/A | A/A | 98 |
| Flower.size | chr2 | 12148670 | 1.98327E-11 | A/A | G/G | G/G | 99 |

TABLE 5-continued

Unique polymorphisms associated with the phenotype described herein

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| Flower.size | chr3 | 15222842 | 3.27692E-09 | C/C | CTGATCGA/CTGATCGA | CTGATCGA/CTGATCGA | 100 |
| Flower.size | chr3 | 14981424 | 6.13284E-09 | G/G | A/A | A/A | 101 |
| Flower.size | chr3 | 14981441 | 6.13284E-09 | A/A | G/G | G/G | 102 |
| Flower.size | chr3 | 14977238 | 7.98772E-09 | A/A | G/G | G/G | 47 |
| Flower.size | chr3 | 14984328 | 1.59713E-08 | C/C | T/T | T/T | 103 |
| Flower.size | chr3 | 14974952 | 1.90019E-08 | C/C | CA/CA | CA/CA | 104 |
| Flower.size | chr3 | 14948434 | 2.12737E-08 | G/G | A/A | A/A | 105 |
| Flower.size | chr3 | 14977910 | 2.12737E-08 | GT/GT | G/G | G/G | 106 |
| Flower.size | chr3 | 14978569 | 2.12737E-08 | G/G | A/A | A/A | 107 |
| Flower.size | chr3 | 14978970 | 2.12737E-08 | G/G | A/A | A/A | 108 |
| Flower.size | chr3 | 14978976 | 2.12737E-08 | C/C | T/T | T/T | 53 |
| Flower.size | chr3 | 14980262 | 2.12737E-08 | A/A | T/T | T/T | 54 |
| Flower.size | chr3 | 14980300 | 2.12737E-08 | T/T | TA/TA | TA/TA | 55 |
| Flower.size | chr3 | 14980308 | 2.12737E-08 | T/T | C/C | C/C | 56 |
| Flower.size | chr3 | 14981404 | 2.12737E-08 | T/T | C/C | C/C | 57 |
| Flower.size | chr3 | 14992856 | 2.12737E-08 | A/A | C/C | C/C | 58 |
| Flower.size | chr3 | 14995018 | 2.12737E-08 | TC/TC | T/T | T/T | 59 |
| Flower.size | chr3 | 14995026 | 2.12737E-08 | C/C | CT/CT | CT/CT | 60 |
| Flower.size | chr3 | 14997730 | 2.12737E-08 | T/T | G/G | G/G | 61 |
| Flower.size | chr3 | 14997747 | 2.12737E-08 | G/G | A/A | A/A | 62 |
| Flower.size | chr5 | 24224953 | 6.52322E-08 | C/C | G/G | G/C | 63 |
| Flower.size | chr5 | 25218084 | 1.74734E-07 | AAATGAAAATGAGAGTTTATTTTTAATGTT/AAATGAAAATGAGAGTTTATTTTTAATGTT | A/A | A/A | 41 |
| Flower.size | chr5 | 25275153 | 1.74734E-07 | G/G | GC/GC | GC/GC | 42 |
| Flower.size | chr5 | 25223821 | 2.04973E-07 | C/C | A/A | A/A | 64 |
| Flower.size | chr5 | 24890873 | 3.81092E-07 | T/T | C/C | C/C | 44 |
| Flower.size | chr5 | 25207022 | 3.81092E-07 | C/C | G/G | G/G | 45 |
| Flower.size | chr1 | 06933251 | 7.34999E-07 | C/C | CA/CA | CA/CA | 68 |

TABLE 6

| Chromosome 6 polymorphisms | | | | | | | |
|---|---|---|---|---|---|---|---|
| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
| AV.Internode_Length | chr6 | 4595835 | 2.4378E-06 | G/G | GAT/GAT | GAT/GAT | 43 |
| Flower.size | chr6 | 4595835 | 1.02797E-10 | G/G | GAT/GAT | GAT/GAT | 43 |
| Flower.size | chr6 | 4061488 | 4.14162E-07 | G/G | A/A | A/A | 65 |
| Flower.size | chr6 | 4061515 | 5.18449E-07 | G/G | A/A | A/A | 66 |
| Flower.size | chr6 | 34741034 | 7.07484E-07 | C/C | A/A | A/A | 67 |
| Flower.size | chr6 | 34741057 | 2.15485E-06 | TTGTTTTGA/TTGTTTTGA | T/T | T/T | 69 |
| Flower.size | chr6 | 34597313 | 2.51461E-06 | T/T | C/C | C/C | 70 |
| Flower.size | chr6 | 34602363 | 3.45785E-06 | C/C | G/G | G/G | 71 |
| Flower.size | chr6 | 35206403 | 6.02654E-06 | T/T | A/A | A/A | 72 |
| Flower.size | chr6 | 35011673 | 6.13489E-06 | C/C | T/T | T/T | 73 |
| Flower.size | chr6 | 34602338 | 6.9157E-06 | A/A | C/C | C/C | 74 |
| Flower.size | chr6 | 34602370 | 7.19687E-06 | AT/AT | A/A | A/A | 75 |
| Flower.size | chr6 | 34656752 | 7.21603E-06 | T/T | C/C | C/C | 76 |
| Flower.size | chr6 | 34597396 | 7.3557E-06 | C/C | T/T | T/T | 77 |
| Flower.size | chr6 | 34617699 | 7.79905E-06 | T/T | C/C | C/C | 78 |
| Flower.size | chr6 | 34705667 | 7.79905E-06 | C/C | T/T | T/T | 79 |
| Flower.size | chr6 | 34705669 | 7.79905E-06 | C/C | G/G | G/G | 80 |
| Flower.size | chr6 | 34705672 | 7.79905E-06 | C/C | G/G | G/G | 81 |
| Flower.size | chr6 | 34602404 | 8.40912E-06 | A/A | G/G | G/G | 82 |
| Flower.size | chr6 | 35206497 | 8.40912E-06 | A/A | C/C | C/C | 83 |
| Flower.size | chr6 | 34599743 | 8.45252E-06 | T/T | C/C | C/C | 84 |

TABLE 7

| Chromosome 2 polymorphisms | | | | | | | |
|---|---|---|---|---|---|---|---|
| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
| AV.Internode_Length | chr2 | 11235085 | 7.5675E−10 | T/T | C/C | C/C | 21 |
| AV.Internode_Length | chr2 | 11235089 | 7.5675E−10 | T/T | C/C | C/C | 22 |
| AV.Internode_Length | chr2 | 11235090 | 7.5675E−10 | A/A | G/G | G/G | 23 |
| AV.Internode_Length | chr2 | 11235096 | 7.5675E−10 | A/A | G/G | G/G | 24 |
| AV.Internode_Length | chr2 | 11235101 | 7.5675E−10 | C/C | T/T | T/T | 25 |
| AV.Internode_Length | chr2 | 8994169 | 7.5675E−10 | C/C | T/T | T/T | 26 |
| AV.Internode_Length | chr2 | 9275683 | 7.5675E−10 | C/C | T/T | T/T | 27 |
| AV.Internode_Length | chr2 | 9480014 | 7.5675E−10 | C/C | G/G | G/G | 28 |
| AV.Internode_Length | chr2 | 9480015 | 7.5675E−10 | G/G | A/A | A/A | 29 |
| AV.Internode_Length | chr2 | 9480040 | 7.5675E−10 | C/C | T/T | T/T | 30 |
| AV.Internode_Length | chr2 | 9823235 | 7.5675E−10 | T/T | C/C | C/C | 31 |
| AV.Internode_Length | chr2 | 9834415 | 7.5675E−10 | G/G | A/A | A/A | 32 |
| AV.Internode_Length | chr2 | 12551579 | 9.09571E−10 | A/A | T/T | T/T | 33 |
| AV.Internode_Length | chr2 | 12173956 | 1.14363E−09 | G/G | A/A | A/A | 34 |

TABLE 7-continued

Chromosome 2 polymorphisms

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| AV.Internode_Length | chr2 | 9275096 | 1.14363E-09 | A/A | G/G | G/G | 35 |
| AV.Internode_Length | chr2 | 11220421 | 1.43956E-09 | T/T | G/G | G/G | 36 |
| AV.Internode_Length | chr2 | 9660643 | 1.43956E-09 | A/A | G/G | G/G | 37 |
| AV.Internode_Length | chr2 | 9824945 | 1.43956E-09 | A/A | G/G | G/G | 38 |
| AV.Internode_Length | chr2 | 9824964 | 1.43956E-09 | G/C | A/A | A/A | 39 |
| AV.Internode_Length | chr2 | 8993182 | 1.51504E-09 | G/G | GT/GT | GT/GT | 40 |
| Flower.size | chr2 | 12353523 | 3.25819E-12 | G/G | C/C | C/C | 48 |
| Flower.size | chr2 | 12243164 | 3.80103E-12 | T/T | G/G | G/G | 49 |
| Flower.size | chr2 | 12286929 | 4.3135E-12 | T/T | C/C | C/C | 50 |
| Flower.size | chr2 | 12288079 | 4.75827E-12 | C/C | CA/CA | CA/CA | 51 |
| Flower.size | chr2 | 12288088 | 4.85524E-12 | A/A | C/C | C/C | 52 |
| Flower.size | chr2 | 12080941 | 5.61479E-12 | A/A | G/G | G/G | 85 |
| Flower.size | chr2 | 12288102 | 8.32709E-12 | A/A | T/T | T/T | 86 |
| Flower.size | chr2 | 12248206 | 9.46901E-12 | C/C | T/T | T/T | 87 |
| Flower.size | chr2 | 12973019 | 9.90329E-12 | AG/AG | A/A | A/A | 88 |
| Flower.size | chr2 | 12194314 | 1.01382E-11 | T/T | G/G | G/G | 89 |
| Flower.size | chr2 | 9663935 | 1.1703E-11 | C/C | T/T | T/T | 90 |
| Flower.size | chr2 | 12288068 | 1.23998E-11 | C/C | T/T | T/T | 91 |
| Flower.size | chr2 | 12288069 | 1.23998E-11 | T/T | C/C | C/C | 92 |
| Flower.size | chr2 | 12240594 | 1.33292E-11 | G/G | A/A | A/A | 93 |
| Flower.size | chr2 | 12551930 | 1.33292E-11 | G/G | A/A | A/A | 94 |
| Flower.size | chr2 | 12148657 | 1.39777E-11 | G/G | A/A | A/A | 95 |
| Flower.size | chr2 | 11739457 | 1.90271E-11 | G/G | A/A | A/A | 96 |
| Flower.size | chr2 | 12148667 | 1.98327E-11 | G/G | C/C | C/C | 97 |
| Flower.size | chr2 | 12148668 | 1.98327E-11 | G/G | A/A | A/A | 98 |
| Flower.size | chr2 | 12148670 | 1.98327E-11 | A/A | G/G | G/G | 99 |

TABLE 8

Chromosome 3 polymorphisms

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| AV.Immature_Ratio | chr3 | 15279331 | 2.59915E-06 | TC/TC | T/T | T/T | 1 |
| AV.Immature_Ratio | chr3 | 15288885 | 2.59915E-06 | G/G | A/A | A/A | 2 |
| AV.Immature_Ratio | chr3 | 15313183 | 2.59915E-06 | A/A | C/C | C/C | 3 |
| AV.Immature_Ratio | chr3 | 15313185 | 2.59915E-06 | A/A | T/T | T/T | 4 |
| AV.Immature_Ratio | chr3 | 15313686 | 2.59915E-06 | G/G | T/T | T/T | 5 |
| AV.Immature_Ratio | chr3 | 15329188 | 2.59915E-06 | A/A | T/T | T/T | 6 |
| AV.Immature_Ratio | chr3 | 15364079 | 2.59915E-06 | C/C | CT/CT | CT/CT | 7 |
| AV.Immature_Ratio | chr3 | 15364081 | 2.59915E-06 | G/G | A/A | A/A | 8 |
| AV.Immature_Ratio | chr3 | 15364082 | 2.59915E-06 | G/G | A/A | A/A | 9 |
| AV.Immature_Ratio | chr3 | 15364103 | 2.59915E-06 | T/T | C/C | C/C | 10 |
| AV.Immature_Ratio | chr3 | 15367135 | 2.59915E-06 | T/T | C/C | C/C | 11 |
| AV.Immature_Ratio | chr3 | 15396001 | 2.59915E-06 | G/G | C/C | C/C | 12 |
| AV.Immature_Ratio | chr3 | 15363590 | 3.8236E-06 | T/T | A/A | A/A | 13 |
| AV.Immature_Ratio | chr3 | 15363592 | 3.8236E-06 | G/G | C/C | C/C | 14 |
| AV.Immature_Ratio | chr3 | 15291884 | 6.35348E-06 | T/T | A/A | A/A | 15 |
| AV.Immature_Ratio | chr3 | 15292223 | 6.35348E-06 | A/A | C/C | C/C | 16 |

TABLE 8-continued

Chromosome 3 polymorphisms

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| AV.Immature_Ratio | chr3 | 15292244 | 6.35348E-06 | C/C | T/T | T/T | 17 |
| AV.Immature_Ratio | chr3 | 15292548 | 6.35348E-06 | G/G | C/C | C/C | 18 |
| AV.Immature_Ratio | chr3 | 15294358 | 6.35348E-06 | T/T | C/C | C/C | 19 |
| AV.Immature_Ratio | chr3 | 15294373 | 6.35348E-06 | A/A | T/T | T/T | 20 |
| AV.Internode_Length | chr3 | 14948864 | 6.85499E-06 | A/A | AT/AT | AT/AT | 46 |
| AV.Internode_Length | chr3 | 14977238 | 9.92409E-06 | A/A | G/G | G/G | 47 |
| Flower.size | chr3 | 15222842 | 3.27692E-09 | C/C | CTGATCGA/ CTGATCGA | CTGATCGA/ CTGATCGA | 100 |
| Flower.size | chr3 | 14981424 | 6.13284E-09 | G/G | A/A | A/A | 101 |
| Flower.size | chr3 | 14981441 | 6.13284E-09 | A/A | G/G | G/G | 102 |
| Flower.size | chr3 | 14977238 | 7.98772E-09 | A/A | G/G | G/G | 47 |
| Flower.size | chr3 | 14984328 | 1.59713E-08 | C/C | T/T | T/T | 103 |
| Flower.size | chr3 | 14974952 | 1.90019E-08 | C/C | CA/CA | CA/CA | 104 |
| Flower.size | chr3 | 14948434 | 2.12737E-08 | G/G | A/A | A/A | 105 |
| Flower.size | chr3 | 14977910 | 2.12737E-08 | GT/GT | G/G | G/G | 106 |
| Flower.size | chr3 | 14978569 | 2.12737E-08 | G/G | A/A | A/A | 107 |
| Flower.size | chr3 | 14978970 | 2.12737E-08 | G/G | A/A | A/A | 108 |
| Flower.size | chr3 | 14978976 | 2.12737E-08 | C/C | T/T | T/T | 53 |
| Flower.size | chr3 | 14980262 | 2.12737E-08 | A/A | T/T | T/T | 54 |
| Flower.size | chr3 | 14980300 | 2.12737E-08 | T/T | TA/TA | TA/TA | 55 |
| Flower.size | chr3 | 14980308 | 2.12737E-08 | T/T | C/C | C/C | 56 |
| Flower.size | chr3 | 14981404 | 2.12737E-08 | T/T | C/C | C/C | 57 |
| Flower.size | chr3 | 14992856 | 2.12737E-08 | A/A | C/C | C/C | 58 |
| Flower.size | chr3 | 14995018 | 2.12737E-08 | TC/TC | T/T | T/T | 59 |
| Flower.size | chr3 | 14995026 | 2.12737E-08 | C/C | CT/CT | CT/CT | 60 |
| Flower.size | chr3 | 14997730 | 2.12737E-08 | T/T | G/G | G/G | 61 |
| Flower.size | chr3 | 14997747 | 2.12737E-08 | G/G | A/A | A/A | 62 |

TABLE 9

Chromosome 5 polymorphisms

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| AV.Internode_Length | chr5 | 25218084 | 1.25333E-06 | AAATGAAAAT GAGAGTTTAT TTTTAATGTT/ | A/A | A/A | 41 |

TABLE 9-continued

Chromosome 5 polymorphisms

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| | | | | AAATGAAAAT GAGAGTTTAT TTTTAATGTT | | | |
| AV.Internode_Length | chr5 | 25275153 | 1.25333E-06 | G/G | GC/GC | GC/GC | 42 |
| AV.Internode_Length | chr5 | 24890873 | 4.76804E-06 | T/T | C/C | C/C | 44 |
| AV.Internode_Length | chr5 | 25207022 | 4.76804E-06 | C/C | G/G | G/G | 45 |
| Flower.size | chr5 | 24224953 | 6.52322E-08 | C/C | G/G | G/G | 63 |
| Flower.size | chr5 | 25218084 | 1.74734E-07 | AAATGAAAAT GAGAGTTTAT TTTTAATGTT/ AAATGAAAAT GAGAGTTTAT TTTTAATGTT | A/A | A/A | 41 |
| Flower.size | chr5 | 25275153 | 1.74734E-07 | G/G | GC/GC | GC/GC | 42 |
| Flower.size | chr5 | 25223821 | 2.04973E-07 | C/C | A/A | A/A | 64 |
| Flower.size | chr5 | 24890873 | 3.81092E-07 | T/T | C/C | C/C | 44 |
| Flower.size | chr5 | 25207022 | 3.81092E-07 | C/C | G/G | G/G | 45 |

TABLE 10

Polymorphisms associated with shorter internode length

| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
|---|---|---|---|---|---|---|---|
| AV.Internode_Length | chr2 | 11235085 | 7.5675E-10 | T/T | C/C | C/C | 21 |
| AV.Internode_Length | chr2 | 11235089 | 7.5675E-10 | T/T | C/C | C/C | 22 |
| AV.Internode_Length | chr2 | 11235090 | 7.5675E-10 | A/A | G/G | G/G | 23 |
| AV.Internode_Length | chr2 | 11235096 | 7.5675E-10 | A/A | G/G | G/G | 24 |
| AV.Internode_Length | chr2 | 11235101 | 7.5675E-10 | C/C | T/T | T/T | 25 |
| AV.Internode_Length | chr2 | 8994169 | 7.5675E-10 | C/C | T/T | T/T | 26 |
| AV.Internode_Length | chr2 | 9275683 | 7.5675E-10 | C/C | T/T | T/T | 27 |
| AV.Internode_Length | chr2 | 9480014 | 7.5675E-10 | C/C | G/G | G/G | 28 |
| AV.Internode_Length | chr2 | 9480015 | 7.5675E-10 | G/G | A/A | A/A | 29 |
| AV.Internode_Length | chr2 | 9480040 | 7.5675E-10 | C/C | T/T | T/T | 30 |
| AV.Internode_Length | chr2 | 9823235 | 7.5675E-10 | T/T | C/C | C/C | 31 |
| AV.Internode_Length | chr2 | 9834415 | 7.5675E-10 | G/G | A/A | A/A | 32 |
| AV.Internode_Length | chr2 | 12551579 | 9.09571E-10 | A/A | T/T | T/T | 33 |
| AV.Internode_Length | chr2 | 12173956 | 1.14363E-09 | G/G | A/A | A/A | 34 |
| AV.Internode_Length | chr2 | 9275096 | 1.14363E-09 | A/A | G/G | G/G | 35 |

TABLE 10-continued

| Polymorphisms associated with shorter internode length | | | | | | | |
|---|---|---|---|---|---|---|---|
| Trait | Chrom | Position in cucumber reference genome CLv4.0 | P-Value.Fisher | 'Qwerty' | 'HRZ-CS-24-0003L' | 'HRZ-CS-24-0004L' | Marker SEQ ID NO: |
| AV.Internode_Length | chr2 | 11220421 | 1.43956E-09 | T/T | G/G | G/G | 36 |
| AV.Internode_Length | chr2 | 9660643 | 1.43956E-09 | A/A | G/G | G/G | 37 |
| AV.Internode_Length | chr2 | 9824945 | 1.43956E-09 | A/A | G/G | G/G | 38 |
| AV.Internode_Length | chr2 | 9824964 | 1.43956E-09 | G/G | A/A | A/A | 39 |
| AV.Internode_Length | chr2 | 8993182 | 1.51504E-09 | G/G | GT/GT | GT/GT | 40 |
| AV.Internode_Length | chr5 | 25218084 | 1.25333E-06 | AAATGAAAAT GAGAGTTTAT TTTTAATGTT/ AAATGAAAAT GAGAGTTTAT TTTTAATGTT | A/A | A/A | 41 |
| AV.Internode_Length | chr5 | 25275153 | 1.25333E-06 | G/C | GC/GC | GC/GC | 42 |
| AV.Internode_Length | chr6 | 4595835 | 2.4378E-06 | G/G | GAT/GAT | GAT/GAT | 43 |
| AV.Internode_Length | chr5 | 24890873 | 4.76804E-06 | T/T | C/C | C/C | 44 |
| AV.Internode_Length | chr5 | 25207022 | 4.76804E-06 | C/C | G/G | G/G | 45 |
| AV.Internode_Length | chr3 | 14948864 | 6.85499E-06 | A/A | AT/AT | AT/AT | 46 |
| AV.Internode_Length | chr3 | 14977238 | 9.92409E-06 | A/A | G/G | G/G | 47 |

TABLE 11

| Polymorphisms associated with fruit length; diameter ratio | | | | | | | |
|---|---|---|---|---|---|---|---|
| Trait | Chrom | Position cucumber reference genome CLv4.0 | P-Value.Fisher | 'Qwerty' | 'HRZ-CS-24-0003L' | 'HRZ-CS-24-0004L' | Marker SEQ ID NO: |
| AV.Immature_Ratio | chr3 | 15279331 | 2.59915E−06 | TC/TC | T/T | T/T | 1 |
| AV.Immature_Ratio | chr3 | 15288885 | 2.59915E−06 | G/G | A/A | A/A | 2 |
| AV.Immature_Ratio | chr3 | 15313183 | 2.59915E−06 | A/A | C/C | C/C | 3 |
| AV.Immature_Ratio | chr3 | 15313185 | 2.59915E−06 | A/A | T/T | T/T | 4 |
| AV.Immature_Ratio | chr3 | 15313686 | 2.59915E−06 | G/G | T/T | T/T | 5 |
| AV.Immature_Ratio | chr3 | 15329188 | 2.59915E−06 | A/A | T/T | T/T | 6 |
| AV.Immature_Ratio | chr3 | 15364079 | 2.59915E−06 | C/C | CT/CT | CT/CT | 7 |
| AV.Immature_Ratio | chr3 | 15364081 | 2.59915E−06 | G/G | A/A | A/A | 8 |
| AV.Immature_Ratio | chr3 | 15364082 | 2.59915E−06 | G/G | A/A | A/A | 9 |
| AV.Immature_Ratio | chr3 | 15364103 | 2.59915E−06 | T/T | C/C | C/C | 10 |
| AV.Immature_Ratio | chr3 | 15367135 | 2.59915E−06 | T/T | C/C | C/C | 11 |
| AV.Immature_Ratio | chr3 | 15396001 | 2.59915E−06 | G/G | C/C | C/C | 12 |
| AV.Immature_Ratio | chr3 | 15363590 | 3.8236E−06 | T/T | A/A | A/A | 13 |
| AV.Immature_Ratio | chr3 | 15363592 | 3.8236E−06 | G/G | C/C | C/C | 14 |
| AV.Immature_Ratio | chr3 | 15291884 | 6.35348E−06 | T/T | A/A | A/A | 15 |
| AV.Immature_Ratio | chr3 | 15292223 | 6.35348E−06 | A/A | C/C | C/C | 16 |
| AV.Immature_Ratio | chr3 | 15292244 | 6.35348E−06 | C/C | T/T | T/T | 17 |
| AV.Immature_Ratio | chr3 | 15292548 | 6.35348E−06 | G/G | C/C | C/C | 18 |
| AV.Immature_Ratio | chr3 | 15294358 | 6.35348E−06 | T/T | C/C | C/C | 19 |
| AV.Immature_Ratio | chr3 | 15294373 | 6.35348E−06 | A/A | T/T | T/T | 20 |

TABLE 12

| Trait | Chrom | Position in cucumber reference genome CLv4.0 | P-Value.Fisher | Qwerty | 'HRZ-CS-24-0003L' | 'HRZ-CS-24-0004L' | Marker SEQ ID NO: |
|---|---|---|---|---|---|---|---|
| Polymorphisms associated with smaller flower size | | | | | | | |
| Flower.size | chr3 | 15222842 | 3.27692E-09 | C/C | CTGATCGA/ CTGATCGA | CTGATCGA/ CTGATCGA | 100 |
| Flower.size | chr3 | 14981424 | 6.13284E-09 | G/G | A/A | A/A | 101 |
| Flower.size | chr3 | 14981441 | 6.13284E-09 | A/A | G/G | G/G | 102 |
| Flower.size | chr3 | 14977238 | 7.98772E-09 | A/A | G/G | G/G | 47 |
| Flower.size | chr3 | 14984328 | 1.59713E-08 | C/C | T/T | T/T | 103 |
| Flower.size | chr3 | 14974952 | 1.90019E-08 | C/C | CA/CA | CA/CA | 104 |
| Flower.size | chr3 | 14948434 | 2.12737E-08 | G/G | A/A | A/A | 105 |
| Flower.size | chr3 | 14977910 | 2.12737E-08 | GT/GT | G/G | G/G | 106 |
| Flower.size | chr3 | 14978569 | 2.12737E-08 | G/G | A/A | A/A | 107 |
| Flower.size | chr3 | 14978970 | 2.12737E-08 | G/G | A/A | A/A | 108 |
| Flower.size | chr3 | 14978976 | 2.12737E-08 | C/C | T/T | T/T | 53 |
| Flower.size | chr3 | 14980262 | 2.12737E-08 | A/A | T/T | T/T | 54 |
| Flower.size | chr3 | 14980300 | 2.12737E-08 | T/T | TA/TA | TA/TA | 55 |
| Flower.size | chr3 | 14980308 | 2.12737E-08 | T/T | C/C | C/C | 56 |
| Flower.size | chr3 | 14981404 | 2.12737E-08 | T/T | C/C | C/C | 57 |
| Flower.size | chr3 | 14992856 | 2.12737E-08 | A/A | C/C | C/C | 58 |
| Flower.size | chr3 | 14995018 | 2.12737E-08 | TC/TC | T/T | T/T | 59 |
| Flower.size | chr3 | 14995026 | 2.12737E-08 | C/C | CT/CT | CT/CT | 60 |
| Flower.size | chr3 | 14997730 | 2.12737E-08 | T/T | G/G | G/G | 61 |
| Flower.size | chr3 | 14997747 | 2.12737E-08 | G/G | A/A | A/A | 62 |

TABLE 13

| SEQ ID NO: | Sequence with polymorphism location noted by brackets | Polymorphism associated with disclosed phenotype |
|---|---|---|
| Sequences of the disclosure | | |
| 1 | CTTGGATAACAATTCAAATTTATTGTTACC[TC]TGAAGAAATAAAGACTATTATTACCAACC | T |
| 2 | TTGGAGTGCAGTTATTATAGGTTGTGTTTG[G]AGTAAATATTATTATAATTTGAGTTACTAT | A |
| 3 | TCATTATCGAAAAAATTCGACAAAACCTAC[A]TAATTATGCCAATACATGTCCTTATCTTCA | C |
| 4 | ATTATCGAAAAAATTCGACAAAACCTACAT[A]ATTATGCCAATACATGTCCTTATCTTCAAC | T |
| 5 | TATTAATATCTAAAATCAAAATTTTAGTAG[G]GTGGCGATTTCAAATAGAAATTTAAAATCA | T |
| 6 | ATCTTTAAGAGAACATTGCACTTAGTAAAT[A]AGCTTCGTTTGCTATTTCTTGGTTTTAACT | T |
| 7 | TGGAATGATTTGAACTCAAAATCTTTAGCT[C]GGGGTATATACGGGTACATATAATATTATA | CT |
| 8 | GAATGATTTGAACTCAAAATCTTTAGCTCG[G]GGTATATACGGGTACATATAATATTATATA | A |
| 9 | AATGATTTGAACTCAAAATCTTTAGCTCGG[G]GTATATACGGGTACATATAATATTATATAT | A |

TABLE 13-continued

| Sequences of the disclosure | | |
|---|---|---|
| SEQ ID NO: | Sequence with polymorphism location noted by brackets | Polymorphism associated with disclosed phenotype |
| 10 | TTAGCTCGGGGTATATACGGGTACATATAA[T]ATTATATATATACAACAAAAGTAGTCAAAA | C |
| 11 | TCATGAGTTTGGTTCAAAGTGACATGACTA[T]TATAAAATATGAAAAATGGTTACTAAGTT | C |
| 12 | GGGTCGAGAAATCACCTCTCAACTAATTAA[G]TTAACACCTCCTTAACGGCTTCCTAATATT | C |
| 13 | TTTTTTTTAAAAAAACTTATCTGCATATAA[T]TGTGAAAAAATTAATAATTTAATGTGTTTT | A |
| 14 | TTTTTTAAAAAAACTTATCTGCATATAATT[G]TGAAAAAATTAATAATTTAATGTGTTTTGT | C |
| 15 | TAACAAGCAACCAAATCGAACATGAACATA[T]ATCCATTGGCTCTGACATTAATATCTCTTA | A |
| 16 | TTCAACAACATAGAGTAAGAAGATTCAAAC[A]TCTGACTTGTTGATAGAGGACATACACCTT | C |
| 17 | GATTCAAACATCTGACTTGTTGATAGAGGA[C]ATACACCTTAATAAGATGTTCGTTGTATTA | T |
| 18 | TTATTAAGACATAAATATGAAAAAACGAGT[G]CTAAATGCCCCAAGCTTAAACTTCTCTTTT | C |
| 19 | TCTTTTAGTAGCTAACACCAGAAACTTGAT[T]GTCCTTTTTAGAGGATTTAAAACCAAGGCT | C |
| 20 | CACCAGAAACTTGATTGTCCTTTTTAGAGG[A]TTTAAAACCAAGGCTGCTTCTAAACTTAAG | T |
| 21 | TTAAGCTAAGATAGATATTATTTGTGTATT[T]CATTATACAAATAGACATAGTAGTTTATCA | C |
| 22 | GCTAAGATAGATATTATTTGTGTATTTCAT[T]ATACAAATAGACATAGTAGTTTATCATAGT | C |
| 23 | CTAAGATAGATATTATTTGTGTATTTCATT[A]TACAAATAGACATAGTAGTTTATCATAGTT | G |
| 24 | TAGATATTATTTGTGTATTTCATTATACAA[A]TAGACATAGTAGTTTATCATAGTTTATTAT | G |
| 25 | ATTATTTGTGTATTTCATTATACAAATAGA[C]ATAGTAGTTTATCATAGTTTATTATAGATA | T |
| 26 | TCTTTGGTCCTCCGCTCCCTCTGTCGACGA[C]GATCGCCTCCACCGCTACACTTCCGAGCCG | T |
| 27 | TAATTGAGTTTGAAAGACTGTATCGTTCAA[C]GACAAGTGTTGCTGTGAAGATGACATTTTT | T |
| 28 | ACAAAAAAATTAAAGTTATAAAAATTGATG[C]GAAGGTTAGCGGATGAATTTGCAATCTAAG | G |
| 29 | CAAAAAAATTAAAGTTATAAAAATTGATGC[G]AAGGTTAGCGGATGAATTTGCAATCTAAGG | A |
| 30 | GATGCGAAGGTTAGCGGATGAATTTGCAAT[C]TAAGGAGGGTTATAAACCTTCGACAATATT | T |
| 31 | TGCATCGCATGCTAACCTTGCAAGAGGTAT[T]GTGTGTGTGCTTGCCACCTATCTAGTGTCC | C |
| 32 | TCAACCCGTATAAGGCTTTCGAAGCTTGCA[G]ACCTGATTATTAAATTGAGCTTCAAATCTT | A |
| 33 | TATTATATAACACACATTGATATTATCAAA[A]AAATGTGACAACTTCAAATTAGCATGTGAA | T |
| 34 | TTTTGTTAGACACACTGTAAATATTTAGAT[G]TTGTGTTATATTTACGAAAATGTTCCAAAT | A |
| 35 | CTAAACATCCAAAGAAGTTTTCTACACGAG[A]GAGAGGGAGAAAATTACTAATAACTTCCCC | G |
| 36 | ACAATGCATTTCATTTTACCAAGTTCAATG[T]TAGTCAGATTAGTCAACATTTCTATGTTTC | G |
| 37 | TTTCCTCTCCTATCTTAATTCTCTCTATCC[A]TACATTTAAAATATATATTAACAGTACATC | G |
| 38 | CTTACTGTAGATACATTTTTGTATCCATTA[A]ATATAACCAATCAACAGTGCAATGACCCTT | G |
| 39 | TGTATCCATTAAATATAACCAATCAACAGT[G]CAATGACCCTTTACAAATTGCTCATAAGTA | A |
| 40 | AGAAAGAAGGAAAGAAACAATATCAAAATA[G]TTTTTTTAGAATTTTAAAAAATAACAAATT | GT |
| 41 | ATAAAGGGTTGGAACCTACCAATAATATCC[AAATGAAAATGAGAGTTTATTTTTAATGTT]G | A |
| 42 | AGTGACTAAGTAAGAAAATTATGCTTTTAA[G]AAAACAAAGTGACGTGAGATTGTTGGAATA | GC |
| 43 | CTATGAAAAATTGTCTTCCTATAAGGTTGA[G]ATATATATATATAAATAAAAAGTTATTTT | GAT |
| 44 | ATTGGTTTATGATCCAACCATTAAACTGAA[T]CTCTCTCAAGCCAATGAGAGGTCGAGACTT | C |
| 45 | GAATGTTTTTTTAAACTAATGACAAAAGTA[C]GGTAGGTAGGAAAGAAAGGATAGAAATGGG | G |
| 46 | TGAACAACAAAACAAATAATAATAATAATA[A]AAAAAAACAGAAAAAAATTGGATAGCATTC | AT |

TABLE 13-continued

| SEQ ID NO: | Sequences of the disclosure<br>Sequence with polymorphism location noted by brackets | Polymorphism associated with disclosed phenotype |
|---|---|---|
| 47 | ATATTATTTTTTATGAAAAAATATGGATAG[A]ATAAAAATAGATGAGTACAACTTTAAGGGA | G |
| 48 | TTATGTTTTAGTCAAATTTAGAGGCTCCTA[G]ATATTTATTTGCCCATTGCTCCTTTGCTTC | C |
| 49 | TTGTGACCATTACATGACTCAATAGTTCCA[T]ATGACTTATATCGTCTACCTTAAAATTAAT | G |
| 50 | TCAAATGACCATTGGAAAACCTATAGCCCA[T]TGAGAGGCAGCCAATATAGTAATGCCTCTA | C |
| 51 | TTTTCATTATCCAATTTCGCTTCGATTTTA[C]AAAAAATTATATATTTTTAAGGAGAATCCA | CA |
| 52 | TCCAATTTCGCTTCGATTTTACAAAAAATT[A]TATATTTTTAAGGAGAATCCAAATAAACTT | C |
| 53 | ATGTCAATGAAATAGGTACTACTAGCATTT[C]TTAGGAGTTAATGAATGAAACATGTAACCT | T |
| 54 | CGAGACTTGAACCAAGGGTCATACCTTCTC[A]ATGGCACGAGAGGGGTTTTTGTTTATTGGT | T |
| 55 | GAGAGGGGTTTTTGTTTATTGGTTGGACCA[T]AACAGGTTGTTCATTGGAGGAGCATTGATA | TA |
| 56 | TTTTTGTTTATTGGTTGGACCATAACAGGT[T]GTTCATTGGAGGAGCATTGATATTTAAAGA | C |
| 57 | TTTTGCTAATGTACCGATATTTTGGGATTC[T]CAAATTAATTTGAGAAATGGTTCTGTAAAA | C |
| 58 | TTTGTTCATTTGATTATGATATATTAAGTT[A]AAAAACGCATGAATCTATTGGTTCACAATA | C |
| 59 | CACGTGCTTGGTGATTACAATCTATATTTT[TC]GCCCTTCTTTAAATGAACAAGATTAAGAT | T |
| 60 | TGGTGATTACAATCTATATTTTTCGCCCTT[C]TTTAAATGAACAAGATTAAGATACTCACGT | CT |
| 61 | TTCAAAATAGTAAAGGAAAATTACAAGAAA[T]ATTTTAACATGAAAACGTTTAAGAAAGTCA | G |
| 62 | AAATTACAAGAAATATTTTAACATGAAAAC[G]TTTAAGAAAGTCACTCACCAAACTTTACTA | A |
| 63 | GAAATTTCCAAATCAATTTTGTTATACTTT[C]TAAATAGTTTAATTATTTTGTTATTTTTAA | G |
| 64 | GAATTTGGATATTACAAGCATTCCAGAGCA[C]TTTGGAAAATTTGGAGTTGATTTGGAGCTA | A |
| 65 | TTTCTATTAATTTTAAAGGTAATGGTAATG[G]ATGACTATTTGAGAAATAATAATTAAGGAT | A |
| 66 | ATGGATGACTATTTGAGAAATAATAATTAA[G]GATATAACAACATTTAAAAAAGTTGCAAAT | A |
| 67 | TGTAGTTTTATCATTTATAATACTATATAT[C]ATATAAAATTTTGATTGGTTACTTGTTTTG | A |
| 68 | TTTTAGAAAAAAAAAAAGTTTATTTTCTCA[C]AAAAAAAAATTGTTTGTGATTTCCATACTT | CA |
| 69 | TATATATCATATAAAATTTTGATTGGTTAC[TTGTTTTGA]GTTTATGTATTGCACTCTTTTT | T |
| 70 | TTCCTTTCATTTCTTATATTTTAGATGTAT[T]GAGTTCATTCAAATAAAAGTATATGTATTA | C |
| 71 | GTTACATACATTATATCGGTTTAGAAAGAT[C]AGACCAATTTTTTTTAGAAAAAAATAGTTT | G |
| 72 | ACTATTATCACAAAGTAACTCTCAATAGTT[T]AGTCTAAACAATCATAATTGGTTTGTACTG | A |
| 73 | AAGCATACGGCATAAACTCTGAGAGTAAAG[C]GAGAAGAAATATTATGAATGAGGACCATGC | T |
| 74 | TGTTTCACATCCAACTTTCTTCTTTGTTAC[A]TACATTATATCGGTTTAGAAAGATCAGACC | C |
| 75 | ACATTATATCGGTTTAGAAAGATCAGACCA[AT]TTTTTTTAGAAAAAAATAGTTTTCAAAAA | A |
| 76 | CTACCAATATTTCTTTCTAAATTCTAATTA[T]TTGAATTTGGTGGGGTTTCTCAAATTCTTC | C |
| 77 | TGTTTTATTTATAAGTTTGATTGATTAATT[C]TTTTATTGCTTTAATTAAATTTAAATTTTA | T |
| 78 | ACATAATTCATGGCAAGAAAATTTCGTTCT[T]GTCAAAAGATTGTGTTTTAGAATAAAAGAA | C |
| 79 | AAAGTAGGTTTAGTTTCATTTTTAACATAT[C]TCTTCTTAAGGTTAAAACTATATTTCGTTT | T |
| 80 | AGTAGGTTTAGTTTCATTTTTAACATATCT[C]TTCTTAAGGTTAAAACTATATTTCGTTTTT | G |
| 81 | AGGTTTAGTTTCATTTTTAACATATCTCTT[C]TTAAGGTTAAAACTATATTTCGTTTTTTAT | G |
| 82 | TTTTTAGAAAAAAATAGTTTTCAAAAAGTT[A]CATTTTATTTTAAAATATGGAAAATTTTTC | G |

TABLE 13-continued

Sequences of the disclosure

| SEQ ID NO: | Sequence with polymorphism location noted by brackets | Polymorphism associated with disclosed phenotype |
|---|---|---|
| 83 | ATTAGTTCAAGAAAGGCTTCCCATAGCCTT[A]GCTCTTTCCCTCAATATGAACTTTTGAACC | C |
| 84 | TAAGGAAGAAGGGGAATTGTATTGTATTAT[T]GAAGGAGGTCGGGTTGTTCCTTTGCCTTGA | C |
| 85 | AGAGTTTACAAATATAGTAAAAGTAATTAT[A]ATAACAAAGTTCATGTCACTTGTATTTTTT | G |
| 86 | GATTTTACAAAAAATTATATATTTTTAAGG[A]GAATCCAAATAAACTTTTTTAAAAAAGAAT | T |
| 87 | ACTCGATAGTATATTCTATTAGATAATGCA[C]ACATTCATGTTTCAAATGACTTAGCTTATT | T |
| 88 | ATTCCAATTCAATTAATAAACCATTAAAAA[AG]AAGGAGTGGGGCTAAATTTGATTAATTAT | A |
| 89 | TTTTCACCTTTAAATATGTGCATGCACATG[T]CAAAAAAAAAAAAAAGCAATTATATGAGCA | G |
| 90 | AAATTATTTTTCTTTCCTCTTTTCATGTTT[C]TAATTTTTTTTAAAAAAAGACAAATTAGGG | T |
| 91 | TAATATCACAGTTTTCATTATCCAATTTCG[C]TTCGATTTTACAAAAAATTATATATTTTTA | T |
| 92 | AATATCACAGTTTTCATTATCCAATTTCGC[T]TCGATTTTACAAAAAATTATATATTTTTAA | C |
| 93 | TGAACAAGGTGCATTTCAAGTGGGCTACAA[G]ATTCGTCTTTTGGAATTTGATTCGGAAATT | A |
| 94 | GCAAATTCTAATTATAAAGGATAAAACCTC[G]ATGCTAAAAGCTGTTTTATACAACAATTTC | A |
| 95 | ATTGCTACAAAGATAATGAATGTTAGTGGA[G]CTAAAACATGGAAATATTTTTTTAAATAAT | A |
| 96 | AATTACAGAAACTGTTAATATTCAATCAAA[G]AAAAAACAGTCTATCACTGATACAGATCTA | A |
| 97 | AGATAATGAATGTTAGTGGAGCTAAAACAT[G]GAAATATTTTTTTAAATAATTTTAGTGTGT | C |
| 98 | GATAATGAATGTTAGTGGAGCTAAAACATG[G]AAATATTTTTTTAAATAATTTTAGTGTGTT | A |
| 99 | TAATGAATGTTAGTGGAGCTAAAACATGGA[A]ATATTTTTTTAAATAATTTTAGTGTGTTTA | G |
| 100 | TCGTTGCTATCCAAGTCACCGCCACTCCAT[C]TTGTCTCCGTTTGTTGGTTGCGATTTGTTA | CTGATCGA |
| 101 | TTTGGGATTCTCAAATTAATTTGAGAAATG[G]TTCTGTAAAATCTTTCATTACCTATGACTT | A |
| 102 | AATTTGAGAAATGGTTCTGTAAAATCTTTC[A]TTACCTATGACTTTTATCCCTTCACGTACT | G |
| 103 | GTTTGTAGAAGTACCACTTAGACACTTAGA[C]ACTTAACGTTTTGATTGAAAACTCTTGACA | T |
| 104 | GGTTGTAAACTGTGTTAGTCAATTTATGCA[C]AACCAACTGTCATTCACTTTCCGGCAGTTA | CA |
| 105 | TAATATAATTTTTTTATGAAAAGTATAGGG[G]TAAGAAGCAGGTAAAAATTCTCTCTACATG | A |
| 106 | GTACTAATTATTATTATTTGGGGTGGTGTT[GT]TTTTTTCTTTATTATTGTACAATTATTTT | G |
| 107 | TTGGATTAAACTAAAAAAAATAGATTTTCA[G]GTGAATGTATTGATGGAGTTGCTCAATTTA | A |
| 108 | AAGAAGATGTCAATGAAATAGGTACTACTA[G]CATTTCTTAGGAGTTAATGAATGAAACATG | A |

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, Radioimmune Assay (RIA), immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene, or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed “amplification”. In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 60° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. This combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

For example, the real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLID, Illumina GA/HiSeq, Ion PGM, Mi Seq, among others (Liu et al. 2012 Journal of Biomedicine and Biotechnology Volume 2012 ID 251364; Franca et al., 2002 Quarterly Reviews of Biophysics 35 μg. 169-200; Mardis 2008 Genomics and Human Genetics vol. 9 μg. 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full-service analysis tools capable of handling nucleic acid/protein marker extractions, detection, storage and analysis.

Quantitative Trait Loci

Breeding schemes of the present application can include crosses between donor and recipient plants. In some embodiments, said donor plants contain a gene or genes of interest which may confer the plant with a desirable phenotype. The recipient line can be an elite line having certain favorable traits for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

QTL (quantitative trait locus) mapping can be applied to determine the parts of the donor plant's genome conferring the desirable phenotype and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping,* 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared, and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R.G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92: 191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.;* 2(10):e245).

Genetic Complementation Test (Also Know as the "Cis-Trans" Test)

When genetic markers and/or phenotype-conferring mutations have not been identified, the complementation test can be used to determine whether two organisms, having the same recessive inherited phenotype, have mutations in the same genes or different genes.

For this test, two homozygous recessive organisms are crossed. If the mutations are in the same gene then both copies of the gene will be mutant in the $F_1$ offspring and they will exhibit the same phenotype as their parents. In this case, the exact mutations may be different (for example, a missense in one mutant and a nonsense in the other mutant), but both alleles of a single gene are mutant and therefore the recessive phenotype will be observed. In contrast, if the two mutants have homozygous recessive mutant alleles for two different genes, gene1−/− and gene2−/− for example, then the offspring will inherit a wild-type copy of gene1+ from the gene2−/− mutant and a wild-type copy of gene2 from the gene1−/− mutant parent, and the offspring will not exhibit the phenotype of the parental lines.

Tissue Culture

As it is well known in the art, tissue culture of cucumber can be used for the in vitro regeneration of cucumber plants. Tissues cultures of various tissues of cucumber and regeneration of plants therefrom are well known and published. By way of example, a tissue culture comprising organs has been used to produce regenerated plants as described in Girish-Chandel et al., *Advances in Plant Sciences.* 2000, 13:1, pgs. 11-17; Costa et al., *Plant Cell Report.* 2000, 19, pgs. 327-332; Plastira et al., *Acta Horticulturae.* 1997, 447, 231-234; Zagorska et al., *Plant Cell Report.* 1998, 17:12 pgs. 968-973; Asahura et al., *Breeding Science.* 1995, 45, pgs. 455-459; Chen et al., *Breeding Science.* 1994, 44:3, pgs. 257-262; Patil et al., *Plant and Tissue and Organ Culture.* 1994, 36, pgs. 255-258. It is clear from the literature that the state of the art is such that these methods of obtaining plants are routinely used and have a very high rate of success. Thus, another aspect of this disclosure is to provide cells which upon growth and differentiation produce cucumber plants having all the physiological and morphological characteristics of the varieties described herein.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollens, flowers, seeds, leaves, stems, roots, root tips, anthers, pistils, meristematic cells, axillary buds, ovaries, seed coats, endosperms, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference.

Commodity Plant Products

Plant parts of the varieties described herein can be stored and/or processed further. The disclosure thus, provides for a food or a feed product comprising one or more of such parts, such as canned, chopped, cooked, roasted, in a sauce, in a sandwich, pasted, pureed or concentrated, juiced, frozen, dried, pickled, or powdered cucumber fruit from the varieties described herein or from progeny of said variety, or from a derived variety, such as a plant having all but one, two, or three physiological and/or morphological characteristics of the varieties described herein. In some embodiments, the plant part is a cucumber fruit or part thereof and/or an extract from a fruit of the plant described herein comprising at least one cell of a variety described herein. The food or feed product may be fresh or processed, e.g., dried, grinded, powdered, pickled, chopped, cooked, roasted, in a sauce, in a sandwich, pasted, pureed or concentrated, juiced, pickled, canned, steamed, boiled, fried, blanched and/or frozen, etc.

In another aspect, the disclosure provides for a cucumber fruit of a variety described herein, or a part of a fruit of said variety. The fruit can be in any stage of maturity, for example, immature or mature. In another aspect, the disclosure provides for a container comprising or consisting of a plurality of harvested cucumber fruits or parts of fruits of said variety, or fruits of progeny thereof, or fruits of a derived variety. Marketable fruits are generally sorted by size and quality after harvest.

In another aspect, the plant, plant part, or seed of a variety described herein is inside one or more containers. For example, the disclosure provides containers such as cans, boxes, crates, bags, cartons, Modified Atmosphere Packaging, films (e.g., biodegradable films), etc. comprising a plant or a plant part (fresh and/or processed) or a seed of a variety described herein. In a particular aspect, the container comprises a plurality of seeds, or a plurality of plant parts, including seedless fruits. The plants, plant parts, or seeds may be disinfected, primed and/or treated with various compounds, such as seed coatings or crop protection compounds.

The seed stock and the seeds may be technically treated. The disclosure thus also comprises technically-treated seed stock and technically-treated seeds. The various embodiments of technically-treated seed stock are explained in detail in the following whereby the term seed stock also includes seeds: Technically-treated seed stock may be present in polished form. The outermost layer of the seed is thereby removed, so that the seed assumes a more rounded form. This is helpful in sowing, where an optimally uniform shape leads to a uniform distribution of the seed stock grains. Technically-treated seed stock furthermore encompasses pelleted seed stock. The seed stock is thereby embedded in a pelleting mass that protects the seed stock contained therein and leads to a larger mass, such that the pelleted seed stock shows a greater resistance capability with regard to wind drift and is thus less susceptible to being blown away by the wind, and, at the same time, a more precise positioning during sowing is enabled. In some embodiments, all pelleted seed stock grains of a batch or unit designated for sale have essentially the same shape and the same mass. Deviations of 5% in diameter and mass are possible. In some embodiments, the deviations do not exceed 1%.

As one of the main components, the pelleting mass may contain for example a mineral compound such as clay, bentonite, kaolin, humus and/or peat, for example. It is possible to add an adhesive material like polyacylamide. Additional possible components are cited in U.S. Pat. No. 4,067,141. Moreover, the pelleting mass may contain additional chemical agents that positively influence the cultivation in practice. These may be substances that are counted among fertilizing agents. These include compounds rich of one or more of the following elements: nitrogen, phosphorus and potassium (macronutrients). Therefore, the fertilizing ingredients may contain for example Nitrate nitrogen, Ammonium nitrogen, Magnesium Nitrate, Calcium Ammonium Nitrate, Mono Ammonium Phosphate, Mono Potassium Phosphate and Potassium Nitrate.

Furthermore, pelleting mass may contain fungicides, insecticides, and/or antifeedants. The fungicides may be thiram and/or hymexazol and/or other fungicides. The insecticide may be a substance from the neonicotinoid group. The substance from the neonicotinoid group is preferably imidacloprid (ATC Code: QP53AX17) and/or clothianidin (CAS number 210880-92-5). Furthermore, the insecticide may also be cyfluthrin (CAS number 68359-37-5), beta-cyfluthrin or tefluthrin. It is worth mentioned that the compound included in the dressing or pelleting mass are taken up by the plant and show systemic effect thereby providing suitable protection of the whole plant. Plants resulting from pelleted seed including one or more pesticides therefore differ from naturally occurring plants and show better performance under biotic stress conditions. In this context the disclosure also encompasses a mixture of a pelleting mass and a seed according to the disclosure. The disclosure also encompasses a method for producing a pelleted seed comprising the following steps: a) providing a cucumber plant seed comprising the nucleic acid according to the disclosure b) embedding the cucumber plant seed in a pelleting mass c) allow the pelleting mass to dry, wherein the seed may be optionally a primed or pregerminated seed or the seed may be allowed to be primed during step b).

The pelleted seed stock is a specific embodiment of dressed seed stock. In this context technically-treated seed stock encompasses also the dressed seed stock. However, the disclosure is not limited to pelleted seed stock, but, rather, may be applied with any form of dressed seed stock. The disclosure thus also relates to dressed seed stock, which includes pelleted seed stock, but is not limited to this. Dry dressing, wet dressing, and suspension dressing are thus also encompassed.

The dressing may thereby also contain at least one dye (coloring), such that the dressed seed stock may be quickly differentiated from undressed seed stock, and, furthermore, good visibility in the environment is ensured after sowing. The dressing may also contain those agrochemicals which are described in the context of the pilling mass. The disclosure includes thus such dressed seed stock whereby the dressing contains at least one anti-feedant such as an insecticide and/or at least one fungicide. Optionally, so called electronical dressing (dressing by application of electric energy) may be applied. However, electronic dressing is not a dressing in the strict sense of the word.

An additional form of technically-treated seed stock is encrusted seed stock. What is known as coating is also spoken of in this context as well as of seed stock treated with a coating. The difference to pelleted seed stock is that the seed grains retain their original shape, wherein this method is especially economical. The method is described in EP 0 334 258 A1, for example. An additional form of technically-treated seed stock is sprouted or primed seed stock. Sprouted seed stock is pretreated via a pre-germination, whereas primed seed stock has been pretreated via a priming ("germination"). Pre-germinated and primed seed stock have the advantage of a shorter emergence time. The point in time of the emergence after sowing is, at the same time, more strongly synchronized. This enables better agrotechnical processing during cultivation and especially during the harvest, and, additionally, increases the yield quantity. In pre-germination, the seed stock is germinated until the radicle exits the seed stock shell, and the process is subsequently stopped. In the priming, the process is stopped before the radicle exits the seed stock shell. Compared to pre germinated seed stock, seed stock that has been subjected to a priming is insensitive to the stress of a re-drying and, after such a re-drying, has a longer storage life in comparison to pre-germinated seed stock, for which a re-drying is generally not advised. In this context, technically pre-treated seed stock also includes primed and re-dried seed stock. The process of pre-germination is explained in U.S. Pat. No. 4,905,411 A. Various embodiments of priming are explained in EP 0 686 340 A1. In addition to this, it is also possible to simultaneously pill and prime seed stock in one process. This method is described in EP 2 002 702 B1. Primed seed stock which is moreover pelleted, is encompassed by the present disclosure.

The disclosure also encompasses a mixture containing the seed stock according to the seeds described herein, and a dressing mass as defined above. In some embodiments, the dressing mass is embodied as a pelleting mass, as defined above.

With storage of seed stock, storage conditions can be chosen that do not negatively affect the stability or storage life of the seed stock. For example, fluctuations in humidity may have a disadvantageous effect here. In some embodiments, the disclosure teaches a method for the storage of the seed stock in a bag or container that is simultaneously water-repellent and breathable. Such a bag or container may be designed as a carton or packing. Such a carton or packing may optionally possess an inner vapor barrier. If the carton or packing is designed as a duplex carton, its stability increases. A container, bag, carton or packing comprising the seed stock according to the disclosure, or technically-treated seed stock according to the disclosure, is likewise a part of the disclosure. It is likewise part of the disclosure to store seed stock according to the disclosure or technically-treated seed stock according to the disclosure in such a bag, container, packing or carton.

DEPOSIT INFORMATION

Deposit of 'HRZ-CS-24-0001H'

A deposit of the cucumber seed of this disclosure is maintained by Harmoniz Ltd. In addition, a sample of the hybrid cucumber seed of this disclosure was deposited with the National Collections of Industrial, Food and Marine Bacteria (NCIMB), NCIMB Ltd. Ferguson Building, Craibstone Estate, Bucksburn, Aberdeen, AB21 9YA Scotland on Dec. 17, 2024, and assigned NCIMB Accession No. 44490.

To satisfy the enablement requirements of 35 U.S.C. 112, and to certify that the deposit of the isolated strain of the present disclosure meets the criteria set forth in 37 CFR 1.801-1.809, Applicants hereby make the following statements regarding the deposited hybrid cucumber 'HRZ-CS-24-0001H' (deposited as NCIMB Accession No. 44490).

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become inviable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

Deposit of 'HRZ-CS-24-0003L'

A deposit of the cucumber seed of this disclosure designated 'HRZ-CS-24-0003L' is maintained by Harmoniz Ltd. In addition, a sample of the hybrid cucumber seed of this disclosure was deposited with the National Collections of Industrial, Food and Marine Bacteria (NCIMB), NCIMB Ltd. Ferguson Building, Craibstone Estate, Bucksburn, Aberdeen, AB21 9YA Scotland on Jan. 30, 2025, and assigned NCIMB Accession No. 44525.

To satisfy the enablement requirements of 35 U.S.C. 112, and to certify that the deposit of the seed of the present disclosure meets the criteria set forth in 37 CFR 1.801-1.809, Applicant hereby makes the following statements regarding the deposited hybrid cucumber 'HRZ-CS-24-0003L' (deposited as NCIMB Accession No. 44525).

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become inviable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

Deposit of 'HRZ-CS-24-0004L'

A deposit of the cucumber seed of this disclosure designated 'HRZ-CS-24-0004L' is maintained by Harmoniz Ltd. In addition, a sample of the hybrid cucumber seed of this disclosure was deposited with the National Collections of Industrial, Food and Marine Bacteria (NCIMB), NCIMB Ltd. Ferguson Building, Craibstone Estate, Bucksburn, Aberdeen, AB21 9YA Scotland on Jan. 30, 2025, and assigned NCIMB Accession No. 44526.

To satisfy the enablement requirements of 35 U.S.C. 112, and to certify that the deposit of the seed of the present disclosure meets the criteria set forth in 37 CFR 1.801-1.809, Applicant hereby makes the following statements regarding the deposited hybrid cucumber 'HRZ-CS-24-0004L' (deposited as NCIMB Accession No. 44526).

1. During the pendency of this application, access to the disclosure will be afforded to the Commissioner upon request;

2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become inviable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

EXAMPLES

The foregoing examples of the related art and limitations related therewith are intended to be illustrative and not exclusive. Other limitations of the related art will become apparent to those of skill in the art upon a reading of the specification.

Example 1—Introgressing the Genetic Trait for Small Fruit and Increased Fruit Number into Other Elite Cucumber Varieties The genetic trait for small prime fruit and increased fruit number can be transferred to other cucumber varieties via traditional breeding and/or marker assisted breeding. Plants comprising the genetic trait, for example, 'HRZ-CS-24-0003L', 'HRZ-CS-24-0004L', and 'HRZ-CS-24-0001H' can be induced to form male flowers by application of chemicals and methods known in the art. Examples of such chemicals include, but are not limited to, silver nitrate ($AgNO_3$), gibberellic acid ($GA_3$), silver thiosulphate ($Ag(S_2O_3)_2^{-3}$), 1-methylcyclopropene, 2-aminoethoxyvinyl glycine, pyrazinamide, and 2,5-norbornadiene, and combinations thereof (see Dhall R. et al., Standardized protocol for in situ and in vitro maintenance of newly developed parthenocarpic gynoecious cucumber inbred, *Brazilian Archives of Biology and Technology,* 2022 Vol. 65).

In this example, pollen from a male flower comprising the genetic trait for small prime fruit can be used to fertilize female flowers of other elite, commercial cucumber varieties. F1 offspring can then be repeatedly backcrossed to the elite parental line, and tested for the trait using the molecular markers disclosed herein, to obtain plants having essentially all the characteristics of the elite commercial line and the small fruit phenotype.

Example elite cucumber varieties are provided in Table 14 below.

TABLE 14

Example elite cucumber varieties

| Variety name | Type |
|---|---|
| 'Babylon' | Slicing |
| 'Carmen' | Pickling |
| 'Cool Breeze' | Fresh eating |
| 'Corinto' | Slicing |
| 'Dasher II' | Pickling |
| 'Diva' | Slicing |
| 'Envy' | Fresh eating |
| 'Euphoria' | Pickling |
| 'Excelsior' | Fresh eating |
| 'Fanfare' | Slicing |
| 'Green Finger' | Fresh eating |
| 'Green Light' | Pickling |
| 'Indy' | Slicing |
| 'Itachi' | Pickling |
| 'Iznik' | Fresh eating |
| 'Juno' | Slicing |
| 'Katrina' | Fresh eating |
| 'Little Leaf (H-19)' | Pickling |
| 'Lutfiye' | Slicing |
| 'Manny' | Pickling |
| 'Marketmore 76' | Fresh eating |
| 'Mini Munch' | Slicing |
| 'Monalisa' | Pickling |
| 'Nokya' | Fresh eating |
| 'Olympian' | Slicing |
| 'Passandra' | Pickling |
| 'Patio Snacker' | Fresh eating |
| 'Piccolino' | Slicing |
| 'Poinsett 76' | Pickling |
| 'Quirk' | Fresh eating |
| 'Quete' | Fresh eating |
| 'Qwerty' | Fresh eating |
| 'Rocky' | Slicing |
| 'Sassy' | Pickling |
| 'Socrates' | Fresh eating |
| 'Speedy' | Slicing |
| 'Summer Dance' | Pickling |
| 'Sweet Success' | Fresh eating |
| 'Tasty Green' | Slicing |
| 'Tasty Jade' | Pickling |
| 'Tosca' | Fresh eating |
| 'Turbo' | Slicing |
| 'Tyria' | Pickling |
| 'Unistar' | Fresh eating |
| 'Viper' | Slicing |
| 'Willowleaf' | Pickling |
| 'Xanthos' | Fresh eating |
| 'Yorkshire Fog' | Slicing |
| 'Zenith' | Pickling |
| 'Zesty' | Fresh eating |
| 'Zeus' | Slicing |

Example 2—Introducing a Desirable Trait into Hybrid Cucumber Variety 'HRZ-CS-24-0001H'

Additional desirable traits may be introduced into hybrid cucumber variety 'HRZ-CS-24-0001H' by several methods. For example, the desirable trait may be introduced into one or both of the parental lines of 'HRZ-CS-24-0001H' by backcross breeding, transformation, targeted genetic engineering, or random mutagenesis, followed by crossing to produce single locus conversion plants of hybrid 'HRZ-CS-24-0001H'.

Genetic transformation, targeted genetic engineering, or random mutagenesis of hybrid 'HRZ-CS-24-0001H' may also be used to introduce a desirable trait.

Example 3—Introducing a Desirable Trait into Cucumber Variety 'HRZ-CS-24-0003L'

Additional desirable traits may be introduced into cucumber variety 'HRZ-CS-24-0003L' by several methods. For example, the desirable trait may be introduced by backcross breeding, transformation, targeted genetic engineering, or random mutagenesis.

Example 4—Introducing a Desirable Trait into Cucumber Variety 'HRZ-CS-24-0004L'

Additional desirable traits may be introduced into cucumber variety 'HRZ-CS-24-0004L' by several methods. For example, the desirable trait may be introduced by backcross breeding, transformation, targeted genetic engineering, or random mutagenesis.

NUMBERED EMBODIMENTS

Embodiments for 'HRZ-CS-24-0001H'

1. A plant, plant part, or plant cell of hybrid cucumber variety 'HRZ-CS-24-0001H', wherein a representative sample of seed of said cucumber variety is deposited under NCIMB Accession No. 44490.
2. The plant part of embodiment 1, wherein the plant part is a leaf, a fruit, a pollen, an ovary, an ovule, an embryo sac, a stem, a scion, a root, a rootstock, or a cutting.
3. A seed that produces the plant of embodiment 1.
4. The seed of embodiment 3, wherein the seed has been technically treated.
5. The seed of embodiment 4, whereby the technical treatment is selected from the group consisting of: dressing, pelleting, encrustation, coloring, coating, priming, and combinations thereof.
6. A cucumber plant having all the physiological and morphological characteristics of the plant of embodiment 1, when grown under the same environmental conditions.
7. A cucumber plant or part thereof obtained from the plant of embodiment 1 which does not differ in any of the morphological and physiological characteristics of cucumber variety 'HRZ-CS-24-0001H' when grown under the same environmental conditions, and wherein a representative sample of seed of said variety is deposited under NCIMB Accession No. 44490.
8. A tissue culture of regenerable cells produced from the plant or plant part of any one of embodiments 1-2 or 6-7, wherein a cucumber plant regenerated from the tissue culture has all of the physiological and morphological characteristics of cucumber variety 'HRZ-CS-24-0001H' when grown in the same environmental conditions.
9. The tissue culture of embodiment 8, wherein the regenerable cells are obtained from a meristem, a cotyledon, a hypocotyl, a leaf, an anther, a root, a root tip, a pistil, a petiole, a flower, a stalk, or a stem.
10. A cucumber plant regenerated from the tissue culture of embodiment 8 or 9.
11. A method of producing the plant of embodiment 1, 6, or 7, the method comprising: vegetatively propagating at least a part of a plant of cucumber variety 'HRZ-CS-24-0001H', wherein a representative sample of seed of said cucumber variety is deposited under NCIMB Accession No. 44490.
12. A plant produced by the method of embodiment 11, wherein the plant has all the physiological and morphological characteristics of variety 'HRZ-CS-24-0001H' when grown under the same environmental conditions.
13. A method for producing a cucumber seed derived from 'HRZ-CS-24-0001H', the method comprising: a) crossing a first cucumber plant with a second cucumber plant and harvesting resultant cucumber seed, wherein the first cucumber plant and/or second cucumber plant is the cucumber plant of embodiment 1, 6, or 7, and wherein the first cucumber plant and/or the second cucumber plant has been treated with a chemical to induce male flowering.
14. The method of embodiment 13, wherein the chemical to induce male flowering is an agent inhibiting ethylene action.
15. The method of embodiment 14, wherein the agent inhibiting ethylene action is selected from silver nitrate, silver thiosulfate, gibberellic acid, 1-methylcyclopropene, and combinations thereof.
16. The method of any one of embodiments 13-15, further comprising the steps of:
   b) growing the seed produced by step a) to produce a progeny cucumber plant derived from 'HRZ-CS-24-0001H', and optionally treating the progeny cucumber plant with a chemical to induce male flowering;
   c) crossing the progeny cucumber plant derived from 'HRZ-CS-24-0001H' with itself or a second cucumber plant to produce a progeny seed of subsequent generation;
   d) growing the progeny seed of subsequent generation to produce a progeny plant of subsequent generation; and
   e) repeating steps c) and/or d) to produce a cucumber seed or plant further derived from 'HRZ-CS-24-0001H'.
17. The method of any one of embodiments 13-16, wherein the method further comprises use of a molecular marker to screen the first and/or second cucumber plant and/or any progeny plant for the presence of one or more polymorphisms selected from Table 5.
18. The method of any one of embodiments 13-16, wherein the method further comprises use of a molecular marker to screen the first and/or second cucumber plant and/or any progeny plant for the presence of one more polymorphisms selected from Table 7.
19. The method of any one of embodiments 13-16, wherein the method further comprises use of a molecular marker to screen the first and/or second cucumber plant and/or any progeny plant for the presence of one or more polymorphisms selected from Table 8.
20. The method of any one of embodiments 13-16, wherein the method further comprises use of a molecular marker to screen the first and/or second cucumber plant and/or any progeny plant for the presence of one more polymorphisms selected from Table 9.
21. The method of any one of embodiments 13-16, wherein the method further comprises use of a molecular marker to screen the first and/or second cucumber plant and/or any progeny plant for the presence of one more polymorphisms selected from Table 10, Table 11, and Table 12.
22. The method of any one of embodiments 17-21, wherein the method further comprises use of a molecular marker to screen the first and/or second cucumber plant and/or any progeny plant for the presence of one more polymorphisms selected from Table 6.
23. A method of introducing a desired trait into cucumber variety 'HRZ-CS-24-0001H', the method comprising introducing a single locus conversion conferring the desired trait into the plant, the plant part, or plant cell of any one of embodiments 1-2, or 6-7, thereby producing a plant of cucumber variety 'HRZ-CS-24-0001H' comprising the desired trait.

24. The method of embodiment 23, wherein the single locus conversion is introduced into the plant, plant part, or plant cell by a genetic transformation.
25. The method of embodiment 23, wherein the single locus conversion is introduced into the plant, plant part, or plant cell by a gene-editing technique.
26. The method of embodiment 25, wherein the gene-editing technique is a nuclease selected from the group consisting of zinc finger nuclease, transcription activator-like effector nuclease (TALEN), engineered homing endonuclease/meganuclease, and clustered regularly interspaced short palindromic repeat (CRISPR)-associated proteins (Cas).
27. The method of any one of embodiments 23-26, wherein the desired trait is male sterility, herbicide tolerance, insect resistance, pest resistance, disease resistance, powdery mildew resistance, environmental stress tolerance, delayed senescence, controlled ripening, modified carbohydrate metabolism, or modified protein metabolism.
28. A cucumber plant produced by the method of any one of embodiments 23-27, wherein the plant has the desired trait and otherwise all the physiological and morphological characteristics of cucumber variety 'HRZ-CS-24-0001H'.
29. A method of making doubled haploids of the plant or plant part of any one of embodiments 1-2, or 6-7, said method comprising making doubled haploid cells from haploid cells of the plant of cucumber variety 'HRZ-CS-24-0001H', wherein a representative sample of seed of said cucumber variety is deposited under NCIMB Accession No. 44490.
30. A protoplast produced from the plant cell of embodiment 1.
31. A composite plant comprising the scion or rootstock of embodiment 2.
32. A package comprising the plant or plant part of any one of embodiments 1-2, or 6-7.
33. The package of embodiment 32, wherein the plant part is a seedless cucumber fruit.
34. A food, a feed product, or a processed product comprising the plant part of embodiment 2, wherein the plant part comprises at least one cell of hybrid cucumber variety 'HRZ-CS-24-0001H'.
35. The food, the feed product, or the processed product of embodiment 34, wherein the plant part is non-viable.
36. A method of producing a cucumber fruit, said method comprising growing the plant of embodiment 1, 6, or 7, until it sets at least one fruit, and collecting the fruit.
37. A fruit produced by the method of embodiment 36.
38. The fruit of embodiment 37, wherein said fruit is between about 4.0 cm and about 6.5 cm in length.
39. The fruit of embodiment 37, wherein said fruit is between about 4.0 cm and about 6.0 cm in length.
40. The fruit of embodiment 37, wherein said fruit is approximately 5.0 cm in length.
41. The fruit of any one of embodiments 37-40, wherein said fruit has a diameter of between about 1.0 cm and about 2.0 cm.
42. The fruit of any one of embodiments 37-40, wherein said fruit has a diameter of between approximately 1.1 cm and approximately 1.7 cm.
43. The fruit of any one of embodiments 37-42, wherein said fruit has a weight of between about 9.0 grams and about 13.0 grams.
44. The fruit of any one of embodiments 37-42, wherein said fruit has a weight of between approximately 9.0 grams and approximately 10.0 grams.
45. A container comprising the fruit, or part thereof, of any one of embodiments 37-44, or the fruit produced by the method of embodiment 36.
46. A method of producing a cucumber plant with a desired trait, comprising mutating the plant, plant part, or plant cell of any one of embodiments 1-2, or 6-7.
47. A method for developing a cucumber plant in a cucumber breeding program, the method comprising applying at least one plant breeding technique to the plant of embodiment 1, 6, or 7.
48. The method of embodiment 47, wherein the plant breeding technique is selected from application of one or more chemicals to induce male flowers, selfing, recurrent selection, backcrossing, pedigree breeding, mass selection, mutation breeding, genetic marker enhanced selection, genetic transformation, and combinations thereof.
49. A method for producing a cucumber plant derived from hybrid cucumber variety 'HRZ-CS-24-0001H', the method comprising:
    propagating a vegetative cutting from a stock cucumber plant, thereby producing the cucumber plant derived from variety 'HRZ-CS-24-0001H', wherein the stock cucumber plant is a product of applying a plant breeding technique to 'HRZ-CS-24-0001H', wherein representative seed of the hybrid cucumber variety 'HRZ-CS-24-0001H' has been deposited under NCIMB Accession No. 44490.
50. A method for producing a cucumber seed derived from hybrid cucumber variety 'HRZ-CS-24-0001H', the method comprising:
    crossing a stock cucumber plant with itself or another cucumber plant, thereby producing the cucumber seed derived from hybrid cucumber variety 'HRZ-CS-24-0001H', wherein the stock cucumber plant is a product of applying a plant breeding technique to 'HRZ-CS-24-0001H', wherein a representative sample of seed of hybrid cucumber variety 'HRZ-CS-24-0001H' has been deposited under NCIMB Accession No. 44490.
51. The method of embodiment 49 or 50, wherein said plant breeding technique is recurrent selection.
52. The method of embodiment 49 or 50, wherein said plant breeding technique is mass selection.
53. The method of embodiment 49 or 50, wherein said plant breeding technique is hybridization.
54. The method of embodiment 49 or 50, wherein said plant breeding technique is open-pollination.
55. The method of embodiment 49 or 50, wherein said plant breeding technique is backcrossing.
56. The method of embodiment 49 or 50, wherein said plant breeding technique is pedigree breeding.
57. A method for producing nucleic acids, the method comprising isolating nucleic acids from the plant, plant part, or plant cell of any one of embodiments 1-2, or 6-7.
58. A seed of cucumber variety 'HRZ-CS-24-0001H', wherein a representative sample of seed of said cucumber variety 'HRZ-CS-24-0001H' is deposited under NCIMB Accession No. 44490.
59. The seed of embodiment 58, wherein the seed has been technically treated.
60. The seed of embodiment 59, whereby the technical treatment is selected from the group consisting of:

dressing, pelleting, encrustation, coloring, coating, priming, and combinations thereof.

61. A method of introducing a desired trait into hybrid cucumber variety 'HRZ-CS-24-0001H', the method comprising:
   introducing a single locus conversion conferring the desired trait into a parental line of hybrid cucumber variety 'HRZ-CS-24-0001H'; and
   crossing the parental lines having the single locus conversion conferring the desired trait to produce a hybrid cucumber plant having a desired trait and otherwise all the morphological and physiological traits of hybrid cucumber variety 'HRZ-CS-24-0001H'.
62. The method of embodiment 61, wherein the introducing a single locus conversion conferring the desired trait into a parental line comprises:
   a) crossing parental variety 'HRZ-CS-24-0003L' with a second cucumber plant comprising a desired trait to produce $F_1$ progeny plants, wherein a representative sample of seed of said parental variety 'HRZ-CS-24-0003L' is deposited under NCIMB Accession No. 44525;
   b) selecting $F_1$ progeny plants that have the desired trait to produce selected $F_1$ progeny plants;
   c) backcrossing selected $F_1$ progeny plants with parental variety 'HRZ-CS-24-0003L' to produce backcross progeny plants;
   d) selecting backcross progeny plants that have the desired trait; and
   e) repeating steps c) and d) one or more times in succession to produce selected second or higher backcross progeny plants that comprise the single locus conversion conferring the desired trait and otherwise comprise all the physiological and morphological characteristics of parental variety 'HRZ-CS-24-0003L'.
63. The method of embodiment 61, wherein the introducing a single locus conversion conferring the desired trait into a parental line comprises:
   a) crossing parental variety 'HRZ-CS-24-0004L' with a second cucumber plant comprising a desired trait to produce $F_1$ progeny plants, wherein a representative sample of seed of said parental variety 'HRZ-CS-24-0004L' is deposited under NCIMB Accession No. 44526;
   b) selecting $F_1$ progeny plants that have the desired trait to produce selected $F_1$ progeny plants;
   c) backcrossing selected $F_1$ progeny plants with parental variety 'HRZ-CS-24-0004L' to produce backcross progeny plants;
   d) selecting backcross progeny plants that have the desired trait; and
   e) repeating steps c) and d) one or more times in succession to produce selected second or higher backcross progeny plants that comprise the single locus conversion conferring the desired trait and otherwise comprise all the physiological and morphological characteristics of parental variety 'HRZ-CS-24-0004L'.
64. A prime cucumber fruit of hybrid cucumber variety 'HRZ-CS-24-0001H', wherein said fruit has:
   a length of between about 4 cm and about 6 cm;
   a diameter of between about 1 cm and about 2 cm; and
   a weight of between about 9 grams and about 13 grams, wherein representative seed of hybrid cucumber variety 'HRZ-CS-24-0001H' has been deposited under NCIMB Accession No. 44490.
65. The prime cucumber fruit of embodiment 64, wherein said fruit has a fruit juice with a total soluble solids of about 2.0° Brix.
66. The prime cucumber fruit of embodiment 64, wherein said fruit juice has a total soluble solids of between about 1.5° Brix and about 2.5° Brix.
67. The prime cucumber fruit of any one of embodiments 64-66, wherein said fruit further has at least one characteristic selected from:
   i) an absence of fruit sutures;
   ii) a crunchy texture; and
   iii) a light green color, RHS 140C.
68. The prime cucumber fruit of any one of embodiments 64-67, wherein said fruit has an increased volatile organic compound level when compared to cucumber variety 'Qwerty' or 'Quete' when grown and harvested under the same conditions.
69. The prime cucumber fruit of embodiment 68, wherein the increased volatile organic compounds comprise (E,Z)-2,6-nonadienal and (E)-2-nonenal.
70. The prime cucumber fruit of any one of embodiments 64-69, wherein said fruit has a water content of at least about 95%.
71. The prime cucumber fruit of any one of embodiments 64-70, wherein said fruit has a decreased cucurbitacin content when compared to cucumber variety 'Qwerty' or 'Quete' when grown and harvested under the same conditions.
72. A plant of hybrid cucumber variety 'HRZ-CS-24-0001H' comprising a transgene conferring a desired trait, a sample of seed of said variety having been deposited under NCIMB Accession No. 44490.
72. A method of producing a composite plant, the method comprising grafting a rootstock or a scion of hybrid cucumber variety 'HRZ-CS-24-0001H' to another plant, thereby producing a composite plant, wherein a representative sample of seed of said cucumber variety is deposited under NCIMB Accession No. 44490.
74. A composite plant produced by the method of embodiment 73.
75. A method for producing seed derived from hybrid cucumber plant 'HRZ-CS-24-0001H', the method comprising:
   applying a chemical to a plant of variety 'HRZ-CS-24-0001H' to induce male flower formation;
   growing the plant until it sets at least one fruit;
   harvesting the fruit; and
   harvesting at least one seed from the fruit.
76. The method of embodiment 75, wherein the chemical to induce male flowering is an agent inhibiting ethylene action.
77. The method of embodiment 76, wherein the agent inhibiting ethylene action is selected from silver nitrate, silver thiosulfate, gibberellic acid, 1-methylcyclopropene, and combinations thereof.
77.1 A method for producing hybrid cucumber variety 'HRZ-CS-24-0001H' seed, the method comprising crossing cucumber variety 'HRZ-CS-24-0003L', representative seed of 'HRZ-CS-24-0003L' having been deposited under NCIMB Accession No. 44525, with cucumber variety 'HRZ-CS-24-0004L', representative seed of 'HRZ-CS-24-0004L' having been deposited under NCIMB Accession No. 44526.

78. A plant cell from hybrid cucumber variety 'HRZ-CS-24-0001H', wherein representative seed of the variety has been deposited under NCIMB Accession No. 44490.
79. The plant cell of embodiment 78, wherein the plant cell is from a plant part selected from the group consisting of a seed, a meristem, a cotyledon, a hypocotyl, a leaf, an anther, a root, a root tip, a pistil, a petiole, a flower, a stalk, or a stem.
80. A plant cell of cucumber variety, which is a descendant of 'HRZ-CS-24-0001H', the descendant expressing the physiological and morphological characteristics of hybrid cucumber variety 'HRZ-CS-24-0001H' as determined at the 5% significance level when grown under substantially similar environmental conditions, wherein representative seed of hybrid cucumber variety 'HRZ-CS-24-0001H' has been deposited under NCIMB Accession No. 44490.
81. A plant cell from a tissue culture produced from the plant cell of any one of embodiments 78-80.
82. A plant cell from a cucumber plant regenerated from the tissue culture defined in embodiment 81, said plant expressing the physiological and morphological characteristics of variety 'HRZ-CS-24-0001H' listed in Table 1, as determined at the 5% significance level when grown under substantially similar environmental conditions, wherein representative seed of 'HRZ-CS-24-0001H' has been deposited under NCIMB Accession No. 44490.
83. A locus converted plant cell from a locus converted plant obtained by introducing a locus conversion into hybrid cucumber variety 'HRZ-CS-24-0001H', wherein the locus converted plant cell is the same as a plant cell from 'HRZ-CS-24-0001H' except for the locus conversion, and a plant grown from the plant cell expresses the physiological and morphological characteristics of hybrid cucumber variety 'HRZ-CS-24-0001H' listed in Table 1 as determined at the 5% significance level except for a trait conferred by the locus conversion, when grown under substantially similar environmental conditions, and wherein representative seed of the variety has been deposited under NCIMB Accession No. 44490.
84. The locus converted plant cell of embodiment 83, wherein the locus conversion comprises a transgene.
85. The locus converted plant cell of embodiment 83 or 84, wherein the locus conversion confers a trait selected from the group consisting of male sterility, herbicide tolerance, insect resistance, pest resistance, disease resistance, powdery mildew resistance, environmental stress tolerance, delayed senescence, controlled ripening, modified carbohydrate metabolism, or modified protein metabolism.
86. Use of a hybrid cucumber plant variety designated 'HRZ-CS-24-0001H', wherein representative seed of the variety has been deposited under NCIMB Accession No. 44490, for isolating nucleic acids from the variety.
87. Use of a hybrid cucumber plant variety designated 'HRZ-CS-24-0001H', wherein representative seed of the variety has been deposited under NCIMB Accession No. 44490, to produce a commodity plant product.
88. The use of embodiment 87, wherein the commodity plant product is selected from seed and harvested cucumber fruit.
89. The use of embodiment 88, wherein the harvested cucumber fruit is processed.
90. Use of a hybrid cucumber plant variety designated 'HRZ-CS-24-0001H', wherein representative seed of the variety has been deposited under NCIMB Accession No. 44490, to produce a cucumber fruit.
91. Use of a hybrid cucumber plant variety designated 'HRZ-CS-24-0001H', wherein representative seed of the variety has been deposited under NCIMB Accession No. 44490, to grow subsequent generations.
92. Use of a hybrid cucumber plant variety designated 'HRZ-CS-24-0001H', wherein representative seed of the variety has been deposited under NCIMB Accession No. 44490, for vegetative propagation.
93. Use of a hybrid cucumber plant variety designated 'HRZ-CS-24-0001H', wherein representative seed of the variety has been deposited under NCIMB Accession No. 44490, as a recipient of a conversion locus.
94. Use of a hybrid cucumber plant variety designated 'HRZ-CS-24-0001H', wherein representative seed of the variety has been deposited under NCIMB Accession No. 44490, to produce a genetic marker profile.

94.1 The use of embodiment 94, wherein the genetic marker profile comprises at least one polymorphism from selected from Table 5.

94.2 The use of embodiment 94, wherein the genetic marker profile comprises at least one polymorphism from selected from Table 7.

94.3 The use of embodiment 94, wherein the genetic marker profile comprises at least one polymorphism from selected from Table 8.

94.4 The use of embodiment 94, wherein the genetic marker profile comprises at least one polymorphism from selected from Table 9.

94.5 The use of embodiment 94, wherein the genetic marker profile comprises at least one polymorphism from selected from Table 10.

94.6 The use of embodiment 94, wherein the genetic marker profile comprises at least one polymorphism from selected from Table 11.

94.7 The use of embodiment 94, wherein the genetic marker profile comprises at least one polymorphism from selected from Table 12.

94.8 The use of any one of embodiments 94.2-94.7, wherein the genetic marker profile further comprises at least one polymorphism from selected from Table 6.

95. Use of a hybrid cucumber plant variety designated 'HRZ-CS-24-0001H', wherein representative seed of the variety has been deposited under NCIMB Accession No. 44490, as a source of seed, wherein said use comprises applying a chemical to induce male flower formation.
96. The use of embodiment 95, wherein the chemical to induce male flowering is an agent inhibiting ethylene action.
97. The use of embodiment 96, wherein the agent inhibiting ethylene action is selected from silver nitrate, silver thiosulfate, gibberellic acid, 1-methylcyclopropene, and combinations thereof.
98. Use of a hybrid cucumber plant variety designated 'HRZ-CS-24-0001H', wherein representative seed of the variety has been deposited under NCIMB Accession No. 44490, as a crop.
99. Use of a hybrid cucumber plant variety designated 'HRZ-CS-24-0001H', wherein representative seed of the variety has been deposited under NCIMB Accession No. 44490, as a recipient of a transgene.
100. Use of a hybrid cucumber plant variety designated 'HRZ-CS-24-0001H', wherein representative seed of the variety has been deposited under NCIMB Accession No. 44490, as a source of breeding material.

101. Use of a hybrid cucumber plant variety designated 'HRZ-CS-24-0001H', wherein representative seed of the variety has been deposited under NCIMB Accession No. 44490, for producing a plant derived from the variety.

102. Use of a hybrid cucumber plant variety designated 'HRZ-CS-24-0001H', wherein representative seed of the variety has been deposited under NCIMB Accession No. 44490, for producing a plant derived from the variety, wherein the plant derived from the variety produces prime fruit between approximately 4.0 cm and approximately 6.0 cm in length.

103. Use of embodiment 102, wherein the plant derived from the variety produces a greater number of fruits compared to similar commercial variety that is not derived from 'HRZ-CS-24-0001H'.

104. The use of any one of embodiments 101-103, wherein the plant derived from the variety is a first, second, third or fourth generation progeny plant.

104.1 Use of cucumber variety 'HRZ-CS-24-0003L' and cucumber variety 'HRZ-CS-24-0004L' to produce hybrid cucumber variety 'HRZ-CS-24-0001H' seed, representative sample of seed of cucumber variety 'HRZ-CS-24-0003L' having been deposited under NCIMB Accession No. 44525 and representative sample of seed of cucumber variety 'HRZ-CS-24-0004L' having been deposited under NCIMB Accession No. 44526.

Embodiments for 'HRZ-CS-24-0003L'

105. A plant, plant part, or plant cell of inbred cucumber variety 'HRZ-CS-24-0003L', wherein a representative sample of seed of said cucumber variety is deposited under NCIMB Accession No. 44525.

106. The plant part of embodiment 105, wherein the plant part is a leaf, a fruit, a pollen, an ovary, an ovule, an embryo sac, a stem, a scion, a root, a rootstock, or a cutting.

107. A seed that produces the plant of embodiment 105.

108. The seed of embodiment 107, wherein the seed has been technically treated.

109. The seed of embodiment 108, whereby the technical treatment is selected from the group consisting of: dressing, pelleting, encrustation, coloring, coating, priming, and combinations thereof.

110. A cucumber plant having all the physiological and morphological characteristics of the plant of embodiment 105, when grown under the same environmental conditions.

111. A cucumber plant or part thereof obtained from the plant of embodiment 105, which does not differ in any of the morphological and physiological characteristics of cucumber variety 'HRZ-CS-24-0003L' when grown under the same environmental conditions, and wherein a representative sample of seed of said variety is deposited under NCIMB Accession No. 44525.

112. A tissue culture of regenerable cells produced from the plant or plant part of any one of embodiments 105-106, or 110-111, wherein a cucumber plant regenerated from the tissue culture has all of the physiological and morphological characteristics of cucumber variety 'HRZ-CS-24-0003L' when grown in the same environmental conditions.

113. The tissue culture of embodiment 112, wherein the regenerable cells are obtained from a meristem, a cotyledon, a hypocotyl, a leaf, an anther, a root, a root tip, a pistil, a petiole, a flower, a stalk, or a stem.

114. A cucumber plant regenerated from the tissue culture of embodiment 112 or 113.

115. A method of producing the plant of embodiment 105, 110, or 111 the method comprising: vegetatively propagating at least a part of a plant of cucumber variety 'HRZ-CS-24-0003L', wherein a representative sample of seed of said cucumber variety is deposited under NCIMB Accession No. 44525.

116. A plant produced by the method of embodiment 115, wherein the plant has all the physiological and morphological characteristics of variety 'HRZ-CS-24-0003L' when grown under the same environmental conditions.

117. A method for producing a cucumber seed derived from 'HRZ-CS-24-0003L', the method comprising: a) crossing a first cucumber plant with a second cucumber plant and harvesting resultant cucumber seed, wherein the first cucumber plant and/or second cucumber plant is the cucumber plant of embodiment 105, 110, or 111, and wherein the first cucumber plant and/or the second cucumber plant has been treated with a chemical to induce male flowering.

118. The method of embodiment 117, wherein the chemical to induce male flowering is an agent inhibiting ethylene action.

119. The method of embodiment 118, wherein the agent inhibiting ethylene action is selected from silver nitrate, silver thiosulfate, gibberellic acid, 1-methylcyclopropene, and combinations thereof.

120. The method of any one of embodiments 117-119, further comprising the steps of:

b) growing the seed produced by step a) to produce a progeny cucumber plant derived from 'HRZ-CS-24-0003L', and optionally treating the progeny cucumber plant with a chemical to induce male flowering;

c) crossing the progeny cucumber plant derived from 'HRZ-CS-24-0003L' with itself or a second cucumber plant to produce a progeny seed of subsequent generation;

d) growing the progeny seed of subsequent generation to produce a progeny plant of subsequent generation; and e) repeating steps c) and/or d) to produce a cucumber seed or plant further derived from 'HRZ-CS-24-0003L'.

121. The method of any one of embodiments 117-120, wherein the method further comprises use of a molecular marker to screen the first and/or second cucumber plant and/or any progeny plant for the presence of one or more polymorphisms selected from Table 5.

122. The method of any one of embodiments 117-120, wherein the method further comprises use of a molecular marker to screen the first and/or second cucumber plant and/or any progeny plant for the presence of one more polymorphisms selected from Table 7.

123. The method of any one of embodiments 117-120, wherein the method further comprises use of a molecular marker to screen the first and/or second cucumber plant and/or any progeny plant for the presence of one or more polymorphisms selected from Table 8.

124. The method of any one of embodiments 117-120, wherein the method further comprises use of a molecular marker to screen the first and/or second cucumber plant and/or any progeny plant for the presence of one more polymorphisms selected from Table 9.

125. The method of any one of embodiments 117-120, wherein the method further comprises use of a molecular marker to screen the first and/or second cucumber plant and/or any progeny plant for the presence of one more polymorphisms selected from Table 10, Table 11, and Table 12.

126. The method of any one of embodiments 121-125, wherein the method further comprises use of a molecular marker to screen the first and/or second cucumber plant and/or any progeny plant for the presence of one more polymorphisms selected from Table 6.

127. A method of introducing a desired trait into cucumber variety 'HRZ-CS-24-0003L', the method comprising introducing a single locus conversion conferring the desired trait into the plant, the plant part, or plant cell of any one of embodiments 105-106, or 110-111, thereby producing a plant of cucumber variety 'HRZ-CS-24-0003L' comprising the desired trait.

128. The method of embodiment 127, wherein the single locus conversion is introduced into the plant, plant part, or plant cell by a genetic transformation.

129. The method of embodiment 127, wherein the single locus conversion is introduced into the plant, plant part, or plant cell by a gene-editing technique.

130. The method of embodiment 129, wherein the gene-editing technique is a nuclease selected from the group consisting of zinc finger nuclease, transcription activator-like effector nuclease (TALEN), engineered homing endonuclease/meganuclease, and clustered regularly interspaced short palindromic repeat (CRISPR)-associated proteins (Cas).

131. The method of any one of embodiments 127-130, wherein the desired trait is male sterility, herbicide tolerance, insect resistance, pest resistance, disease resistance, powdery mildew resistance, environmental stress tolerance, delayed senescence, controlled ripening, modified carbohydrate metabolism, or modified protein metabolism.

132. A cucumber plant produced by the method of embodiment 127-131, wherein the plant has the desired trait and otherwise all the physiological and morphological characteristics of cucumber variety 'HRZ-CS-24-0003L'.

133. A method of making doubled haploids of the plant or plant part of any one of embodiments 105-106, or 110-111 said method comprising making doubled haploid cells from haploid cells of the plant of cucumber variety 'HRZ-CS-24-0003L', wherein a representative sample of seed of said cucumber variety is deposited under NCIMB Accession No. 44525.

134. A protoplast produced from the plant cell of embodiment 105.

135. A composite plant comprising the scion or rootstock of embodiment 106.

136. A package comprising the plant or plant part of any one of embodiments 105-106, or 110-111.

137. The package of embodiment 136, wherein the plant part is a seedless cucumber fruit.

138. A food, a feed product, or a processed product comprising the plant part of embodiment 106, wherein the plant part comprises at least one cell of inbred cucumber variety 'HRZ-CS-24-0003L'.

139. The food, the feed product, or the processed product of embodiment 138, wherein the plant part is nonviable.

140. A method of producing a cucumber fruit, said method comprising growing the plant of embodiment 105, 110, or 111, until it sets at least one fruit, and collecting the fruit.

141. A fruit produced by the method of embodiment 140.

142. The fruit of embodiment 141, wherein said fruit is between about 4.0 cm and about 5.0 cm in length.

143. The fruit of embodiment 141 or 142, wherein said fruit has a diameter of between about 1.1 cm and about 1.5.

144. The fruit of any one of embodiments 141-143, wherein said fruit has a weight of between about 7.0 grams and about 10.0 grams.

145. A container comprising the fruit, or part thereof, of any one of embodiments 141-144, or the fruit produced by the method of embodiment 140.

146. A method of producing a cucumber plant with a desired trait, comprising mutating the plant, plant part, or plant cell of any one of embodiments 105-106, or 110-111.

147. A method for developing a cucumber plant in a cucumber breeding program, the method comprising applying at least one plant breeding technique to the plant of embodiment 105, 110, or 111.

148. The method of embodiment 147, wherein the plant breeding technique is selected from application of one or more chemicals to induce male flowers, selfing, recurrent selection, backcrossing, pedigree breeding, mass selection, mutation breeding, genetic marker enhanced selection, genetic transformation, and combinations thereof.

149. A method for producing a cucumber plant derived from inbred cucumber variety 'HRZ-CS-24-0003L', the method comprising:

propagating a vegetative cutting from a stock cucumber plant, thereby producing the cucumber plant derived from variety 'HRZ-CS-24-0003L', wherein the stock cucumber plant is a product of applying a plant breeding technique to 'HRZ-CS-24-0003L', wherein representative seed of the inbred cucumber variety 'HRZ-CS-24-0003L' has been deposited under NCIMB Accession No. 44525.

150. A method for producing a cucumber seed derived from inbred cucumber variety 'HRZ-CS-24-0003L', the method comprising:

crossing a stock cucumber plant with itself or another cucumber plant, thereby producing the cucumber seed derived from inbred cucumber variety 'HRZ-CS-24-0003L', wherein the stock cucumber plant is a product of applying a plant breeding technique to 'HRZ-CS-24-0003L', wherein a representative sample of seed of inbred cucumber variety 'HRZ-CS-24-0003L' has been deposited under NCIMB Accession No. 44525.

151. The method of embodiment 149 or 150, wherein said plant breeding technique is recurrent selection.

152. The method of embodiment 149 or 150, wherein said plant breeding technique is mass selection.

153. The method of embodiment 149 or 150, wherein said plant breeding technique is hybridization.

154. The method of embodiment 149 or 150, wherein said plant breeding technique is open-pollination.

155. The method of embodiment 149 or 150, wherein said plant breeding technique is backcrossing.

156. The method of embodiment 149 or 150, wherein said plant breeding technique is pedigree breeding.

157. A method for producing nucleic acids, the method comprising isolating nucleic acids from the plant, plant part, or plant cell of any one of embodiments 105-106, or 110-111.

158. A seed of cucumber variety 'HRZ-CS-24-0003L', wherein a representative sample of seed of said cucumber variety 'HRZ-CS-24-0003L' is deposited under NCIMB Accession No. 44525.

159. The seed of embodiment 158, wherein the seed has been technically treated.

160. The seed of embodiment 159, whereby the technical treatment is selected from the group consisting of: dressing, pelleting, encrustation, coloring, coating, priming, and combinations thereof.

161. A method of introducing a desired trait into inbred cucumber variety 'HRZ-CS-24-0003L', the method comprising:

a) crossing cucumber variety 'HRZ-CS-24-0003L' with a second cucumber plant comprising a desired trait to produce $F_1$ progeny plants, wherein a representative sample of seed of said cucumber variety 'HRZ-CS-24-0003L' is deposited under NCIMB Accession No. 44525;

b) selecting $F_1$ progeny plants that have the desired trait to produce selected $F_1$ progeny plants;

c) backcrossing selected $F_1$ progeny plants with cucumber variety 'HRZ-CS-24-0003L' to produce backcross progeny plants;

d) selecting backcross progeny plants that have the desired trait; and e) repeating steps c) and d) one or more times in succession to produce selected second or higher backcross progeny plants that comprise the desired trait and otherwise all the physiological and morphological characteristics of cucumber variety 'HRZ-CS-24-0003L'.

162. A cucumber plant produced by the method of embodiment 161, wherein the plant has the desired trait and otherwise all the physiological and morphological characteristics of cucumber variety 'HRZ-CS-24-0003L'.

163. A prime seedless cucumber fruit of inbred cucumber variety 'HRZ-CS-24-0003L', wherein said fruit has:

a length of between about 4 cm and about 5 cm;

a diameter of between about 1.0 cm and about 1.5 cm; and a weight of between about 7 grams and about 10 grams, wherein representative seed of inbred cucumber variety 'HRZ-CS-24-0003L' has been deposited under NCIMB Accession No. 44525.

164. The prime cucumber fruit of embodiment 163, wherein said fruit has a fruit juice with a total soluble solids of about 2.0° Brix.

165. The prime cucumber fruit of embodiment 163, wherein said fruit juice has a total soluble solids of between about 1.5° Brix and about 2.5° Brix.

166. The prime cucumber fruit of any one of embodiments 163-165, wherein said fruit further has at least one characteristic selected from:

i) an absence of fruit sutures; and ii) a crunchy texture.

167. The prime cucumber fruit of embodiment 163, wherein said fruit has an increased volatile organic compound level when compared to cucumber variety 'Qwerty' or 'Quete' when grown and harvested under the same conditions.

168. The prime cucumber fruit of embodiment 167, wherein the increased volatile organic compounds comprise (E,Z)-2,6-nonadienal and (E)-2-nonenal.

169. The prime cucumber fruit of any one of embodiments 163-168, wherein said fruit has a water content of at least about 95%.

170. The prime cucumber fruit of any one of embodiments 163-169, wherein said fruit has a decreased cucurbitacin content when compared to cucumber variety 'Qwerty' or 'Quete' when grown and harvested under the same conditions.

171. A plant of inbred cucumber variety 'HRZ-CS-24-0003L' comprising a transgene conferring a desired trait, a sample of seed of said variety having been deposited under NCIMB Accession No. 44525.

172. A method of producing a composite plant, the method comprising grafting a rootstock or a scion of inbred cucumber variety 'HRZ-CS-24-0003L' to another plant, thereby producing a composite plant, wherein a representative sample of seed of said cucumber variety is deposited under NCIMB Accession No. 44525.

173. A composite plant produced by the method of embodiment 172.

174. A method for producing seed derived from cucumber variety 'HRZ-CS-24-0003L', the method comprising:

applying a chemical to a plant of variety 'HRZ-CS-24-0003L' to induce male flower formation;

growing the plant until it sets at least one fruit;

harvesting the fruit; and harvesting at least one seed from the fruit.

175. The method of embodiment 174, wherein the chemical to induce male flowering is an agent inhibiting ethylene action.

176. The method of embodiment 175, wherein the agent inhibiting ethylene action is selected from silver nitrate, silver thiosulfate, gibberellic acid, 1-methylcyclopropene, and combinations thereof.

177. A plant cell from inbred cucumber variety 'HRZ-CS-24-0003L', wherein representative seed of the variety has been deposited under NCIMB Accession No. 44525.

178. The plant cell of embodiment 177, wherein the plant cell is from a plant part selected from the group consisting of a seed, a meristem, a cotyledon, a hypocotyl, a leaf, an anther, a root, a root tip, a pistil, a petiole, a flower, a stalk, or a stem.

179. A plant cell of cucumber variety, which is a descendant of 'HRZ-CS-24-0003L', the descendant expressing the physiological and morphological characteristics of inbred cucumber variety 'HRZ-CS-24-0003L' as determined at the 5% significance level when grown under substantially similar environmental conditions, wherein representative seed of inbred cucumber variety 'HRZ-CS-24-0003L' has been deposited under NCIMB Accession No. 44525.

180. A plant cell from a tissue culture produced from the plant cell of any one of embodiments 177-179.

181. A plant cell from a cucumber plant regenerated from the tissue culture defined in embodiment 180, said plant expressing the physiological and morphological characteristics of variety 'HRZ-CS-24-0003L' listed in Table 1, as determined at the 5% significance level when grown under substantially similar environmental conditions, wherein representative seed of 'HRZ-CS-24-0003L' has been deposited under NCIMB Accession No. 44525.

182. A locus converted plant cell from a locus converted plant obtained by introducing a locus conversion into inbred cucumber variety 'HRZ-CS-24-0003L', wherein the locus converted plant cell is the same as a plant cell from 'HRZ-CS-24-0003L' except for the locus conversion, and a plant grown from the plant cell expresses the physiological and morphological characteristics of inbred cucumber variety 'HRZ-CS-24-0003L' listed in Table 1 as determined at the 5% significance level except for a trait conferred by the locus conversion, when grown under substantially similar environmental conditions, and wherein representative seed of the variety has been deposited under NCIMB Accession No. 44525.

183. The locus converted plant cell of embodiment 182, wherein the locus conversion comprises a transgene.

184. The locus converted plant cell of embodiment 182 or 183, wherein the locus conversion confers a trait selected from the group consisting of male sterility, herbicide tolerance, insect resistance, pest resistance, disease resistance, powdery mildew resistance, environmental stress tolerance, delayed senescence, controlled ripening, modified carbohydrate metabolism, or modified protein metabolism.

185. Use of a cucumber plant variety designated 'HRZ-CS-24-0003L', wherein representative seed of the variety has been deposited under NCIMB Accession No. 44525, for isolating nucleic acids from the variety.

186. Use of a cucumber plant variety designated 'HRZ-CS-24-0003L', wherein representative seed of the variety has been deposited under NCIMB Accession No. 44525, to produce a commodity plant product.

187. The use of embodiment 186, wherein the commodity plant product is selected from seed and harvested cucumber fruit.

188. The use of embodiment 187, wherein the harvested cucumber fruit is processed.

189. Use of a cucumber plant variety designated 'HRZ-CS-24-0003L', wherein representative seed of the variety has been deposited under NCIMB Accession No. 44525, to produce a cucumber fruit.

190. Use of a cucumber plant variety designated 'HRZ-CS-24-0003L', wherein representative seed of the variety has been deposited under NCIMB Accession No. 44525, to grow subsequent generations.

191. Use of a cucumber plant variety designated 'HRZ-CS-24-0003L', wherein representative seed of the variety has been deposited under NCIMB Accession No. 44525, for vegetative propagation.

192. Use of a cucumber plant variety designated 'HRZ-CS-24-0003L', wherein representative seed of the variety has been deposited under NCIMB Accession No. 44525, as a recipient of a conversion locus.

193. Use of a cucumber plant variety designated 'HRZ-CS-24-0003L', wherein representative seed of the variety has been deposited under NCIMB Accession No. 44525, to produce a genetic marker profile.

193.1 The use of embodiment 193, wherein the genetic marker profile comprises at least one polymorphism from Table 5.

193.2 The use of embodiment 193, wherein the genetic marker profile comprises at least one polymorphism from selected from Table 7.

193.3 The use of embodiment 193, wherein the genetic marker profile comprises at least one polymorphism from selected from Table 8.

193.4 The use of embodiment 193, wherein the genetic marker profile comprises at least one polymorphism from selected from Table 9.

193.5 The use of embodiment 193, wherein the genetic marker profile comprises at least one polymorphism from selected from Table 10.

193.6 The use of embodiment 193, wherein the genetic marker profile comprises at least one polymorphism from selected from Table 11.

193.7 The use of embodiment 193, wherein the genetic marker profile comprises at least one polymorphism from selected from Table 12.

193.8 The use of any one of embodiments 193.2-193.7, wherein the genetic marker profile further comprises at least one polymorphism from selected from Table 6.

194. Use of a cucumber plant variety designated 'HRZ-CS-24-0003L', wherein representative seed of the variety has been deposited under NCIMB Accession No. 44525, as a source of seed, wherein said use comprises applying a chemical to induce male flower formation.

196. The use of embodiment 195, wherein the chemical to induce male flowering is an agent inhibiting ethylene action.

197. The use of embodiment 196, wherein the agent inhibiting ethylene action is selected from silver nitrate, silver thiosulfate, gibberellic acid, 1-methylcyclopropene, and combinations thereof.

197. Use of a cucumber plant variety designated 'HRZ-CS-24-0003L', wherein representative seed of the variety has been deposited under NCIMB Accession No. 44525, as a crop.

198. Use of a cucumber plant variety designated 'HRZ-CS-24-0003L', wherein representative seed of the variety has been deposited under NCIMB Accession No. 44525, as a recipient of a transgene.

199. Use of a cucumber plant variety designated 'HRZ-CS-24-0003L', wherein representative seed of the variety has been deposited under NCIMB Accession No. 44525, as a source of breeding material.

200. Use of a cucumber plant variety designated 'HRZ-CS-24-0003L', wherein representative seed of the variety has been deposited under NCIMB Accession No. 44525, for producing a plant derived from the variety.

201. Use of a cucumber plant variety designated 'HRZ-CS-24-0003L', wherein representative seed of the variety has been deposited under NCIMB Accession No. 44525, for producing a plant derived from the variety, wherein the plant derived from the variety produces prime fruit between approximately 4.0 cm and approximately 6.0 cm in length.

202. Use of embodiment 201, wherein the plant derived from the variety produces a greater number of fruit compared to a similar commercial variety that is not derived from 'HRZ-CS-24-0003L'

203. The use of any one of embodiments 200-202, wherein the plant derived from the variety is a first, second, third or fourth generation progeny plant.

Embodiments for 'HRZ-CS-24-0004L'

204. A plant, plant part, or plant cell of inbred cucumber variety 'HRZ-CS-24-0004L', wherein a representative sample of seed of said cucumber variety is deposited under NCIMB Accession No. 44526.

205. The plant part of embodiment 204, wherein the plant part is a leaf, a fruit, a pollen, an ovary, an ovule, an embryo sac, a stem, a scion, a root, a rootstock, or a cutting.

206. A seed that produces the plant of embodiment 204.

207. The seed of embodiment 206, wherein the seed has been technically treated.
208. The seed of embodiment 207, whereby the technical treatment is selected from the group consisting of: dressing, pelleting, encrustation, coloring, coating, priming, and combinations thereof.
209. A cucumber plant having all the physiological and morphological characteristics of the plant of embodiment 204, when grown under the same environmental conditions.
210. A cucumber plant or part thereof obtained from the plant of embodiment 204, which does not differ in any of the morphological and physiological characteristics of cucumber variety 'HRZ-CS-24-0004L' when grown under the same environmental conditions, and wherein a representative sample of seed of said variety is deposited under NCIMB Accession No. 44526.
211. A tissue culture of regenerable cells produced from the plant or plant part of any one of embodiments 204-205, or 209-210, wherein a cucumber plant regenerated from the tissue culture has all of the physiological and morphological characteristics of cucumber variety 'HRZ-CS-24-0004L' when grown in the same environmental conditions.
212. The tissue culture of embodiment 211, wherein the regenerable cells are obtained from a meristem, a cotyledon, a hypocotyl, a leaf, an anther, a root, a root tip, a pistil, a petiole, a flower, a stalk, or a stem.
213. A cucumber plant regenerated from the tissue culture of embodiment 211 or 212.
214. A method of producing the plant of embodiment 204, 209, or 210, the method comprising: vegetatively propagating at least a part of a plant of cucumber variety 'HRZ-CS-24-0004L', wherein a representative sample of seed of said cucumber variety is deposited under NCIMB Accession No. 44526.
215. A plant produced by the method of embodiment 214, wherein the plant has all the physiological and morphological characteristics of variety 'HRZ-CS-24-0004L' when grown under the same environmental conditions.
216. A method for producing a cucumber seed derived from 'HRZ-CS-24-0004L', the method comprising: a) crossing a first cucumber plant with a second cucumber plant and harvesting resultant cucumber seed, wherein the first cucumber plant and/or second cucumber plant is the cucumber plant of embodiment 204, 209, or 210, and wherein the first cucumber plant and/or the second cucumber plant has been treated with a chemical to induce male flowering.
217. The method of embodiment 216, wherein the chemical to induce male flowering is an agent inhibiting ethylene action.
218. The method of embodiment 217, wherein the agent inhibiting ethylene action is selected from silver nitrate, silver thiosulfate, gibberellic acid, 1-methylcyclopropene, and combinations thereof.
219. The method of any one of embodiments 216-218, further comprising the steps of:
  - b) growing the seed produced by step a) to produce a progeny cucumber plant derived from 'HRZ-CS-24-0004L', and optionally treating the progeny cucumber plant with a chemical to induce male flowering;
  - c) crossing the progeny cucumber plant derived from 'HRZ-CS-24-0004L' with itself or a second cucumber plant to produce a progeny seed of subsequent generation;
  - d) growing the progeny seed of subsequent generation to produce a progeny plant of subsequent generation; and
  - e) repeating steps c) and/or d) to produce a cucumber seed or plant further derived from 'HRZ-CS-24-0004L'
220. The method of any one of embodiments 216-219, wherein the method further comprises use of a molecular marker to screen the first and/or second cucumber plant and/or any progeny plant for the presence of one or more polymorphisms selected from Table 5.
221. The method of any one of embodiments 216-219, wherein the method further comprises use of a molecular marker to screen the first and/or second cucumber plant and/or any progeny plant for the presence of one more polymorphisms selected from Table 7.
222. The method of any one of embodiments 216-219, wherein the method further comprises use of a molecular marker to screen the first and/or second cucumber plant and/or any progeny plant for the presence of one or more polymorphisms selected from Table 8.
223. The method of any one of embodiments 216-219, wherein the method further comprises use of a molecular marker to screen the first and/or second cucumber plant and/or any progeny plant for the presence of one more polymorphisms selected from Table 9.
224. The method of any one of embodiments 216-219, wherein the method further comprises use of a molecular marker to screen the first and/or second cucumber plant and/or any progeny plant for the presence of one more polymorphisms selected from Table 10, Table 11, and Table 12.
225. The method of any one of embodiments 220-224, wherein the method further comprises use of a molecular marker to screen the first and/or second cucumber plant and/or any progeny plant for the presence of one more polymorphisms selected from Table 6.
226. A method of introducing a desired trait into cucumber variety 'HRZ-CS-24-0004L', the method comprising introducing a single locus conversion conferring the desired trait into the plant, the plant part, or plant cell of any one of embodiments 204-205, or 209-210, thereby producing a plant of cucumber variety 'HRZ-CS-24-0004L' comprising the desired trait.
227. The method of embodiment 226, wherein the single locus conversion is introduced into the plant, plant part, or plant cell by a genetic transformation.
228. The method of embodiment 226, wherein the single locus conversion is introduced into the plant, plant part, or plant cell by a gene-editing technique.
229. The method of embodiment 228, wherein the gene-editing technique is a nuclease selected from the group consisting of zinc finger nuclease, transcription activator-like effector nuclease (TALEN), engineered homing endonuclease/meganuclease, and clustered regularly interspaced short palindromic repeat (CRISPR)-associated proteins (Cas).
230. The method of any one of embodiments 226-229, wherein the desired trait is male sterility, herbicide tolerance, insect resistance, pest resistance, disease resistance, powdery mildew resistance, environmental stress tolerance, delayed senescence, controlled ripening, modified carbohydrate metabolism, or modified protein metabolism.
231. A cucumber plant produced by the method of any one of embodiments 226-230, wherein the plant has the desired trait and otherwise all the physiological and morphological characteristics of cucumber variety 'HRZ-CS-24-0004L'.

232. A method of making doubled haploids of the plant or plant part of any one of embodiments 204-205, or 209-210, said method comprising making doubled haploid cells from haploid cells of the plant of cucumber variety 'HRZ-CS-24-0004L', wherein a representative sample of seed of said cucumber variety is deposited under NCIMB Accession No. 44526.

233. A protoplast produced from the plant cell of embodiment 204.

234. A composite plant comprising the scion or rootstock of embodiment 205.

235. A package comprising the plant or plant part of any one of embodiments 204-205, or 209-210.

236. The package of embodiment 235, wherein the plant part is a seedless cucumber fruit.

237. A food, a feed product, or a processed product comprising the plant part of embodiment 205, wherein the plant part comprises at least one cell of inbred cucumber variety 'HRZ-CS-24-0004L'.

238. The food, the feed product, or the processed product of embodiment 237, wherein the plant part is nonviable.

239. A method of producing a cucumber fruit, said method comprising growing plant of embodiment 204, 209, or 210, until it sets at least one fruit, and collecting the fruit.

240. A fruit produced by the method of embodiment 239.

241. The fruit of embodiment 240, wherein said fruit is between about 5.0 cm and about 6.5 cm in length.

242. The fruit of embodiment 240 or 241, wherein said fruit has a diameter of between about 1.1 cm and about 1.5.

243. The fruit of any one of embodiments 240-242, wherein said fruit has a weight of between about 10.0 grams and about 13.0 grams.

244. A container comprising the fruit, or part thereof, of any one of embodiments 240-243, or a fruit produced by the method of embodiment 239.

245. A method of producing a cucumber plant with a desired trait, comprising mutating the plant, plant part, or plant cell of any one of embodiments 204-205, or 209-210.

246. A method for developing a cucumber plant in a cucumber breeding program, the method comprising applying at least one plant breeding technique to the plant of embodiment 204, 209, or 210.

247. The method of embodiment 246, wherein the plant breeding technique is selected from application of one or more chemicals to induce male flowers, selfing, recurrent selection, backcrossing, pedigree breeding, mass selection, mutation breeding, genetic marker enhanced selection, genetic transformation, and combinations thereof.

248. A method for producing a cucumber plant derived from inbred cucumber variety 'HRZ-CS-24-0004L', the method comprising:

propagating a vegetative cutting from a stock cucumber plant, thereby producing the cucumber plant derived from variety 'HRZ-CS-24-0004L', wherein the stock cucumber plant is a product of applying a plant breeding technique to 'HRZ-CS-24-0004L', wherein representative seed of the inbred cucumber variety 'HRZ-CS-24-0004L' has been deposited under NCIMB Accession No. 44526.

249. A method for producing a cucumber seed derived from inbred cucumber variety 'HRZ-CS-24-0004L', the method comprising:

crossing a stock cucumber plant with itself or another cucumber plant, thereby producing the cucumber seed derived from inbred cucumber variety 'HRZ-CS-24-0004L', wherein the stock cucumber plant is a product of applying a plant breeding technique to 'HRZ-CS-24-0004L', wherein a representative sample of seed of inbred cucumber variety 'HRZ-CS-24-0004L' has been deposited under NCIMB Accession No. 44526.

250. The method of embodiment 248 or 249, wherein said plant breeding technique is recurrent selection.

251. The method of embodiment 248 or 249, wherein said plant breeding technique is mass selection.

252. The method of embodiment 248 or 249, wherein said plant breeding technique is hybridization.

253. The method of embodiment 248 or 249, wherein said plant breeding technique is open-pollination.

254. The method of embodiment 248 or 249, wherein said plant breeding technique is backcrossing.

255. The method of embodiment 248 or 249, wherein said plant breeding technique is pedigree breeding.

256. A method for producing nucleic acids, the method comprising isolating nucleic acids from the plant, plant part, or plant cell of any one of embodiments 204-205, or 209-210.

257. A seed of cucumber variety 'HRZ-CS-24-0004L', wherein a representative sample of seed of said cucumber variety 'HRZ-CS-24-0004L' is deposited under NCIMB Accession No. 44526.

258. The seed of embodiment 257, wherein the seed has been technically treated.

259. The seed of embodiment 258, whereby the technical treatment is selected from the group consisting of: dressing, pelleting, encrustation, coloring, coating, priming, and combinations thereof.

260. A method of introducing a desired trait into inbred cucumber variety 'HRZ-CS-24-0004L', the method comprising:

a) crossing cucumber variety 'HRZ-CS-24-0004L' with a second cucumber plant comprising a desired trait to produce $F_1$ progeny plants, wherein a representative sample of seed of said cucumber variety 'HRZ-CS-24-0004L' is deposited under NCIMB Accession No. 44526;

b) selecting $F_1$ progeny plants that have the desired trait to produce selected $F_1$ progeny plants;

c) backcrossing selected $F_1$ progeny plants with cucumber variety 'HRZ-CS-24-0004L' to produce backcross progeny plants;

d) selecting backcross progeny plants that have the desired trait; and e) repeating steps c) and d) one or more times in succession to produce selected second or higher backcross progeny plants that comprise the desired trait and otherwise all the physiological and morphological characteristics of cucumber variety 'HRZ-CS-24-0004L'.

261. A cucumber plant produced by the method of embodiment 260, wherein the plant has the desired trait and otherwise all the physiological and morphological characteristics of cucumber variety 'HRZ-CS-24-0004L'.

262. A prime seedless cucumber fruit of inbred cucumber variety 'HRZ-CS-24-0004L', wherein said fruit has:

a length of between about 5 cm and about 6.5 cm;
a diameter of between about 1.1 cm and about 1.5 cm; and
a weight of between about 10 grams and about 13 grams, wherein representative seed of inbred cucumber variety 'HRZ-CS-24-0004L' has been deposited under NCIMB Accession No. 44526.

263. The prime cucumber fruit of embodiment 262, wherein said fruit has a fruit juice with a total soluble solids of about 2.0° Brix.

264. The prime cucumber fruit of embodiment 262, wherein said fruit juice has a total soluble solids of between about 1.5° Brix and about 2.5° Brix.

265. The prime cucumber fruit of any one of embodiments 262-264, wherein said fruit further has at least one characteristic selected from:
i) an absence of fruit sutures; and
ii) a crunchy texture.

266. The prime cucumber fruit of embodiment 262, wherein said fruit has an increased volatile organic compound level when compared to cucumber variety 'Qwerty' or 'Quete' when grown and harvested under the same conditions.

267. The prime cucumber fruit of embodiment 266, wherein the increased volatile organic compounds comprise (E,Z)-2,6-nonadienal and (E)-2-nonenal.

268. The prime cucumber fruit of any one of embodiments 262-267, wherein said fruit has a water content of at least about 95%.

269. The prime cucumber fruit of any one of embodiments 262-268, wherein said fruit has a decreased cucurbitacin content when compared to cucumber variety 'Qwerty' or 'Quete' when grown and harvested under the same conditions.

270. A plant of inbred cucumber variety 'HRZ-CS-24-0004L' comprising a transgene conferring a desired trait, a sample of seed of said variety having been deposited under NCIMB Accession No. 44526.

271. A method of producing a composite plant, the method comprising grafting a rootstock or a scion of inbred cucumber variety 'HRZ-CS-24-0004L' to another plant, thereby producing a composite plant, wherein a representative sample of seed of said cucumber variety is deposited under NCIMB Accession No. 44526.

272. A composite plant produced by the method of embodiment 271.

273. A method for producing seed derived from cucumber variety 'HRZ-CS-24-0004L', the method comprising:
applying a chemical to a plant of variety 'HRZ-CS-24-0004L' to induce male flower formation;
growing the plant until it sets at least one fruit;
harvesting the fruit; and
harvesting at least one seed from the fruit.

274. The method of embodiment 273, wherein the chemical to induce male flowering is an agent inhibiting ethylene action.

275. The method of embodiment 274, wherein the agent inhibiting ethylene action is selected from silver nitrate, silver thiosulfate, gibberellic acid, 1-methylcyclopropene, and combinations thereof.

276. A plant cell from inbred cucumber variety 'HRZ-CS-24-0004L', wherein representative seed of the variety has been deposited under NCIMB Accession No. 44526.

277. The plant cell of embodiment 276, wherein the plant cell is from a plant part selected from the group consisting of a seed, a meristem, a cotyledon, a hypocotyl, a leaf, an anther, a root, a root tip, a pistil, a petiole, a flower, a stalk, or a stem.

278. A plant cell of cucumber variety, which is a descendant of 'HRZ-CS-24-0004L', the descendant expressing the physiological and morphological characteristics of inbred cucumber variety 'HRZ-CS-24-0004L' as determined at the 5% significance level when grown under substantially similar environmental conditions, wherein representative seed of inbred cucumber variety 'HRZ-CS-24-0004L' has been deposited under NCIMB Accession No. 44526.

279. A plant cell from a tissue culture produced from the plant cell of any one of embodiments 276-278.

280. A plant cell from a cucumber plant regenerated from the tissue culture defined in embodiment 279, said plant expressing the physiological and morphological characteristics of variety 'HRZ-CS-24-0004L' listed in Table 1, as determined at the 5% significance level when grown under substantially similar environmental conditions, wherein representative seed of 'HRZ-CS-24-0004L' has been deposited under NCIMB Accession No. 44526.

281. A locus converted plant cell from a locus converted plant obtained by introducing a locus conversion into inbred cucumber variety 'HRZ-CS-24-0004L', wherein the locus converted plant cell is the same as a plant cell from 'HRZ-CS-24-0004L' except for the locus conversion, and a plant grown from the plant cell expresses the physiological and morphological characteristics of inbred cucumber variety 'HRZ-CS-24-0004L' listed in Table 1 as determined at the 5% significance level except for a trait conferred by the locus conversion, when grown under substantially similar environmental conditions, and wherein representative seed of the variety has been deposited under NCIMB Accession No. 44526.

282. The locus converted plant cell of embodiment 281, wherein the locus conversion comprises a transgene.

283. The locus converted plant cell of embodiment 281 or 282, wherein the locus conversion confers a trait selected from the group consisting of male sterility, herbicide tolerance, insect resistance, pest resistance, disease resistance, powdery mildew resistance, environmental stress tolerance, delayed senescence, controlled ripening, modified carbohydrate metabolism, or modified protein metabolism.

284. Use of a cucumber plant variety designated 'HRZ-CS-24-0004L', wherein representative seed of the variety has been deposited under NCIMB Accession No. 44526, for isolating nucleic acids from the variety.

285. Use of a cucumber plant variety designated 'HRZ-CS-24-0004L', wherein representative seed of the variety has been deposited under NCIMB Accession No. 44526, to produce a commodity plant product.

286. The use of embodiment 285, wherein the commodity plant product is selected from seed and harvested cucumber fruit.

287. The use of embodiment 286, wherein the harvested cucumber fruit is processed.

288. Use of a cucumber plant variety designated 'HRZ-CS-24-0004L', wherein representative seed of the variety has been deposited under NCIMB Accession No. 44526, to produce a cucumber fruit.

289. Use of a cucumber plant variety designated 'HRZ-CS-24-0004L', wherein representative seed of the variety has been deposited under NCIMB Accession No. 44526, to grow subsequent generations.
290. Use of a cucumber plant variety designated 'HRZ-CS-24-0004L', wherein representative seed of the variety has been deposited under NCIMB Accession No. 44526, for vegetative propagation.
291. Use of a cucumber plant variety designated 'HRZ-CS-24-0004L', wherein representative seed of the variety has been deposited under NCIMB Accession No. 44526, as a recipient of a conversion locus.
292. Use of a cucumber plant variety designated 'HRZ-CS-24-0004L', wherein representative seed of the variety has been deposited under NCIMB Accession No. 44526, to produce a genetic marker profile.
292.1 The use of embodiment 292, wherein the genetic marker profile comprises at least one polymorphism from Table 5.
292.2 The use of embodiment 292, wherein the genetic marker profile comprises at least one polymorphism from selected from Table 7.
292.3 The use of embodiment 292, wherein the genetic marker profile comprises at least one polymorphism from selected from Table 8.
292.4 The use of embodiment 292, wherein the genetic marker profile comprises at least one polymorphism from selected from Table 9.
292.5 The use of embodiment 292, wherein the genetic marker profile comprises at least one polymorphism from selected from Table 10.
292.6 The use of embodiment 292, wherein the genetic marker profile comprises at least one polymorphism from selected from Table 11.
292.7 The use of embodiment 292, wherein the genetic marker profile comprises at least one polymorphism from selected from Table 12.
292.8 The use of any one of embodiments 292.2-292.7, wherein the genetic marker profile further comprises at least one polymorphism from selected from Table 6.
293. Use of a cucumber plant variety designated 'HRZ-CS-24-0004L', wherein representative seed of the variety has been deposited under NCIMB Accession No. 44526, as a source of seed, wherein said use comprises applying a chemical to induce male flower formation.
294. The use of embodiment 293, wherein the chemical to induce male flowering is an agent inhibiting ethylene action.
295. The use of embodiment 294, wherein the agent inhibiting ethylene action is selected from silver nitrate, silver thiosulfate, gibberellic acid, 1-methylcyclopropene, and combinations thereof. 296. Use of a cucumber plant variety designated 'HRZ-CS-24-0004L', wherein representative seed of the variety has been deposited under NCIMB Accession No. 44526, as a crop.
297. Use of a cucumber plant variety designated 'HRZ-CS-24-0004L', wherein representative seed of the variety has been deposited under NCIMB Accession No. 44526, as a recipient of a transgene.
298. Use of a cucumber plant variety designated 'HRZ-CS-24-0004L', wherein representative seed of the variety has been deposited under NCIMB Accession No. 44526, as a source of breeding material.
299. Use of a cucumber plant variety designated 'HRZ-CS-24-0004L', wherein representative seed of the variety has been deposited under NCIMB Accession No. 44526, for producing a plant derived from the variety.
300. Use of a cucumber plant variety designated 'HRZ-CS-24-0004L', wherein representative seed of the variety has been deposited under NCIMB Accession No. 44526, for producing a plant derived from the variety, wherein the plant derived from the variety produces prime fruit between approximately 4.0 cm and approximately 6.0 cm in length.
301. Use of embodiment 300, wherein the plant derived from the variety produces a greater number of fruit compared to a similar commercial variety that is not derived from 'HRZ-CS-24-0004L'.
302. The use of any one of embodiments 299-301, wherein the plant derived from the variety is a first, second, third or fourth generation progeny plant.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A plant, plant part, or plant cell of hybrid cucumber variety 'HRZ-CS-24-0001H', representative sample of seed of said cucumber variety having been deposited under NCIMB Accession No. 44490.

2. The plant part of claim 1, wherein the plant part is a leaf, a fruit, a pollen, an ovary, an ovule, an embryo sac, a stem, a scion, a root, a rootstock, or a cutting.

3. A seed that produces the plant of claim 1.

4. A cucumber plant having all the physiological and morphological characteristics of the plant of claim 1, when grown under the same environmental conditions.

5. A tissue culture of regenerable cells produced from the plant, plant part, or plant cell of claim 1.

6. The tissue culture of claim 5, wherein the regenerable cells are obtained from a meristem, a cotyledon, a hypocotyl, a leaf, an anther, a root, a root tip, a pistil, a petiole, a flower, a stalk, a fruit, embryo, or a stem.

7. A cucumber plant regenerated from the tissue culture of claim 5, wherein a cucumber plant regenerated from the tissue culture has all of the physiological and morphological characteristics of cucumber variety 'HRZ-CS-24-0001H' when grown in the same environmental conditions.

8. A method of producing the plant of claim 1, the method comprising: vegetatively propagating at least a part of a plant of cucumber variety 'HRZ-CS-24-0001H'.

9. A plant produced by the method of claim 8, wherein the plant has all the physiological and morphological characteristics of variety 'HRZ-CS-24-0001H' when grown under the same environmental conditions.

10. A method for producing a cucumber seed derived from 'HRZ-CS-24-0001H', the method comprising: a) crossing a first cucumber plant with a second cucumber plant and harvesting resultant cucumber seed, wherein the first cucumber plant and/or second cucumber plant is the cucumber plant of claim 1.

11. The method of claim 10, further comprising the steps of:

b) growing the seed produced by step a) to produce a progeny cucumber plant derived from 'HRZ-CS-24-0001H', and optionally treating the progeny cucumber plant with a chemical to induce male flowering;

c) crossing the progeny cucumber plant derived from 'HRZ-CS-24-0001H' with itself or a second cucumber plant to produce a progeny seed of subsequent generation;

d) growing the progeny seed of subsequent generation to produce a progeny plant of subsequent generation; and e) repeating steps c) and/or d) to produce a cucumber seed or plant further derived from 'HRZ-CS-24-0001H'.

12. The method of claim 11, wherein the method further comprises use of a molecular marker to screen the progeny cucumber plant derived from 'HRZ-CS-24-0001H'.

13. A method of introducing a desired trait into cucumber variety 'HRZ-CS-24-0001H', the method comprising introducing a single locus conversion conferring the desired trait into the plant, the plant part, or plant cell of claim 1, thereby producing a plant of cucumber variety 'HRZ-CS-24-0001H' comprising the desired trait.

14. The method of claim 13, wherein the single locus conversion is introduced into the plant, plant part, or plant cell by a genetic transformation.

15. The method of claim 13, wherein the single locus conversion is introduced into the plant, plant part, or plant cell by a gene-editing technique.

16. The method of claim 15, wherein the gene-editing technique is a nuclease selected from the group consisting of zinc finger nuclease, transcription activator-like effector nuclease (TALEN), engineered homing endonuclease/meganuclease, and clustered regularly interspaced short palindromic repeat (CRISPR)-associated proteins (Cas).

17. The method of claim 13, wherein the desired trait is male sterility, herbicide tolerance, insect resistance, pest resistance, disease resistance, powdery mildew resistance, environmental stress tolerance, delayed senescence, controlled ripening, modified carbohydrate metabolism, or modified protein metabolism.

18. A cucumber plant produced by the method of claim 13, wherein the plant has the desired trait and otherwise all the physiological and morphological characteristics of cucumber variety 'HRZ-CS-24-0001H'.

19. A method for developing a cucumber plant in a cucumber breeding program, the method comprising applying at least one plant breeding technique to the plant of claim 1.

20. The method of claim 19, wherein the plant breeding technique is selected from application of one or more chemicals to induce male flowers, selfing, recurrent selection, backcrossing, pedigree breeding, mass selection, mutation breeding, genetic marker enhanced selection, genetic transformation, and combinations thereof.

21. A method for producing a cucumber plant derived from hybrid cucumber variety 'HRZ-CS-24-0001H', the method comprising:

propagating a vegetative cutting from a stock cucumber plant, thereby producing the cucumber plant derived from variety 'HRZ-CS-24-0001H', wherein the stock cucumber plant is a product of applying a plant breeding technique to 'HRZ-CS-24-0001H', wherein representative seed of the hybrid cucumber variety 'HRZ-CS-24-0001H' has been deposited under NCIMB Accession No. 44490.

22. A method for producing a cucumber seed derived from hybrid cucumber variety 'HRZ-CS-24-0001H', the method comprising:

crossing a stock cucumber plant with itself or another cucumber plant, thereby producing the cucumber seed derived from hybrid cucumber variety 'HRZ-CS-24-0001H', wherein the stock cucumber plant is a product of applying a plant breeding technique to 'HRZ-CS-24-0001H', wherein a representative sample of seed of hybrid cucumber variety 'HRZ-CS-24-0001H' has been deposited under NCIMB Accession No. 44490.

23. A method for producing nucleic acids, the method comprising isolating nucleic acids from the plant, plant part, or plant cell of claim 1.

24. A method for producing hybrid cucumber variety 'HRZ-CS-24-0001H' seed, the method comprising crossing cucumber variety 'HRZ-CS-24-0003L', representative seed of 'HRZ-CS-24-0003L' having been deposited under NCIMB Accession No. 44525, with cucumber variety 'HRZ-CS-24-0004L', representative seed of 'HRZ-CS-24-0004L' having been deposited under NCIMB Accession No. 44526.

* * * * *

SEQUENCE LISTING

```
Sequence total quantity: 108
SEQ ID NO: 1           moltype = DNA  length = 61
FEATURE                Location/Qualifiers
source                 1..61
                       mol_type = genomic DNA
                       organism = Cucumis sativus
SEQUENCE: 1
cttggataac aattcaaatt tattgttacc tctgaagaaa taaagactat tattaccaac  60
c                                                                  61

SEQ ID NO: 2           moltype = DNA  length = 61
FEATURE                Location/Qualifiers
source                 1..61
                       mol_type = genomic DNA
                       organism = Cucumis sativus
SEQUENCE: 2
ttggagtgca gttattatag gttgtgtttg gagtaaatat tattataatt tgagttacta  60
```

```
t                                                                   61

SEQ ID NO: 3            moltype = DNA  length = 61
FEATURE                 Location/Qualifiers
source                  1..61
                        mol_type = genomic DNA
                        organism = Cucumis sativus
SEQUENCE: 3
tcattatcga aaaaattcga caaaacctac ataattatgc caatacatgt ccttatcttc  60
a                                                                   61

SEQ ID NO: 4            moltype = DNA  length = 61
FEATURE                 Location/Qualifiers
source                  1..61
                        mol_type = genomic DNA
                        organism = Cucumis sativus
SEQUENCE: 4
attatcgaaa aaattcgaca aaacctacat aattatgcca atacatgtcc ttatcttcaa  60
c                                                                   61

SEQ ID NO: 5            moltype = DNA  length = 61
FEATURE                 Location/Qualifiers
source                  1..61
                        mol_type = genomic DNA
                        organism = Cucumis sativus
SEQUENCE: 5
tattaatatc taaaatcaaa attttagtag ggtggcgatt tcaaatagaa atttaaaatc  60
a                                                                   61

SEQ ID NO: 6            moltype = DNA  length = 61
FEATURE                 Location/Qualifiers
source                  1..61
                        mol_type = genomic DNA
                        organism = Cucumis sativus
SEQUENCE: 6
atctttaaga gaacattgca cttagtaaat aagcttcgtt tgctatttct tggttttaac  60
t                                                                   61

SEQ ID NO: 7            moltype = DNA  length = 61
FEATURE                 Location/Qualifiers
source                  1..61
                        mol_type = genomic DNA
                        organism = Cucumis sativus
SEQUENCE: 7
tggaatgatt tgaactcaaa atctttagct cggggtatat acgggtacat ataatattat  60
a                                                                   61

SEQ ID NO: 8            moltype = DNA  length = 61
FEATURE                 Location/Qualifiers
source                  1..61
                        mol_type = genomic DNA
                        organism = Cucumis sativus
SEQUENCE: 8
gaatgatttg aactcaaaat ctttagctcg gggtatatac gggtacatat aatattatat  60
a                                                                   61

SEQ ID NO: 9            moltype = DNA  length = 61
FEATURE                 Location/Qualifiers
source                  1..61
                        mol_type = genomic DNA
                        organism = Cucumis sativus
SEQUENCE: 9
aatgatttga actcaaaatc tttagctcgg ggtatatacg ggtacatata atattatata  60
t                                                                   61

SEQ ID NO: 10           moltype = DNA  length = 61
FEATURE                 Location/Qualifiers
source                  1..61
                        mol_type = genomic DNA
                        organism = Cucumis sativus
SEQUENCE: 10
ttagctcggg gtatatacgg gtacatataa tattatatat atacaacaaa agtagtcaaa  60
a                                                                   61

SEQ ID NO: 11           moltype = DNA  length = 61
FEATURE                 Location/Qualifiers
source                  1..61
                        mol_type = genomic DNA
                        organism = Cucumis sativus
```

```
SEQUENCE: 11
tcatgagttt ggttcaaagt gacatgacta ttataaaata tgaaaaatgg tttactaagt  60
t                                                                  61

SEQ ID NO: 12          moltype = DNA  length = 61
FEATURE                Location/Qualifiers
source                 1..61
                       mol_type = genomic DNA
                       organism = Cucumis sativus
SEQUENCE: 12
gggtcgagaa atcacctctc aactaattaa gttaacacct ccttaacggc ttcctaatat  60
t                                                                  61

SEQ ID NO: 13          moltype = DNA  length = 61
FEATURE                Location/Qualifiers
source                 1..61
                       mol_type = genomic DNA
                       organism = Cucumis sativus
SEQUENCE: 13
ttttttttaa aaaaacttat ctgcatataa ttgtgaaaaa attaataatt taatgtgttt  60
t                                                                  61

SEQ ID NO: 14          moltype = DNA  length = 61
FEATURE                Location/Qualifiers
source                 1..61
                       mol_type = genomic DNA
                       organism = Cucumis sativus
SEQUENCE: 14
ttttttaaaa aaacttatct gcatataatt gtgaaaaaat taataattta atgtgttttg  60
t                                                                  61

SEQ ID NO: 15          moltype = DNA  length = 61
FEATURE                Location/Qualifiers
source                 1..61
                       mol_type = genomic DNA
                       organism = Cucumis sativus
SEQUENCE: 15
taacaagcaa ccaaatcgaa catgaacata tatccattgg ctctgacatt aatatctctt  60
a                                                                  61

SEQ ID NO: 16          moltype = DNA  length = 61
FEATURE                Location/Qualifiers
source                 1..61
                       mol_type = genomic DNA
                       organism = Cucumis sativus
SEQUENCE: 16
ttcaacaaca tagagtaaga agattcaaac atctgacttg ttgatagagg acatacacct  60
t                                                                  61

SEQ ID NO: 17          moltype = DNA  length = 61
FEATURE                Location/Qualifiers
source                 1..61
                       mol_type = genomic DNA
                       organism = Cucumis sativus
SEQUENCE: 17
gattcaaaca tctgacttgt tgatagagga catacacctt aataagatgt tcgttgtatt  60
a                                                                  61

SEQ ID NO: 18          moltype = DNA  length = 61
FEATURE                Location/Qualifiers
source                 1..61
                       mol_type = genomic DNA
                       organism = Cucumis sativus
SEQUENCE: 18
ttattaagac ataaatatga aaaaacgagt gctaaatgcc ccaagcttaa acttctcttt  60
t                                                                  61

SEQ ID NO: 19          moltype = DNA  length = 61
FEATURE                Location/Qualifiers
source                 1..61
                       mol_type = genomic DNA
                       organism = Cucumis sativus
SEQUENCE: 19
tcttttagta gctaacacca gaaacttgat tgtccttttt agaggattta aaaccaaggc  60
t                                                                  61

SEQ ID NO: 20          moltype = DNA  length = 61
FEATURE                Location/Qualifiers
source                 1..61
```

```
                         mol_type = genomic DNA
                         organism = Cucumis sativus
SEQUENCE: 20
caccagaaac ttgattgtcc tttttagagg atttaaaacc aaggctgctt ctaaacttaa  60
g                                                                  61

SEQ ID NO: 21            moltype = DNA  length = 61
FEATURE                  Location/Qualifiers
source                   1..61
                         mol_type = genomic DNA
                         organism = Cucumis sativus
SEQUENCE: 21
ttaagctaag atagatatta tttgtgtatt tcattataca aatagacata gtagtttatc  60
a                                                                  61

SEQ ID NO: 22            moltype = DNA  length = 61
FEATURE                  Location/Qualifiers
source                   1..61
                         mol_type = genomic DNA
                         organism = Cucumis sativus
SEQUENCE: 22
gctaagatag atattatttg tgtatttcat tatacaaata gacatagtag tttatcatag  60
t                                                                  61

SEQ ID NO: 23            moltype = DNA  length = 61
FEATURE                  Location/Qualifiers
source                   1..61
                         mol_type = genomic DNA
                         organism = Cucumis sativus
SEQUENCE: 23
ctaagataga tattatttgt gtatttcatt atacaaatag acatagtagt ttatcatagt  60
t                                                                  61

SEQ ID NO: 24            moltype = DNA  length = 61
FEATURE                  Location/Qualifiers
source                   1..61
                         mol_type = genomic DNA
                         organism = Cucumis sativus
SEQUENCE: 24
tagatattat ttgtgtattt cattatacaa atagacatag tagtttatca tagtttatta  60
t                                                                  61

SEQ ID NO: 25            moltype = DNA  length = 61
FEATURE                  Location/Qualifiers
source                   1..61
                         mol_type = genomic DNA
                         organism = Cucumis sativus
SEQUENCE: 25
attatttgtg tatttcatta tacaaataga catagtagtt tatcatagtt tattatagat  60
a                                                                  61

SEQ ID NO: 26            moltype = DNA  length = 61
FEATURE                  Location/Qualifiers
source                   1..61
                         mol_type = genomic DNA
                         organism = Cucumis sativus
SEQUENCE: 26
tctttggtcc tccgctccct ctgtcgacga cgatcgcctc caccgctaca cttccgagcc  60
g                                                                  61

SEQ ID NO: 27            moltype = DNA  length = 61
FEATURE                  Location/Qualifiers
source                   1..61
                         mol_type = genomic DNA
                         organism = Cucumis sativus
SEQUENCE: 27
taattgagtt tgaaagactg tatcgttcaa cgacaagtgt tgctgtgaag atgacatttt  60
t                                                                  61

SEQ ID NO: 28            moltype = DNA  length = 61
FEATURE                  Location/Qualifiers
source                   1..61
                         mol_type = genomic DNA
                         organism = Cucumis sativus
SEQUENCE: 28
acaaaaaaat taaagttata aaaattgatg cgaaggttag cggatgaatt tgcaatctaa  60
g                                                                  61

SEQ ID NO: 29            moltype = DNA  length = 61
```

```
FEATURE                 Location/Qualifiers
source                  1..61
                        mol_type = genomic DNA
                        organism = Cucumis sativus
SEQUENCE: 29
caaaaaaatt aaagttataa aaattgatgc gaaggttagc ggatgaattt gcaatctaag  60
g                                                                  61

SEQ ID NO: 30           moltype = DNA  length = 61
FEATURE                 Location/Qualifiers
source                  1..61
                        mol_type = genomic DNA
                        organism = Cucumis sativus
SEQUENCE: 30
gatgcgaagg ttagcggatg aatttgcaat ctaaggaggg ttataaacct tcgacaatat  60
t                                                                  61

SEQ ID NO: 31           moltype = DNA  length = 61
FEATURE                 Location/Qualifiers
source                  1..61
                        mol_type = genomic DNA
                        organism = Cucumis sativus
SEQUENCE: 31
tgcatcgcat gctaaccttg caagaggtat tgtgtgtgtg cttgccacct atctagtgtc  60
c                                                                  61

SEQ ID NO: 32           moltype = DNA  length = 61
FEATURE                 Location/Qualifiers
source                  1..61
                        mol_type = genomic DNA
                        organism = Cucumis sativus
SEQUENCE: 32
tcaacccgta taaggctttc gaagcttgca gacctgatta ttaaattgag cttcaaatct  60
t                                                                  61

SEQ ID NO: 33           moltype = DNA  length = 61
FEATURE                 Location/Qualifiers
source                  1..61
                        mol_type = genomic DNA
                        organism = Cucumis sativus
SEQUENCE: 33
tattatataa cacacattga tattatcaaa aaaatgtgac aacttcaaat tagcatgtga  60
a                                                                  61

SEQ ID NO: 34           moltype = DNA  length = 61
FEATURE                 Location/Qualifiers
source                  1..61
                        mol_type = genomic DNA
                        organism = Cucumis sativus
SEQUENCE: 34
ttttgttaga cacactgtaa atatttagat gttgtgttat atttacgaaa atgttccaaa  60
t                                                                  61

SEQ ID NO: 35           moltype = DNA  length = 61
FEATURE                 Location/Qualifiers
source                  1..61
                        mol_type = genomic DNA
                        organism = Cucumis sativus
SEQUENCE: 35
ctaaacatcc aaagaagttt tctacacgag agagagggag aaaattacta ataacttccc  60
c                                                                  61

SEQ ID NO: 36           moltype = DNA  length = 61
FEATURE                 Location/Qualifiers
source                  1..61
                        mol_type = genomic DNA
                        organism = Cucumis sativus
SEQUENCE: 36
acaatgcatt tcattttacc aagttcaatg ttagtcagat tagtcaacat ttctatgttt  60
c                                                                  61

SEQ ID NO: 37           moltype = DNA  length = 61
FEATURE                 Location/Qualifiers
source                  1..61
                        mol_type = genomic DNA
                        organism = Cucumis sativus
SEQUENCE: 37
tttcctctcc tatcttaatt ctctctatcc atacatttaa aatatatatt aacagtacat  60
c                                                                  61
```

```
SEQ ID NO: 38          moltype = DNA  length = 61
FEATURE                Location/Qualifiers
source                 1..61
                       mol_type = genomic DNA
                       organism = Cucumis sativus
SEQUENCE: 38
cttactgtag atacattttt gtatccatta aatataacca atcaacagtg caatgaccct  60
t                                                                   61

SEQ ID NO: 39          moltype = DNA  length = 61
FEATURE                Location/Qualifiers
source                 1..61
                       mol_type = genomic DNA
                       organism = Cucumis sativus
SEQUENCE: 39
tgtatccatt aaatataacc aatcaacagt gcaatgaccc tttacaaatt gctcataagt  60
a                                                                   61

SEQ ID NO: 40          moltype = DNA  length = 61
FEATURE                Location/Qualifiers
source                 1..61
                       mol_type = genomic DNA
                       organism = Cucumis sativus
SEQUENCE: 40
agaaagaagg aaagaaacaa tatcaaaata gttttttag aattttaaaa aataacaaat  60
t                                                                   61

SEQ ID NO: 41          moltype = DNA  length = 61
FEATURE                Location/Qualifiers
source                 1..61
                       mol_type = genomic DNA
                       organism = Cucumis sativus
SEQUENCE: 41
ataaagggtt ggaacctacc aataatatcc aaatgaaaat gagagtttat ttttaatgtt  60
g                                                                   61

SEQ ID NO: 42          moltype = DNA  length = 61
FEATURE                Location/Qualifiers
source                 1..61
                       mol_type = genomic DNA
                       organism = Cucumis sativus
SEQUENCE: 42
agtgactaag taagaaaatt atgcttttaa gaaaacaaag tgacgtgaga ttgttggaat  60
a                                                                   61

SEQ ID NO: 43          moltype = DNA  length = 61
FEATURE                Location/Qualifiers
source                 1..61
                       mol_type = genomic DNA
                       organism = Cucumis sativus
SEQUENCE: 43
ctatgaaaaa ttgtcttcct ataaggttga gatatatata tataaaataa aaagttattt  60
t                                                                   61

SEQ ID NO: 44          moltype = DNA  length = 61
FEATURE                Location/Qualifiers
source                 1..61
                       mol_type = genomic DNA
                       organism = Cucumis sativus
SEQUENCE: 44
attggtttat gatccaacca ttaaactgaa tctctctcaa gccaatgaga ggtcgagact  60
t                                                                   61

SEQ ID NO: 45          moltype = DNA  length = 61
FEATURE                Location/Qualifiers
source                 1..61
                       mol_type = genomic DNA
                       organism = Cucumis sativus
SEQUENCE: 45
gaatgttttt ttaaactaat gacaaaagta cggtaggtag gaaagaaagg atagaaatgg  60
g                                                                   61

SEQ ID NO: 46          moltype = DNA  length = 61
FEATURE                Location/Qualifiers
source                 1..61
                       mol_type = genomic DNA
                       organism = Cucumis sativus
SEQUENCE: 46
```

```
tgaacaacaa aacaaataat aataataata aaaaaaaaca gaaaaaaatt ggatagcatt  60
c                                                                  61

SEQ ID NO: 47          moltype = DNA  length = 61
FEATURE                Location/Qualifiers
source                 1..61
                       mol_type = genomic DNA
                       organism = Cucumis sativus
SEQUENCE: 47
atattatttt ttatgaaaaa atatggatag aataaaaata gatgagtaca actttaaggg  60
a                                                                  61

SEQ ID NO: 48          moltype = DNA  length = 61
FEATURE                Location/Qualifiers
source                 1..61
                       mol_type = genomic DNA
                       organism = Cucumis sativus
SEQUENCE: 48
ttatgtttta gtcaaattta gaggctccta gatatttatt tgcccattgc tcctttgctt  60
c                                                                  61

SEQ ID NO: 49          moltype = DNA  length = 61
FEATURE                Location/Qualifiers
source                 1..61
                       mol_type = genomic DNA
                       organism = Cucumis sativus
SEQUENCE: 49
ttgtgaccat tacatgactc aatagttcca tatgacttat atcgtctacc ttaaaattaa  60
t                                                                  61

SEQ ID NO: 50          moltype = DNA  length = 61
FEATURE                Location/Qualifiers
source                 1..61
                       mol_type = genomic DNA
                       organism = Cucumis sativus
SEQUENCE: 50
tcaaatgacc attggaaaac ctatagccca ttgagaggca gccaatatag taatgcctct  60
a                                                                  61

SEQ ID NO: 51          moltype = DNA  length = 61
FEATURE                Location/Qualifiers
source                 1..61
                       mol_type = genomic DNA
                       organism = Cucumis sativus
SEQUENCE: 51
ttttcattat ccaatttcgc ttcgatttta caaaaaatta tatattttta aggagaatcc  60
a                                                                  61

SEQ ID NO: 52          moltype = DNA  length = 61
FEATURE                Location/Qualifiers
source                 1..61
                       mol_type = genomic DNA
                       organism = Cucumis sativus
SEQUENCE: 52
tccaatttcg cttcgatttt acaaaaaatt atatattttt aaggagaatc caaataaact  60
t                                                                  61

SEQ ID NO: 53          moltype = DNA  length = 61
FEATURE                Location/Qualifiers
source                 1..61
                       mol_type = genomic DNA
                       organism = Cucumis sativus
SEQUENCE: 53
atgtcaatga aataggtact actagcattt cttaggagtt aatgaatgaa acatgtaacc  60
t                                                                  61

SEQ ID NO: 54          moltype = DNA  length = 61
FEATURE                Location/Qualifiers
source                 1..61
                       mol_type = genomic DNA
                       organism = Cucumis sativus
SEQUENCE: 54
cgagacttga accaagggtc ataccttctc aatggcacga gaggggtttt tgtttattgg  60
t                                                                  61

SEQ ID NO: 55          moltype = DNA  length = 61
FEATURE                Location/Qualifiers
source                 1..61
                       mol_type = genomic DNA
```

```
                         organism = Cucumis sativus
SEQUENCE: 55
gagaggggtt tttgtttatt ggttggacca taacaggttg ttcattggag gagcattgat  60
a                                                                  61

SEQ ID NO: 56            moltype = DNA  length = 61
FEATURE                  Location/Qualifiers
source                   1..61
                         mol_type = genomic DNA
                         organism = Cucumis sativus
SEQUENCE: 56
tttttgttta ttggttggac cataacaggt tgttcattgg aggagcattg atatttaaag  60
a                                                                  61

SEQ ID NO: 57            moltype = DNA  length = 61
FEATURE                  Location/Qualifiers
source                   1..61
                         mol_type = genomic DNA
                         organism = Cucumis sativus
SEQUENCE: 57
ttttgctaat gtaccgatat tttgggattc tcaaattaat ttgagaaatg gttctgtaaa  60
a                                                                  61

SEQ ID NO: 58            moltype = DNA  length = 61
FEATURE                  Location/Qualifiers
source                   1..61
                         mol_type = genomic DNA
                         organism = Cucumis sativus
SEQUENCE: 58
tttgttcatt tgattatgat atattaagtt aaaaaacgca tgaatctatt ggttcacaat  60
a                                                                  61

SEQ ID NO: 59            moltype = DNA  length = 61
FEATURE                  Location/Qualifiers
source                   1..61
                         mol_type = genomic DNA
                         organism = Cucumis sativus
SEQUENCE: 59
cacgtgcttg gtgattacaa tctatatttt tcgcccttct ttaaatgaac aagattaaga  60
t                                                                  61

SEQ ID NO: 60            moltype = DNA  length = 61
FEATURE                  Location/Qualifiers
source                   1..61
                         mol_type = genomic DNA
                         organism = Cucumis sativus
SEQUENCE: 60
tggtgattac aatctatatt tttcgccctt ctttaaatga acaagattaa gatactcacg  60
t                                                                  61

SEQ ID NO: 61            moltype = DNA  length = 61
FEATURE                  Location/Qualifiers
source                   1..61
                         mol_type = genomic DNA
                         organism = Cucumis sativus
SEQUENCE: 61
ttcaaaatag taaaggaaaa ttacaagaaa tattttaaca tgaaaacgtt taagaaagtc  60
a                                                                  61

SEQ ID NO: 62            moltype = DNA  length = 61
FEATURE                  Location/Qualifiers
source                   1..61
                         mol_type = genomic DNA
                         organism = Cucumis sativus
SEQUENCE: 62
aaattacaag aaatatttta acatgaaaac gtttaagaaa gtcactcacc aaactttact  60
a                                                                  61

SEQ ID NO: 63            moltype = DNA  length = 61
FEATURE                  Location/Qualifiers
source                   1..61
                         mol_type = genomic DNA
                         organism = Cucumis sativus
SEQUENCE: 63
gaaatttcca aatcaatttt gttatacttt ctaaatagtt taattatttt gttattttta  60
a                                                                  61

SEQ ID NO: 64            moltype = DNA  length = 61
FEATURE                  Location/Qualifiers
```

```
source                  1..61
                        mol_type = genomic DNA
                        organism = Cucumis sativus
SEQUENCE: 64
gaatttggat attacaagca ttccagagca ctttggaaaa tttggagttg atttggagct  60
a                                                                  61

SEQ ID NO: 65           moltype = DNA  length = 61
FEATURE                 Location/Qualifiers
source                  1..61
                        mol_type = genomic DNA
                        organism = Cucumis sativus
SEQUENCE: 65
tttctattaa ttttaaaggt aatggtaatg gatgactatt tgagaaataa taattaagga  60
t                                                                  61

SEQ ID NO: 66           moltype = DNA  length = 61
FEATURE                 Location/Qualifiers
source                  1..61
                        mol_type = genomic DNA
                        organism = Cucumis sativus
SEQUENCE: 66
atggatgact atttgagaaa taataattaa ggatataaca acatttaaaa aagttgcaaa  60
t                                                                  61

SEQ ID NO: 67           moltype = DNA  length = 61
FEATURE                 Location/Qualifiers
source                  1..61
                        mol_type = genomic DNA
                        organism = Cucumis sativus
SEQUENCE: 67
tgtagtttta tcatttataa tactatatat catataaaat tttgattggt tacttgtttt  60
g                                                                  61

SEQ ID NO: 68           moltype = DNA  length = 61
FEATURE                 Location/Qualifiers
source                  1..61
                        mol_type = genomic DNA
                        organism = Cucumis sativus
SEQUENCE: 68
ttttagaaaa aaaaaaagtt tattttctca caaaaaaaaa ttgtttgtga tttccatact  60
t                                                                  61

SEQ ID NO: 69           moltype = DNA  length = 61
FEATURE                 Location/Qualifiers
source                  1..61
                        mol_type = genomic DNA
                        organism = Cucumis sativus
SEQUENCE: 69
tatatatcat ataaaatttt gattggttac ttgttttgag tttatgtatt gcactctttt  60
t                                                                  61

SEQ ID NO: 70           moltype = DNA  length = 61
FEATURE                 Location/Qualifiers
source                  1..61
                        mol_type = genomic DNA
                        organism = Cucumis sativus
SEQUENCE: 70
ttcctttcat ttcttatatt ttagatgtat tgagttcatt caaataaaag tatatgtatt  60
a                                                                  61

SEQ ID NO: 71           moltype = DNA  length = 61
FEATURE                 Location/Qualifiers
source                  1..61
                        mol_type = genomic DNA
                        organism = Cucumis sativus
SEQUENCE: 71
gttacataca ttatatcggt ttagaaagat cagaccaatt ttttttagaa aaaaatagtt  60
t                                                                  61

SEQ ID NO: 72           moltype = DNA  length = 61
FEATURE                 Location/Qualifiers
source                  1..61
                        mol_type = genomic DNA
                        organism = Cucumis sativus
SEQUENCE: 72
actattatca caaagtaact ctcaatagtt tagtctaaac aatcataatt ggtttgtact  60
g                                                                  61
```

```
SEQ ID NO: 73          moltype = DNA  length = 61
FEATURE                Location/Qualifiers
source                 1..61
                       mol_type = genomic DNA
                       organism = Cucumis sativus
SEQUENCE: 73
aagcatacgg cataaactct gagagtaaag cgagaagaaa tattatgaat gaggaccatg  60
c                                                                   61

SEQ ID NO: 74          moltype = DNA  length = 61
FEATURE                Location/Qualifiers
source                 1..61
                       mol_type = genomic DNA
                       organism = Cucumis sativus
SEQUENCE: 74
tgtttcacat ccaactttct tctttgttac atacattata tcggtttaga aagatcagac  60
c                                                                   61

SEQ ID NO: 75          moltype = DNA  length = 61
FEATURE                Location/Qualifiers
source                 1..61
                       mol_type = genomic DNA
                       organism = Cucumis sativus
SEQUENCE: 75
acattatatc ggtttagaaa gatcagacca attttttta gaaaaaaata gttttcaaaa  60
a                                                                   61

SEQ ID NO: 76          moltype = DNA  length = 61
FEATURE                Location/Qualifiers
source                 1..61
                       mol_type = genomic DNA
                       organism = Cucumis sativus
SEQUENCE: 76
ctaccaatat ttctttctaa attctaatta tttgaatttg gtggggtttc tcaaattctt  60
c                                                                   61

SEQ ID NO: 77          moltype = DNA  length = 61
FEATURE                Location/Qualifiers
source                 1..61
                       mol_type = genomic DNA
                       organism = Cucumis sativus
SEQUENCE: 77
tgttttattt ataagtttga ttgattaatt cttttattgc tttaattaaa tttaaatttt  60
a                                                                   61

SEQ ID NO: 78          moltype = DNA  length = 61
FEATURE                Location/Qualifiers
source                 1..61
                       mol_type = genomic DNA
                       organism = Cucumis sativus
SEQUENCE: 78
acataattca tggcaagaaa atttcgttct tgtcaaaaga ttgtgtttta gaataaaaga  60
a                                                                   61

SEQ ID NO: 79          moltype = DNA  length = 61
FEATURE                Location/Qualifiers
source                 1..61
                       mol_type = genomic DNA
                       organism = Cucumis sativus
SEQUENCE: 79
aaagtaggtt tagtttcatt tttaacatat ctcttcttaa ggttaaaact atatttcgtt  60
t                                                                   61

SEQ ID NO: 80          moltype = DNA  length = 61
FEATURE                Location/Qualifiers
source                 1..61
                       mol_type = genomic DNA
                       organism = Cucumis sativus
SEQUENCE: 80
agtaggttta gtttcatttt taacatatct cttcttaagg ttaaaactat atttcgtttt  60
t                                                                   61

SEQ ID NO: 81          moltype = DNA  length = 61
FEATURE                Location/Qualifiers
source                 1..61
                       mol_type = genomic DNA
                       organism = Cucumis sativus
SEQUENCE: 81
aggtttagtt tcatttttaa catatctctt cttaaggtta aaactatatt tcgtttttta  60
```

```
t                                                                   61

SEQ ID NO: 82          moltype = DNA  length = 61
FEATURE                Location/Qualifiers
source                 1..61
                       mol_type = genomic DNA
                       organism = Cucumis sativus
SEQUENCE: 82
tttttagaaa aaaatagttt tcaaaaagtt acattttatt ttaaaatatg gaaaattttt  60
c                                                                   61

SEQ ID NO: 83          moltype = DNA  length = 61
FEATURE                Location/Qualifiers
source                 1..61
                       mol_type = genomic DNA
                       organism = Cucumis sativus
SEQUENCE: 83
attagttcaa gaaaggcttc ccatagcctt agctctttcc ctcaatatga acttttgaac  60
c                                                                   61

SEQ ID NO: 84          moltype = DNA  length = 61
FEATURE                Location/Qualifiers
source                 1..61
                       mol_type = genomic DNA
                       organism = Cucumis sativus
SEQUENCE: 84
taaggaagaa ggggaattgt attgtattat tgaaggaggt cgggttgttc ctttgccttg  60
a                                                                   61

SEQ ID NO: 85          moltype = DNA  length = 61
FEATURE                Location/Qualifiers
source                 1..61
                       mol_type = genomic DNA
                       organism = Cucumis sativus
SEQUENCE: 85
agagtttaca aatatagtaa aagtaattat aataacaaag ttcatgtcac ttgtattttt  60
t                                                                   61

SEQ ID NO: 86          moltype = DNA  length = 61
FEATURE                Location/Qualifiers
source                 1..61
                       mol_type = genomic DNA
                       organism = Cucumis sativus
SEQUENCE: 86
gattttacaa aaaattatat atttttaagg agaatccaaa taaacttttt taaaaaagaa  60
t                                                                   61

SEQ ID NO: 87          moltype = DNA  length = 61
FEATURE                Location/Qualifiers
source                 1..61
                       mol_type = genomic DNA
                       organism = Cucumis sativus
SEQUENCE: 87
actcgatagt atattctatt agataatgca cacattcatg tttcaaatga cttagcttat  60
t                                                                   61

SEQ ID NO: 88          moltype = DNA  length = 61
FEATURE                Location/Qualifiers
source                 1..61
                       mol_type = genomic DNA
                       organism = Cucumis sativus
SEQUENCE: 88
attccaattc aattaataaa ccattaaaaa agaaggagtg gggctaaatt tgattaatta  60
t                                                                   61

SEQ ID NO: 89          moltype = DNA  length = 61
FEATURE                Location/Qualifiers
source                 1..61
                       mol_type = genomic DNA
                       organism = Cucumis sativus
SEQUENCE: 89
ttttcacctt taaatatgtg catgcacatg tcaaaaaaaa aaaaaagcaa ttatatgagc  60
a                                                                   61

SEQ ID NO: 90          moltype = DNA  length = 61
FEATURE                Location/Qualifiers
source                 1..61
                       mol_type = genomic DNA
                       organism = Cucumis sativus
```

```
SEQUENCE: 90
aaattatttt tctttcctct tttcatgttt ctaatttttt ttaaaaaaag acaaattagg  60
g                                                                  61

SEQ ID NO: 91          moltype = DNA  length = 61
FEATURE                Location/Qualifiers
source                 1..61
                       mol_type = genomic DNA
                       organism = Cucumis sativus
SEQUENCE: 91
taatatcaca gttttcatta tccaatttcg cttcgatttt acaaaaaatt atatattttt  60
a                                                                  61

SEQ ID NO: 92          moltype = DNA  length = 61
FEATURE                Location/Qualifiers
source                 1..61
                       mol_type = genomic DNA
                       organism = Cucumis sativus
SEQUENCE: 92
aatatcacag ttttcattat ccaatttcgc ttcgatttta caaaaaatta tatattttta  60
a                                                                  61

SEQ ID NO: 93          moltype = DNA  length = 61
FEATURE                Location/Qualifiers
source                 1..61
                       mol_type = genomic DNA
                       organism = Cucumis sativus
SEQUENCE: 93
tgaacaaggt gcatttcaag tgggctacaa gattcgtctt ttggaatttg attcggaaat  60
t                                                                  61

SEQ ID NO: 94          moltype = DNA  length = 61
FEATURE                Location/Qualifiers
source                 1..61
                       mol_type = genomic DNA
                       organism = Cucumis sativus
SEQUENCE: 94
gcaaattcta attataaagg ataaaacctc gatgctaaaa gctgttttat acaacaattt  60
c                                                                  61

SEQ ID NO: 95          moltype = DNA  length = 61
FEATURE                Location/Qualifiers
source                 1..61
                       mol_type = genomic DNA
                       organism = Cucumis sativus
SEQUENCE: 95
attgctacaa agataatgaa tgttagtgga gctaaaacat ggaaatattt ttttaaataa  60
t                                                                  61

SEQ ID NO: 96          moltype = DNA  length = 61
FEATURE                Location/Qualifiers
source                 1..61
                       mol_type = genomic DNA
                       organism = Cucumis sativus
SEQUENCE: 96
aattacagaa actgttaata ttcaatcaaa gaaaaaacag tctatcactg atacagatct  60
a                                                                  61

SEQ ID NO: 97          moltype = DNA  length = 61
FEATURE                Location/Qualifiers
source                 1..61
                       mol_type = genomic DNA
                       organism = Cucumis sativus
SEQUENCE: 97
agataatgaa tgttagtgga gctaaaacat ggaaatattt ttttaaataa ttttagtgtg  60
t                                                                  61

SEQ ID NO: 98          moltype = DNA  length = 61
FEATURE                Location/Qualifiers
source                 1..61
                       mol_type = genomic DNA
                       organism = Cucumis sativus
SEQUENCE: 98
gataatgaat gttagtggag ctaaaacatg gaaatatttt tttaaataat tttagtgtgt  60
t                                                                  61

SEQ ID NO: 99          moltype = DNA  length = 61
FEATURE                Location/Qualifiers
source                 1..61
```

```
                        mol_type = genomic DNA
                        organism = Cucumis sativus
SEQUENCE: 99
taatgaatgt tagtggagct aaaacatgga aatatttttt taaataattt tagtgtgttt  60
a                                                                  61

SEQ ID NO: 100          moltype = DNA  length = 61
FEATURE                 Location/Qualifiers
source                  1..61
                        mol_type = genomic DNA
                        organism = Cucumis sativus
SEQUENCE: 100
tcgttgctat ccaagtcacc gccactccat cttgtctccg tttgttggtt gcgatttgtt  60
a                                                                  61

SEQ ID NO: 101          moltype = DNA  length = 61
FEATURE                 Location/Qualifiers
source                  1..61
                        mol_type = genomic DNA
                        organism = Cucumis sativus
SEQUENCE: 101
tttgggattc tcaaattaat ttgagaaatg gttctgtaaa atctttcatt acctatgact  60
t                                                                  61

SEQ ID NO: 102          moltype = DNA  length = 61
FEATURE                 Location/Qualifiers
source                  1..61
                        mol_type = genomic DNA
                        organism = Cucumis sativus
SEQUENCE: 102
aatttgagaa atggttctgt aaaatctttc attacctatg acttttatcc cttcacgtac  60
t                                                                  61

SEQ ID NO: 103          moltype = DNA  length = 61
FEATURE                 Location/Qualifiers
source                  1..61
                        mol_type = genomic DNA
                        organism = Cucumis sativus
SEQUENCE: 103
gtttgtagaa gtaccactta gacacttaga cacttaacgt tttgattgaa aactcttgac  60
a                                                                  61

SEQ ID NO: 104          moltype = DNA  length = 61
FEATURE                 Location/Qualifiers
source                  1..61
                        mol_type = genomic DNA
                        organism = Cucumis sativus
SEQUENCE: 104
ggttgtaaac tgtgttagtc aatttatgca caaccaactg tcattcactt tccggcagtt  60
a                                                                  61

SEQ ID NO: 105          moltype = DNA  length = 61
FEATURE                 Location/Qualifiers
source                  1..61
                        mol_type = genomic DNA
                        organism = Cucumis sativus
SEQUENCE: 105
taatataatt tttttatgaa aagtataggg gtaagaagca ggtaaaaatt ctctctacat  60
g                                                                  61

SEQ ID NO: 106          moltype = DNA  length = 61
FEATURE                 Location/Qualifiers
source                  1..61
                        mol_type = genomic DNA
                        organism = Cucumis sativus
SEQUENCE: 106
gtactaatta ttattatttg gggtggtgtt gtttttttct ttattattgt acaattattt  60
t                                                                  61

SEQ ID NO: 107          moltype = DNA  length = 61
FEATURE                 Location/Qualifiers
source                  1..61
                        mol_type = genomic DNA
                        organism = Cucumis sativus
SEQUENCE: 107
ttggattaaa ctaaaaaaaa tagattttca ggtgaatgta ttgatggagt tgctcaattt  60
a                                                                  61

SEQ ID NO: 108          moltype = DNA  length = 61
```

-continued

```
FEATURE                 Location/Qualifiers
source                  1..61
                        mol_type = genomic DNA
                        organism = Cucumis sativus
SEQUENCE: 108
aagaagatgt caatgaaata ggtactacta gcatttctta ggagttaatg aatgaaacat  60
g                                                                   61
```